United States Patent
Astrow et al.

(10) Patent No.: US 11,820,823 B2
(45) Date of Patent: Nov. 21, 2023

(54) T CELL RECEPTOR ANTIGEN BINDING MOLECULES AND METHODS OF USE THEREOF

(71) Applicant: Kite Pharma, Inc., Santa Monica, CA (US)

(72) Inventors: Stephanie Astrow, Los Angeles, CA (US); Stuart Sievers, Van Nuys, CA (US); Jed Wiltzius, Winchester, MA (US)

(73) Assignee: Kite Pharma, Inc., Santa Monica, CA (US)

( * ) Notice: Subject to any disclaimer, the term of this patent is extended or adjusted under 35 U.S.C. 154(b) by 591 days.

(21) Appl. No.: 16/759,680

(22) PCT Filed: Oct. 26, 2018

(86) PCT No.: PCT/US2018/057746
§ 371 (c)(1),
(2) Date: Apr. 27, 2020

(87) PCT Pub. No.: WO2019/084427
PCT Pub. Date: May 2, 2019

(65) Prior Publication Data
US 2020/0308281 A1    Oct. 1, 2020

Related U.S. Application Data

(60) Provisional application No. 62/578,174, filed on Oct. 27, 2017.

(51) Int. Cl.
*C07K 16/28* (2006.01)
*G01N 1/30* (2006.01)
*G01N 33/569* (2006.01)

(52) U.S. Cl.
CPC ........... *C07K 16/2809* (2013.01); *G01N 1/30* (2013.01); *G01N 33/56972* (2013.01); *G01N 2001/305* (2013.01); *G01N 2333/7051* (2013.01)

(58) Field of Classification Search
None
See application file for complete search history.

(56) References Cited

U.S. PATENT DOCUMENTS

| | | | |
|---|---|---|---|
| 6,171,799 B1 * | 1/2001 | Skibbens | C07K 16/2809 |
| | | | 435/7.1 |
| 8,420,348 B2 * | 4/2013 | Goodman | C07K 16/00 |
| | | | 435/7.1 |
| 2011/0038842 A1 * | 2/2011 | Boulter | A61K 35/12 |
| | | | 435/325 |

OTHER PUBLICATIONS

Piche-Nicholas et al., MABS 10(1): 81-94 (Year: 2018).*
Rudikoff et al., Proc Natl Acad Sci USA 79: 1979 (Year: 1982).*
Wu et al., J. Mol. Biol. 294: 151-162 (Year: 1999).*
International Search Report-Written Opinion dated Mar. 19, 2019 for PCT/US2018/057746.
Henry, L. et al. (1989) "Two Distinct Immunogenic Epitopes on the α Chain of Human T Cell Antigen Receptor" Hybridoma 8(6):577-588.
Buri, C. et al. (2005) "Cytotoxic T cells are preferentially activated in the duodenal epithelium from patients with florid coeliac disease" The Journal of Pathology 206(2):178-185.
Thermo Fisher et al. (2019) "TRAC Monoclonal Antibody (3A8) Catalog No. TCR1145 Product data" Thermo Fisher scientific catalog, retrieved from the Internet: URL: https://www.thermofisher.com/order/genome- database/generatePdf?productName=TRAC&assayType=PRANT&detailed=true&productId=TCR 1145.
Bosterbio (2019) "Anti-TCR alpha/TRAC Picoband™ Antibody Catalog No. A05315" retrieved from the Internet: URL: https://www.bosterbio.com/datasheet_new.php?sku=A05315.
Anonymous (2019) "Certificate of Analysis Anti-TCR alpha/TRAC Picoband™ Antibody, catalog #A05315" retrieved from the Internet: URL: https://www.bosterbio.com/antibody_certifcate_of_analysis.php?sku=A05315).
Reed, B.K. et al. (2014) "Detection of Constant Domain of Human T Cell Antigen Receptor Alpha-Chain Via Novel Monoclonal Antibody 7F18" Monoclonal Antibodies in Immunodiagnosis and Immunotherapy 33(6):386-392.

* cited by examiner

*Primary Examiner* — Phuong Huynh

(57) ABSTRACT

Isolated antigen binding molecules that specifically bind to a polypeptide comprising the alpha chain of the constant region of a T cell receptor (TCR) are provided. The antigen binding molecules may be used in the methods provided herein.

18 Claims, 12 Drawing Sheets

Specification includes a Sequence Listing.

| Sequence | CDR1 | CDR2 | CDR3 |
|---|---|---|---|
| 39-4_VL | QASQSVYSSNLLT | EASKLPS | LGIYDCVLADCQA |
| 39-4_VH1 | NNWIH | CVSGSSGNIYYATWAK | GWNL |
| 39-4_VH3 | NNWIH | CVSGSSGNIYYATWAK | GWNL |

Fig. 1A

| Sequence | CDR1 | CDR2 | CDR3 |
|---|---|---|---|
| 39-4_VL | QASQSVYSSNLLT | EASKLPS | LGIYDCVLADCQA |
| 39-4_VH1 | GFDLGNN | SGSSG | GWNL |
| 39-4_VH3 | GFDLGNN | SGSSG | GWNL |

Fig. 1B

| Sequence | CDR1 | CDR2 | CDR3 |
|---|---|---|---|
| 39-4_VL | QASQSVYSSNLLT | EASKLPS | LGIYDCVLADCQA |
| 39-4_VH1 | GFDLGNNW | VSGSSGN | ARGWNL |
| 39-4_VH3 | NNWIH | VSGSSGN | ARGWNL |

Fig. 1C

```
39-4_Vh1    METGLRWLLLVAVLKGVQCQEQLVESGGGLVQPEGSLTLTCTASGFDLGNNWIHWVRHAP
39-4_Vh3    METGLRWLLLVAVLKDVQCQEQLVESGGGLVQPEGSLTLTCTASGFDLGNNWIHWVRHAP
            *************** ********************************************

39-4_Vh1    GKGLEWIACVSGSSGNIYYATWAKGRFTMSKASSTTVTLRMTSLTAADTATYFCARGWNL
39-4_Vh3    GKGLEWIACVSGSSGNIYYATWAKGRFTMSKASSTTVTLRMTSLTAADTATYFCARGWNL
            ************************************************************

39-4_Vh1    WGPGTLVTVSS
39-4_Vh3    WGPGTLVTVSS
            ***********
```

| 8A positive, all counterscreens negative | 6 | 8A positive, 1+ counterscreens positive | 1 |
| 8B positive, all counterscreens negative | 37 | 8B positive, 1+ counterscreens positive | 9 |
| 8A + 8B positive, all counterscreens negative | 24 | 8A + 8B positive, 1+ counterscreens positive | 1 |

Fig. 3D

| Clone ID | IgG OD (undiluted) | IgG OD (1:40 dilution) | ng/mL IgG | specific OD for S: KIP-8A-BSA (undiluted) | specific OD for S: KIP-8A-BSA (1:40 dilution) | specific OD for S: KIP-9B-BSA (undiluted) | specific OD for S: KIP-9B-BSA (1:40 dilution) | Confluence |
|---|---|---|---|---|---|---|---|---|
| D9-1 | 0.96 | 0.21 | 240.00 | 0.07 | 0.03 | 1.51 | 0.34 | +++ |
| D9-2 | 0.98 | 0.28 | 400.00 | 0.07 | 0.00 | 1.66 | 0.43 | +++ |
| D9-3 | 1.14 | 0.63 | 1600.00 | 0.07 | 0.00 | 1.71 | 1.04 | +++ |
| D9-4 | 0.78 | 0.50 | 1280.00 | 0.08 | 0.00 | 1.70 | 0.91 | +++ |
| D9-5 | 1.00 | 0.44 | 1240.00 | 0.07 | 0.05 | 1.60 | 0.90 | +++ |
| D9-6 | 1.01 | 0.32 | 620.00 | 0.07 | 0.00 | 1.60 | 0.50 | +++ |
| D9-7 | 1.13 | 0.29 | 440.00 | 0.08 | 0.05 | 1.51 | 0.44 | +++ |
| D3-1 | 1.09 | 0.39 | 720.00 | 0.08 | 0.05 | 1.61 | 0.72 | +++ |
| D3-2 | 0.96 | 0.17 | 160.00 | 0.08 | 0.00 | 1.41 | 1.07 | + |
| D3-3 | 1.19 | 0.54 | 1200.00 | 0.08 | 0.02 | 1.67 | 0.72 | +++ |
| D3-4 | 1.28 | 0.52 | 1120.00 | 0.09 | 0.00 | 1.80 | 0.81 | +++ |
| D3-5 | 1.11 | 0.36 | 640.00 | 0.07 | 0.10 | 1.56 | 0.67 | +++ |
| D3-6 | 1.08 | 0.67 | 1320.00 | 0.08 | 0.00 | 1.89 | 1.20 | +++ |
| D3-7 | 1.08 | 0.49 | 1040.00 | 0.08 | 0.05 | 1.67 | 0.87 | +++ |
| D3-8 | 1.05 | 0.73 | 2120.00 | 0.07 | 0.08 | 1.79 | 1.15 | +++ |
| D3-9 | 1.19 | 0.21 | 240.00 | 0.08 | 0.09 | 1.48 | 0.38 | +++ |
| D3-10 | 1.08 | 0.61 | 1480.00 | 0.08 | 0.09 | 1.57 | 1.04 | +++ |
| D3-11 | 1.13 | 0.28 | 400.00 | 0.08 | 0.08 | 1.58 | 0.52 | +++ |
| | | | | | 1.40 | | 1.43 | |
| | | | | | (+) CTRL | | (+) CTRL | |

Date: 8/4/2017

(Note: cell density 100% ++++, 70% +++, 50% ++, 30% +, < 30% +/-)

Fig. 4

T CELL RECEPTOR ANTIGEN BINDING MOLECULES AND METHODS OF USE THEREOF

CROSS-REFERENCE TO RELATED APPLICATIONS

This application is the U.S. National Stage of international Application No. PCT/US2018/057746, filed Oct. 26, 2018 which was published in English under PCT Article 21(2), and which in turn claims priority to U.S. Provisional Application No. 62/578,174, filed Oct. 27, 2017, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Oct. 26, 2018, is named K-1056_01_ST25.txt and is 79,930 bytes in size.

TECHNICAL FIELD

This disclosure relates to antigen binding molecules, such as antibodies, which specifically bind to a polypeptide comprising the alpha chain of the constant region of the murine T cell receptor (TCR) or a fragment thereof, molecules comprising these sequences and cells presenting such molecules, polynucleotides encoding such antigen binding molecules, as well as humanized forms of the antigen binding molecules; methods of using the antigen binding molecules are also disclosed.

BACKGROUND

Antigen binding molecules, including antibodies, are used in immunotherapy and solid phase-based applications such as biosensors, affinity chromatography, and immunoassays. These antibodies and antigen binding molecules gain their utility by virtue of their ability to specifically bind their targets.

SUMMARY

Disclosed herein are antigen binding molecules, including antibodies, that specifically bind a polypeptide comprising the alpha chain of the constant region of the murine T cell receptor (TCR) or a fragment thereof, molecules comprising these sequences and cells presenting such molecules. Applications and uses thereof are also disclosed.

In one aspect, the present disclosure provides an isolated antigen binding molecule that specifically binds to a polypeptide comprising the alpha chain of the constant region of a T cell receptor (TCR). In some embodiments, the TCR is a murine TCR. In some embodiments, the TCR is a chimeric TCR. In some embodiments, the TCR is a murine/human chimeric TCR.

In some embodiments, the polypeptide comprising the alpha chain of the constant region of the T cell receptor is an engineered T cell receptor. In some embodiments, the isolated antigen binding molecule is humanized. In some embodiments, the isolated antigen binding molecule is selected from the group consisting of an antibody, an scFv, a Fab, a Fab', a Fv, a F(ab')2, a dAb, a human antibody, a humanized antibody, a chimeric antibody, a monoclonal antibody, a polyclonal antibody, a recombinant antibody, an IgE antibody, an IgD antibody, an IgM antibody, an IgG1 antibody, an IgG1 antibody having at least one mutation in the hinge region, an IgG2 antibody an IgG2 antibody having at least one mutation in the hinge region, an IgG3 antibody, an IgG1 antibody having at least one mutation in the hinge region, an IgG4 antibody, an IgG4 antibody having at least one mutation in the hinge region, an antibody comprising at least one non-naturally occurring amino acid, and any combination thereof.

In some embodiments, the isolated antigen binding molecule comprises an antibody.

In some embodiments, the isolated antigen binding molecule of comprises a heavy chain (HC). In some embodiments, the isolated antigen binding molecule comprises a heavy chain CDR1 comprising SEQ ID NO: 25. In some embodiments, the isolated antigen binding molecule of comprises a heavy chain CDR2 comprising of SEQ ID NO: 26. In some embodiments, the isolated antigen binding molecule of comprises a heavy chain CDR3 comprising SEQ ID NO: 24.

In some embodiments, the isolated antigen binding molecule of comprises a HC comprising a heavy chain variable region (VH) sequence of SEQ ID NO: 1 or SEQ ID NO: 7.

In some embodiments, the isolated antigen binding molecule, comprises a VH amino acid sequence that is at least about 70%, at least about 75%, at least about 80%, at least about 85%, at least about 90%, at least about 95%, at least about 96%, at least about 97%, at least about 98%, at least about 99%, or about 100% identical to a VH of SEQ ID NO: 1 or SEQ ID NO: 7.

In some embodiments, the isolated antigen binding molecule comprises a light chain (LC). In some embodiments, the isolated antigen binding molecule comprises a light chain CDR1 comprising SEQ ID NO: 19. In some embodiments, the isolated antigen binding molecule comprises a light chain CDR2 comprising SEQ ID NO: 20. In some embodiments, the isolated antigen binding molecule comprises a light chain CDR3 comprising SEQ ID NO: 21.

In some embodiments, the isolated antigen binding molecule comprises a light chain variable region (VL) sequence comprising SEQ ID NO: 13.

In some embodiments, the isolated antigen binding molecule, comprises a VL amino acid sequence that is at least about 70%, at least about 75%, at least about 80%, at least about 85%, at least about 90%, at least about 95%, at least about 96%, at least about 97%, at least about 98%, at least about 99%, or about 100% identical to a VL of SEQ ID NO: 13.

In some embodiments, the isolated antigen binding molecule comprises (a) a VH CDR1 region comprising the amino acid sequence of SEQ ID NO: 25; (b) a VH CDR2 region comprising the amino acid sequence of SEQ ID NO: 26; (c) a VH CDR3 region comprising the amino acid sequence of SEQ ID NO: 24; (d) a VL CDR1 region comprising the amino acid sequence of SEQ ID NO: 19; (e) a VL CDR2 region comprising the amino acid sequence of SEQ ID NO: 20; and (f) a VL CDR3 region comprising the amino acid sequence of SEQ ID NO: 21.

In some embodiments, the isolated antigen binding molecule comprises (a) a VH comprising the amino acid sequence of SEQ ID NO: 1; and (b) a VL comprising the amino acid sequence of SEQ ID NO: 13.

In some embodiments, the isolated antigen binding molecule comprises (a) a heavy chain comprising the amino acid sequence of SEQ ID NO: 5; and (b) a light chain comprising the amino acid sequence of SEQ ID NO: 17.

In some embodiments, the isolated antigen binding molecule comprises (a) a VH comprising the amino acid sequence of SEQ ID NO: 7; and (b) a VL comprising the amino acid sequence of SEQ ID NO: 13.

In some embodiments, the isolated antigen binding molecule comprises (a) a heavy chain comprising the amino acid sequence of SEQ ID NO: 11; and (b) a light chain comprising the amino acid sequence of SEQ ID NO: 17.

In some embodiments, the isolated antigen binding molecule comprises further comprising a detectable label. In some embodiments, the detectable label is selected from the group consisting of a fluorescent label, a photochromic compound, a proteinaceous fluorescent label, a magnetic label, a radiolabel, and a hapten. In some embodiments, the detectable label is a fluorescent label selected from the group consisting of an Atto dye, an Alexafluor dye, quantum dots, Hydroxycoumarin, Aminocouramin, Methoxycourmarin, Cascade Blue, Pacific Blue, Pacific Orange, Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyanl, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry.

In some embodiments, the present disclosure provides a composition comprising any one of the isolated antigen binding molecules described herein. In one aspect, the present disclosure provides an isolated polynucleotide encoding the heavy chain of an isolated antigen binding molecule described herein. In one aspect, the present disclosure provides an isolated polynucleotide encoding the light chain of an isolated antigen binding molecule described herein.

In one aspect, the present disclosure provides a vector comprising the isolated polynucleotide described herein.

In one aspect, the present disclosure provides an isolated cell comprising the vector described herein. In some embodiments, the isolated cell is selected from the group consisting of a CHO cell, a Sp2/0 cell, a rabbit cell and an *E. coli* cell. In one aspect, the present disclosure provides a method of making the isolated antigen binding molecule described herein, comprising incubating the cell under suitable conditions.

In one aspect, the present disclosure provides method of determining a number of cells presenting a polypeptide comprising the alpha chain of the constant region of a T cell receptor, wherein the method comprises: (a) providing a sample comprising cells known or suspected to be presenting a polypeptide comprising the alpha chain of the constant region of the T cell receptor; (b) contacting the sample with an isolated antigen binding molecule described herein under conditions that permit binding of the polypeptide and the antigen binding molecule; and (c) determining the number of cells presenting the polypeptide in the sample.

In some embodiments, the TCR is a murine TCR. In some embodiments, the TCR is a murine/human chimeric TCR.

In some embodiments, the sample is a formalin-fixed sample. In some embodiments, the sample is a formalin-fixed paraffin embedded tissue (FFPE).

In some embodiments, the method further comprises contacting the sample with an antibody to a cell surface marker. In some embodiments, the cell surface marker is selected from the group consisting of CD4, CD8 and PD-L1.

In one aspect, the present disclosure provides a method of determining the presence or absence of a polypeptide comprising the alpha chain of the constant region of a T cell receptor, wherein the method comprises: (a) providing a sample known or suspected to comprise a polypeptide comprising the alpha chain of the constant region of the T cell receptor; (b) contacting the sample with an isolated antigen binding molecule described herein under conditions that permit binding of the polypeptide and the antigen binding molecule; and (c) detecting the presence or absence of a polypeptide:antigen binding molecule complex.

In some embodiments, the TCR is a murine TCR. In some embodiments, the TCR is a murine/human chimeric TCR.

In some embodiments, the sample is a formalin-fixed sample. In some embodiments, the sample is a formalin-fixed paraffin embedded tissue (FFPE).

In some embodiments, the method further comprises contacting the sample with an antibody to a cell surface marker. In some embodiments, the cell surface marker is selected from the group consisting of CD4, CD8 and PD-L1.

BRIEF DESCRIPTION OF THE DRAWINGS

FIGS. 1A, 1B and 1C show the complementary determining region of exemplary antigen binding molecules providing herein according to Kabat, Clothia, and IMGT naming conventions, respectively. Specifically, FIG. 1A shows the following sequences QASQSVYSSNLLT (SEQ ID NO: 19), EASKLPS (SEQ ID NO: 20), LGIYDCVLADCQA (SEQ ID NO: 21), NNWIH (SEQ ID NO:22), CVSGSSGNIYYATWAK (SEQ ID NO:23), GWNL (SEQ ID NO:24); FIG. 1B shows the following sequences QASQSVYSSNLLT (SEQ ID NO: 19), EASKLPS (SEQ ID NO: 20), LGIYDCVLADCQA (SEQ ID NO: 21), GFDLGNN (SEQ ID NO: 25), SGSSG (SEQ ID NO: 26), GWNL (SEQ ID NO: 24); and FIG. 1C shows the following sequences QASQSVYSSNLLT (SEQ ID NO: 19), EASKLPS (SEQ ID NO: 20), LGIYDCVLADCQA (SEQ ID NO: 21), GFDLGNNW (SEQ ID NO: 27), VSGSSGN (SEQ ID NO: 28), ARGWNL (SEQ ID NO: 29), and NNWIH (SEQ ID NO: 22).

FIG. 2 shows a Clustal Omega sequence alignment of the heavy chain variable region sequences of exemplary antigen binding molecules clones 39-4 VH1 (SEQ ID NO: 1) and 39-4 VH3 (SEQ ID NO: 7).

Figure 3A:
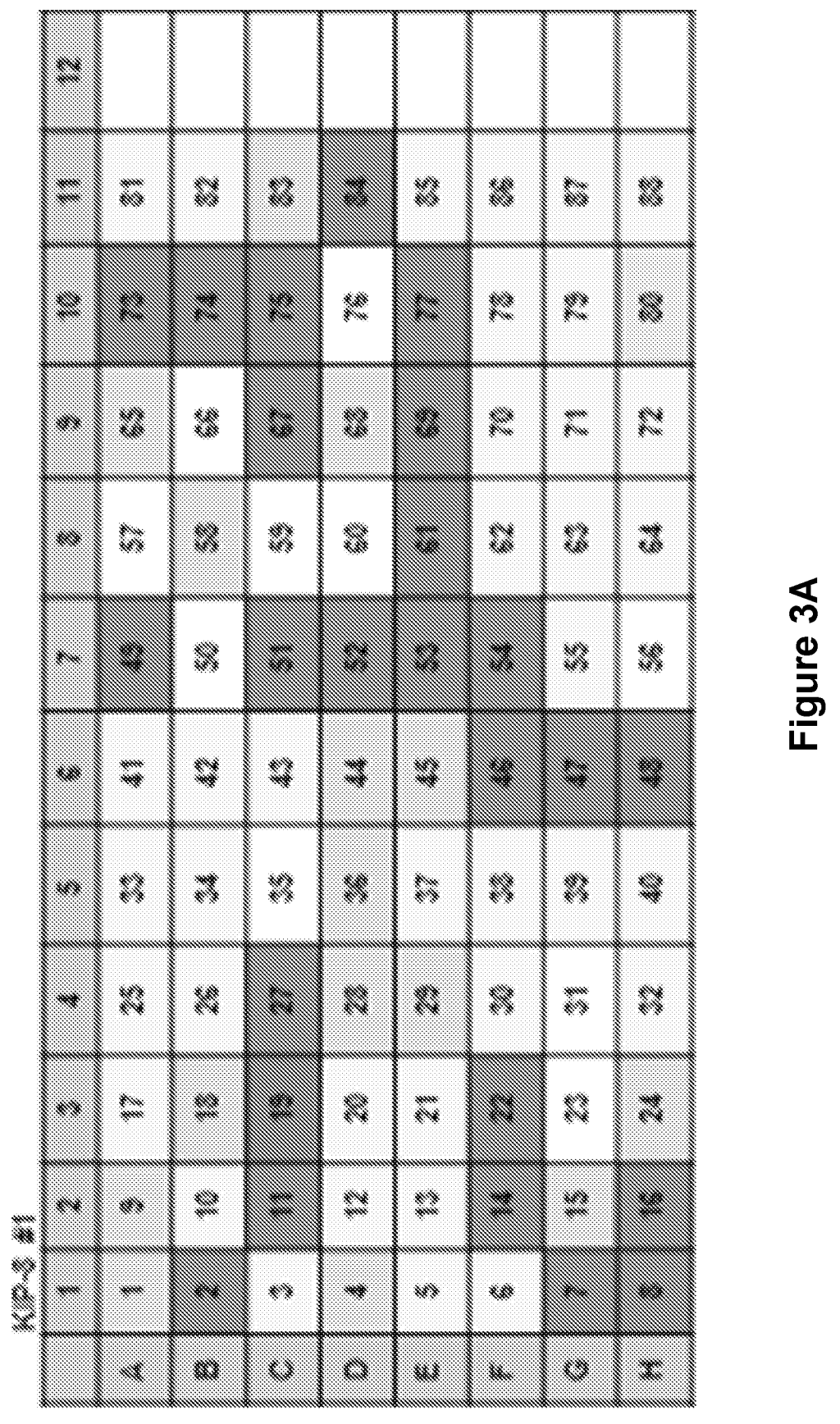

FIGS. 3A-3D show results of an ELISA screen of antibody clones generated using KIP-8A (SEQ ID NO: 31) and KIP-8B (SEQ ID NO: 32) as immunogen.

FIG. 4 shows results of an ELISA assay at different dilutions of antibody containing serum.

DETAILED DESCRIPTION

Figure 3B:
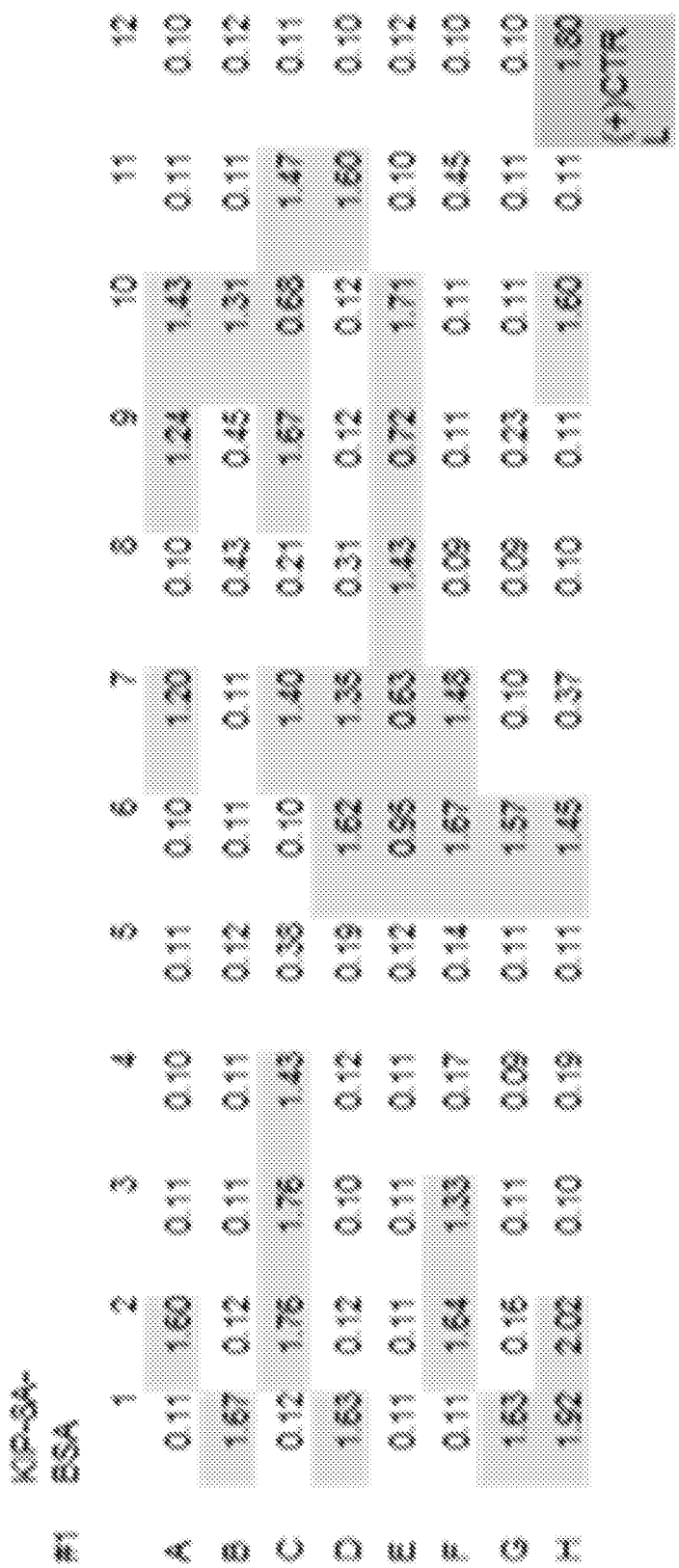
Figure 3C:
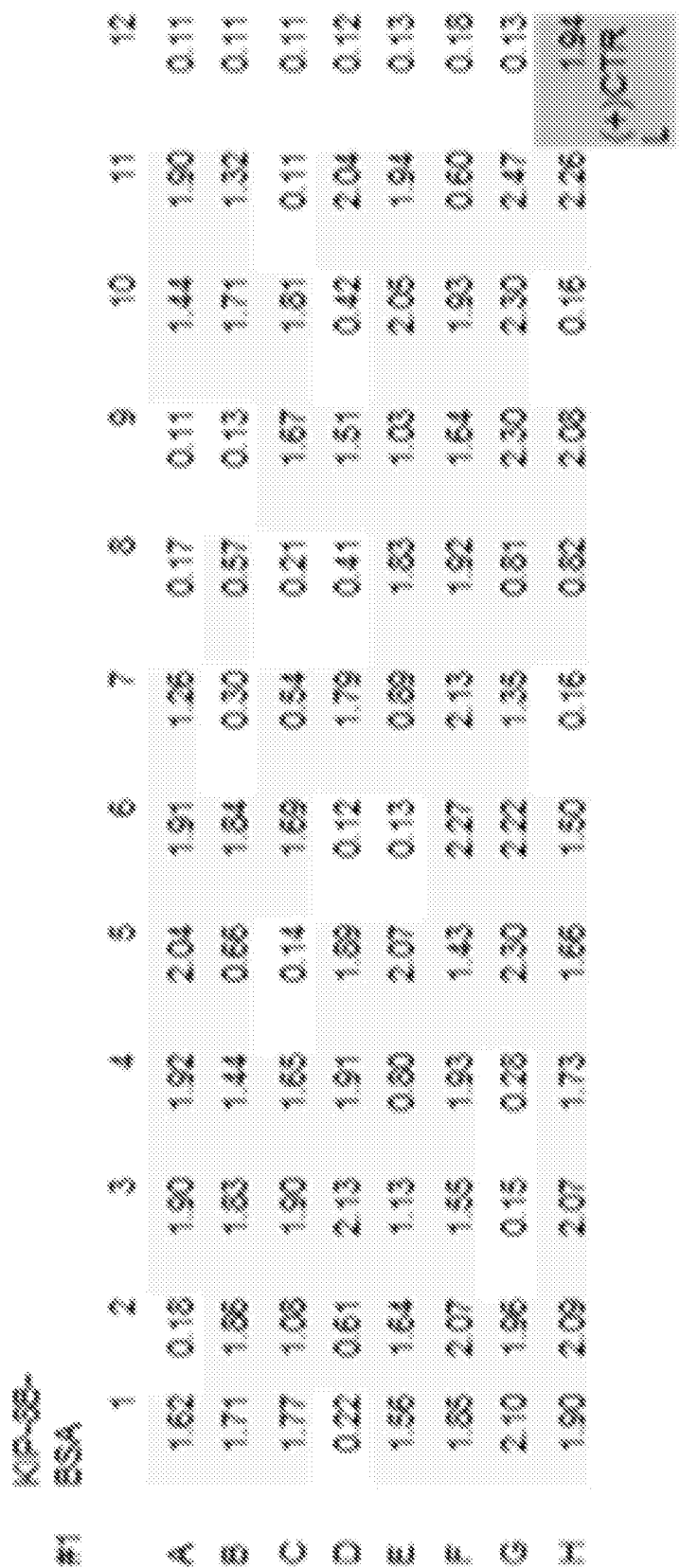
Figure 5A:
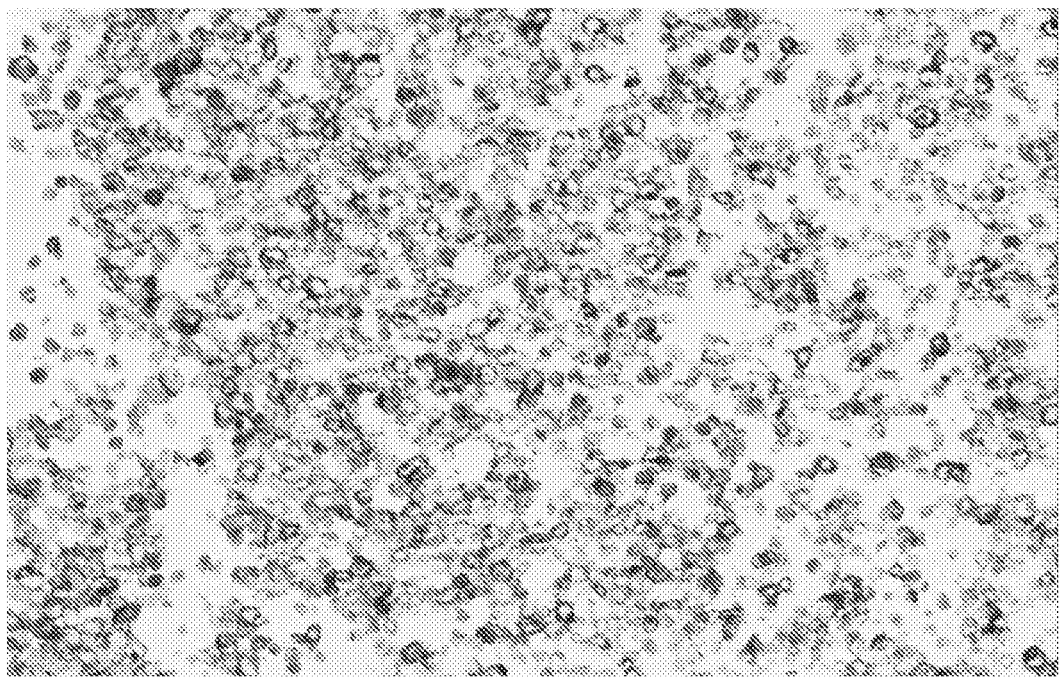
FIGS. 5A-5E show: immunohistochemistry of E7 TCR-transduced Jurkat cells (FIG. 5A), Mock-transduced Jurkat cells (FIG. 5B), MAGE TCR-transduced PBMCs (FIG. 5C), CD19 CAR-transduced PBMCs (FIG. 5D) and mouse spleen (FIG. 5E) using KIP-8 antibody which specifically binds to the alpha chain of the constant region of the murine T cell receptor (TCR).
Figure 5B:
Figure 5C:
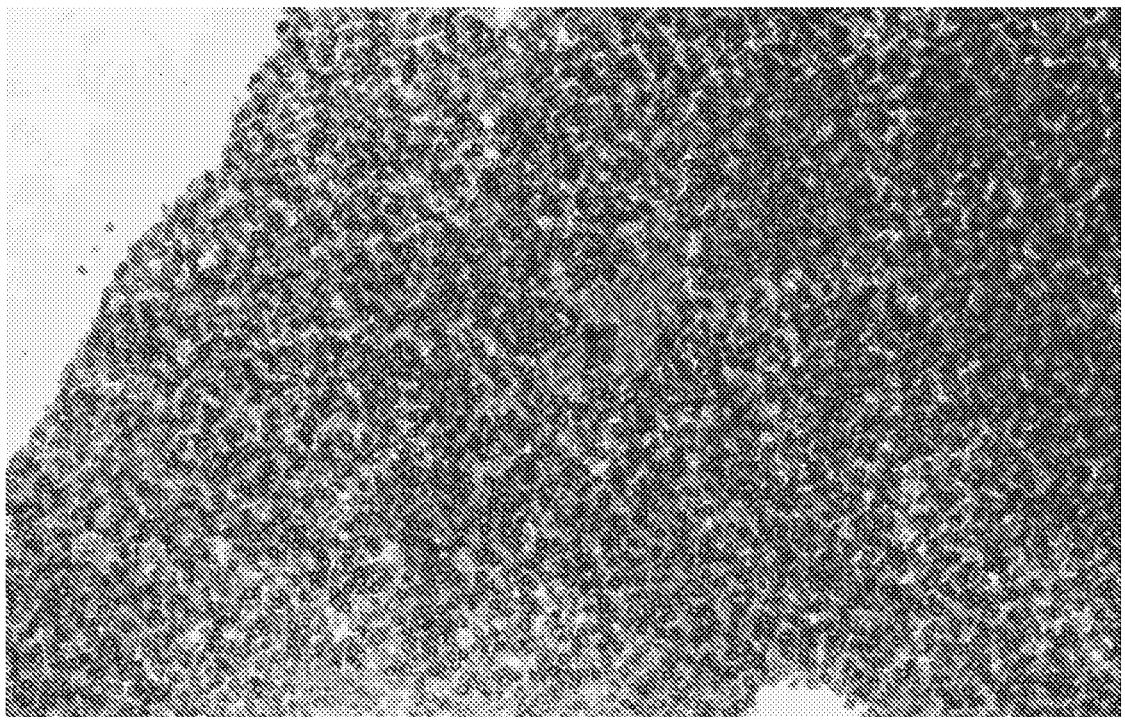
Figure 5D:
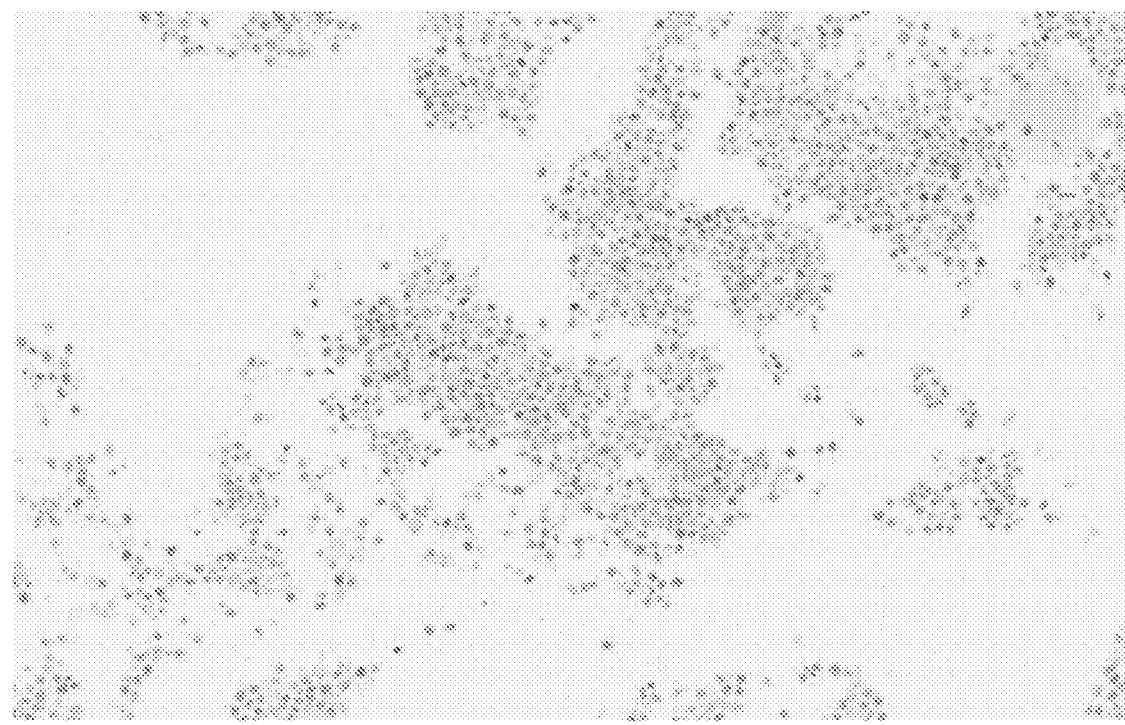
Figure 5E:
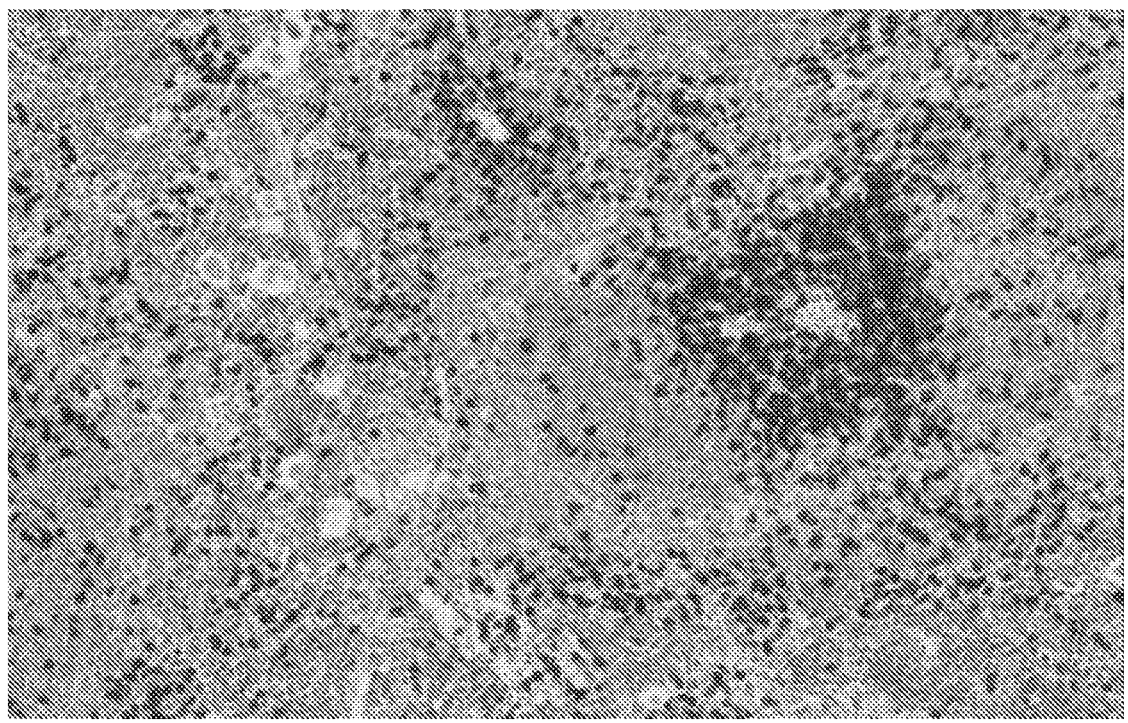

The present disclosure relates to antigen binding molecules, including antibodies, which specifically bind a polypeptide comprising the alpha chain of the constant region of a T cell receptor (TCR) or a fragment thereof, as well as humanized forms of the antigen binding molecules, polynucleotides encoding the molecules, vectors comprising the polynucleotides, in vitro cells comprising the polynucleotides and vectors and methods of use are also disclosed.

Methods of using the disclosed antigen binding molecules are provided herein. The antigen binding molecules, polynucleotides, vectors, in vitro cells and methods described herein may be used in a range of applications, e.g., as reagents to detect the presence of molecules comprising a polypeptide comprising the alpha chain of the constant region of a T cell receptor (TCR) or a fragment thereof, and cells presenting such molecules, quantifying the amount of a molecule comprising a polypeptide comprising the alpha chain of the constant region of a T cell receptor (TCR) or a fragment thereof, molecules and cells presenting such molecules, screening for molecules comprising a polypeptide comprising the alpha chain of the constant region of a T cell receptor (TCR) or a fragment thereof, and cells presenting such molecules, purifying a polypeptide comprising the alpha chain of the constant region of a T cell receptor (TCR) or a fragment thereof, and cells presenting such molecules, and biomarker studies focused on molecules comprising a polypeptide comprising the alpha chain of the constant region of a T cell receptor (TCR) or a fragment thereof. In some embodiments, the antigen binding molecules disclosed herein specifically bind to the alpha chain of a murine T cell receptor.

The antigen binding molecules (antibodies) disclosed herein were generated from hybridomas generated using B-cells of rabbit origin, but may be readily humanized using standard methods known to those of skill in the art, as well as those described herein.

I. Definitions

In order that the present disclosure may be more readily understood, certain terms are first defined. As used in this application, except as otherwise expressly provided herein, each of the following terms shall have the meaning set forth below. Additional definitions are set forth throughout the application. The headings provided herein are not limitations of the various aspects of the disclosure, which aspects may be understood by reference to the specification as a whole.

It is understood that wherever aspects are described herein with the language "comprising," otherwise analogous aspects described in terms of "consisting of" and/or "consisting essentially of" are also provided.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, *The Concise Dictionary of Biomedicine and Molecular Biology*, $2^{nd}$ ed., (2001), CRC Press; *The Dictionary of Cell & Molecular Biology*, $5^{th}$ ed., (2013), Academic Press; and *The Oxford Dictionary Of Biochemistry And Molecular Biology*, Cammack et al. eds., $2^{nd}$ ed, (2006), Oxford University Press, provide those of skill in the art with a general dictionary for many of the terms used in this disclosure.

As used herein, the twenty conventional (e.g., naturally occurring) amino acids and their abbreviations follow conventional usage. See, e.g., *Immunology—A Synthesis* (2nd Edition), Golub and Green, eds., Sinauer Assoc., Sunderland, Mass. (1991), which is incorporated herein by reference for any purpose. Stereoisomers (e.g., D-amino acids) of the twenty conventional amino acids, unnatural amino acids such as alpha-, alpha-disubstituted amino acids, N-alkyl amino acids, lactic acid, and other unconventional amino acids may also be suitable components for polypeptides of the present invention. Examples of unconventional amino acids include: 4-hydroxyproline, gamma-carboxyglutamate, epsilon-N,N,N-trimethyllysine, e-N-acetyllysine, O-phosphoserine, N-acetylserine, N-formylmethionine, 3-methylhistidine, 5-hydroxylysine, sigma-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As used herein, the term the terms "a" and "an" are used per standard convention and mean one or more, unless context dictates otherwise.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" may mean within one or more than one standard deviation per the practice in the art. Alternatively, "about" or "approximately" may mean a range of up to 10% (i.e., ±10%). For example, about 5 mg may include any number between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

As used herein, the term "and/or" is to be taken as specific disclosure of each of the two specified features or components with or without the other. Thus, the term "and/or" as used in a phrase such as "A and/or B" herein is intended to include "A and B," "A or B," "A" (alone), and "B" (alone).

Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the term the use of the alternative (e.g., "or") should be understood to mean either one, both, or any combination thereof of the alternatives.

As used herein, the term "allogeneic" refers to any material derived from one individual which is then introduced to another individual of the same species, e.g., allogeneic T cell transplantation.

As used herein, the term "antibody" (Ab) includes, without limitation, a glycoprotein immunoglobulin which binds specifically to an antigen. In general, an antibody may comprise at least two heavy (HC) chains and two light (LC) chains interconnected by disulfide bonds, or an antigen binding molecule thereof. Each HC chain comprises a heavy chain variable region (abbreviated herein as VH) and a heavy chain constant region. The heavy chain constant region comprises three constant domains, CH1, CH2 and CH3. Each LC chain comprises a light chain variable region (abbreviated herein as VL) and a light chain constant region. The light chain constant region comprises one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component of the classical complement system (C1q).

The term "antibody" also encompasses an intact immunoglobulin or an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

The term "antibody" includes, both naturally occurring and non-naturally occurring (recombinantly-produced) antibodies, human and non-human antibodies (e.g., camelid, murine, rabbit), monospecific antibodies, multispecific antibodies (including bispecific antibodies), immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies (see, e.g., Stocks, (2004) Drug Discovery Today 9(22): 960-66), antibody fusions (which term encompasses antibody-drug conjugates) and which are sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments thereof. In certain embodiments, antibodies described herein refer to polyclonal antibody populations.

A non-human antibody may be humanized using recombinant methods to reduce its immunogenicity in humans, as disclosed herein with respect to antibodies that specifically bind a polypeptide comprising the alpha chain of the constant region of the murine T cell receptor (TCR) or a fragment thereof, and cells presenting the alpha chain of the constant region of the murine T cell receptor (TCR). Where not expressly stated, and unless the context indicates otherwise, the term "antibody" also includes an antigen-binding fragment of an antigen binding molecule of any of the aforementioned immunoglobulins, and includes a monovalent and a divalent fragment or portion, and a single chain antibody (i.e., a scFv).

In various embodiments, an antibody specifically binds a polypeptide comprising the alpha chain of the constant region of the murine T cell receptor (TCR) or a fragment thereof and cells presenting such molecules. In some embodiments, the cells presenting a polypeptide comprising the alpha chain of the constant region of the murine T cell receptor (TCR) or a fragment thereof is an immune cell (e.g., a T cell).

As used herein, the term "antigen" means any molecule that provokes an immune response or is capable of being bound by an antibody or other antigen binding molecule. The immune response may involve either antibody production, or the activation of specific immunologically-competent cells, or both. Those of skill in the art will readily understand that any macromolecule, including virtually all proteins or peptides may serve as an antigen. Generally, an antigen may be endogenously expressed, i.e. expressed by genomic DNA, or it may be recombinantly expressed, or it may be chemically synthesized. In one particular embodiment, an antigen comprises all or a portion of a polypeptide comprising the alpha chain of the constant region of the murine T cell receptor (TCR) or a fragment thereof.

As used herein, the term "antigen binding molecule" means a protein comprising a portion that binds to an antigen or target protein and, optionally, a scaffold or framework portion that allows the antigen binding portion to adopt a conformation that promotes binding of the antigen binding molecule to the antigen. Examples of the representative types of antigen binding molecules include a scFv, a human, mouse or rabbit antibody; a humanized antibody; a chimeric antibody; a recombinant antibody; a single chain antibody; a diabody; a triabody; a tetrabody; a Fab fragment; a F(ab')2 fragment; an IgD antibody; an IgE antibody; an IgM antibody; an IgG1 antibody; an IgG2 anti-body; an IgG3 antibody; or an IgG4 antibody, and fragments thereof.

An antigen binding molecule may comprise, for example, an alternative protein scaffold or artificial scaffold with grafted complementarity determining regions (CDRs) or CDR derivatives. Such scaffolds include, but are not limited to, antibody-derived scaffolds comprising mutations introduced to, for example, stabilize the three-dimensional structure of the antigen binding molecule as well as wholly synthetic scaffolds comprising, for example, a biocompatible polymer. See, e.g., Korndorfer et al., 2003, *Proteins: Structure, Function, and Bioinformatics*, 53(1):121-129 (2003); Roque et al., *Biotechnol. Prog.* 20:639-654 (2004). In addition, peptide antibody mimetics ("PAMs") may be used, as well as scaffolds based on antibody mimetics utilizing various components (e.g., fibronectin) as a scaffold.

An antigen binding molecule may have, for example, the structure of a naturally occurring immunoglobulin.

An antigen binding molecule may have one or more binding sites. If there is more than one binding site, the binding sites may be identical to one another or they may be different. For example, a naturally occurring human immunoglobulin typically has two identical binding sites, while a "bispecific" or "bifunctional" antibody has two different binding sites, and is capable of specifically binding two different antigens (e.g., a polypeptide comprising the alpha chain of the constant region of the murine T cell receptor (TCR) or a fragment thereof) and a cell surface activator molecule.

In various embodiments, an antigen binding molecule is an antibody or fragment thereof, including one or more of the complementarity determining regions (CDRs) disclosed herein and shown in FIGS. 1A, 1B and 1C, which specifically bind a polypeptide comprising the alpha chain of the constant region of the murine T cell receptor (TCR) or a fragment thereof, and cells presenting such molecules. In further embodiments, the antigen binding molecule binds to a TCR comprising the a polypeptide comprising the alpha chain of the constant region of the murine T cell receptor (TCR) or a fragment thereof, and may be expressed on an immune cell, such as a T cell.

The term "autologous" refers to any material derived from the same individual to which it is later to be re-introduced. For example, the engineered autologous cell therapy (eACT™) methods described herein involve collection of lymphocytes from a patient, which are then engineered to express a construct, e.g., a TCR construct, and then administered back to the same patient.

As used herein, the term "binding affinity" means the strength of the sum total of non-covalent interactions between a single binding site of a molecule (e.g., an antigen binding molecule such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y may generally be represented by the dissociation constant ($K_D$). Affinity may be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody-antigen complex. The $k_{on}$ and $k_{off}$ may be determined by standard techniques known to one of ordinary skill in the art, such as BIAcore® or KinExA or surface plasmon resonance.

As used herein, the term "complementarity determining region" or "CDR" means an amino acid sequence that contributes to antigen binding specificity and affinity. Framework regions can aid in maintaining the proper confirmation of the CDRs to promote binding between the antigen binding molecule and an antigen. There are three CDRs in each of the variable regions of the heavy chain and the light chain, which are designated CDR1, CDR2 and CDR3, for each of the variable regions. The exact boundaries of CDRs have been defined differently according to different systems.

A number of definitions of the CDRs are commonly in use: Kabat numbering, Chothia numbering, AbM numbering, or contact numbering. The AbM definition is a compromise between the Kabat and Chothia systems, and is used by Oxford Molecular's AbM antibody modelling software.

The system described by Kabat (Kabat et al., Sequences of Proteins of Immunological Interest (National Institutes of Health, Bethesda, Md. (1987) and (1991)) provides a residue numbering system applicable to any variable region of an antibody, and also provides precise residue boundaries defining the three CDRs.

Chothia and coworkers (Chothia and Lesk, (1987) *J. Mol. Biol.,* 196:901-917; and Chothia et al., (1989) *Nature,* 342:877-883) found that certain sub-portions within Kabat CDRs adopt nearly identical peptide backbone conformations, despite having great diversity at the level of amino acid sequence. Chothia CDRs have boundaries that overlap with Kabat CDRs. Other boundaries defining CDRs overlapping with the Kabat CDRs have been described by Padlan et al. ((1995) *FASEB J.,* 9:133-139) and MacCallum et al. ((1996) *J. Mol. Biol.,* 262(5):732-745). Still other CDR boundary definitions may not strictly follow one of the described systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although exemplary embodiments use Chothia defined CDRs.

Table A defines CDRs using each numbering system. The contact definition is based on an analysis of the available complex crystal structures.

TABLE A

| Loop | Kabat | AbM | Chothia | Contact |
| --- | --- | --- | --- | --- |
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B | H26--H35B | H26--H32 . . . 34 | H30--H35B |
| H1 | H31--H35 | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen binding molecule thereof. In certain aspects, the CDRs of an antibody may be determined according to the Kabat numbering system (see, e.g., Kabat et al. in Sequences of *Proteins of Immunological Interest,* 5th Ed., NIH Publication 91-3242, Bethesda Md. 1991). Using the Kabat numbering system, CDRs within an antibody heavy chain molecule are typically present at amino acid positions 31 to 35, which optionally may include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein may be described according to the Kabat numbering scheme although they may readily be construed in other numbering systems using Table A.

In certain aspects, the CDRs of an antibody may be determined according to the Chothia numbering scheme, which refers to the location of immunoglobulin structural loops (see, e.g., Chothia C & Lesk A M, (1987), *J Mol Biol* 196: 901-917; Al-Lazikani B et al., (1997) *J Mol Biol* 273: 927-948; Chothia C et al., (1992) *J Mol Biol* 227: 799-817; Tramontano A et al., (1990) *J Mol Biol* 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). See Table A. In a specific embodiment, the CDRs of the antibodies described herein have been determined according to the Chothia numbering scheme, as shown in FIG. 1A.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen binding molecule provided herein (or fragment thereof) may be replaced with an amino acid residue with a similar side chain.

Conservative amino acid substitutions, which are encompassed by the present disclosure, may encompass non-naturally occurring amino acid residues, which are typically incorporated by chemical peptide synthesis rather than by synthesis in biological systems. These include peptidomimetics and other reversed or inverted forms of amino acid moieties. Naturally occurring residues may be divided into classes based on common side chain properties:

hydrophobic: norleucine, Met, Ala, Val, Leu, Ile;

neutral hydrophilic: Cys, Ser, Thr, Asn, Gln;

acidic: Asp, Glu;

basic: His, Lys, Arg;

residues that influence chain orientation: Gly, Pro; and aromatic: Trp, Tyr, Phe.

Non-conservative substitutions may involve the exchange of a member of one of these classes for a member from another class. Such substituted residues may be introduced, for example, into regions of a human antibody that are homologous with non-human antibodies, or into the non-homologous regions of the molecule. Exemplary conservative amino acid substitutions are set forth in Table B below.

TABLE B

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which may exhibit various effector functions, such as interaction with the Fc receptor. The constant region of an immunoglobulin molecule generally has a more conserved amino acid sequence relative to an immunoglobulin variable domain.

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding molecule (a derivative) may have a greater circulating half-life than an antigen binding molecule that is not chemically modified. In some embodiments, a derivative antigen binding molecule is covalently modified to include one or more water soluble polymer attachments, including, but not limited to, polyethylene glycol, polyoxyethylene glycol, or polypropylene glycol.

As used herein, the term "diabody" or dAB means bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., (1993) *Proc Natl Acad Sci U.S.A.* 90:6444-48, Poljak et al., (1994) *Structure* 2: 1121-23, and Perisic et al., (1994) *Structure* 2(12): 1217-26). If the two polypeptide chains of a diabody are identical, then a diabody resulting from their pairing will have two identical antigen binding sites. Polypeptide chains having different sequences may be used to make a diabody with two different antigen binding sites. Similarly, tribodies and tetrabodies are antibodies comprising three and four polypeptide chains, respectively, and forming three and four antigen binding sites, respectively, which may be the same or different.

As used herein, an "epitope" is a term in the art and refers to a localized region of an antigen to which an antibody may specifically bind. An epitope may be, for example, contiguous amino acids of a polypeptide (linear or contiguous epitope) or an epitope may, for example, come together from two or more non-contiguous regions of a polypeptide or polypeptides (conformational, non-linear, discontinuous, or non-contiguous epitope). In certain embodiments, the epitope to which an antibody binds may be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping).

As used herein, the term "Fab fragment" means is a monovalent fragment having the VL, VH, CL and CH1 domains; a "F(ab')$_2$ fragment" is a bivalent fragment having two Fab fragments linked by a disulfide bridge at the hinge region; a "Fv fragment" has the VH and VL domains of a single arm of an antibody; and a "dAb fragment" has a VH domain, a VL domain, or an antigen-binding fragment of a VH or VL domain.

As used herein, the terms "immunospecifically binds," "immunospecifically recognizes," "specifically binds," and "specifically recognizes" are analogous terms and are used interchangeably in the context of antigen binding molecules, and means that a given molecule preferentially binds to an antigen (e.g., epitope or immune complex) as such binding is understood by one skilled in the art.

In some embodiments, molecules that specifically bind to an antigen (e.g., a polypeptide comprising the alpha chain of the constant region of the murine T cell receptor (TCR) or a fragment thereof and cells presenting such molecules) do not cross react with other proteins under similar binding conditions. In some embodiments, provided herein is an antibody or fragment thereof that binds to a polypeptide comprising the alpha chain of the constant region of the murine T cell receptor (TCR) or a fragment thereof and cells presenting such molecules, with higher affinity than to another unrelated antigen.

As used herein, the term "heavy chain" when used in reference to an antibody may refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "immunoglobulin" means an immune molecule from any of the commonly known isotypes, including but not limited to IgA, secretory IgA, IgG and IgM. IgG subclasses are also well known to those in the art and include but are not limited to human IgG1, IgG2, IgG3 and IgG4. Many of the molecules described herein are immunoglobulins. As used herein, "isotype" means the antibody class or subclass (e.g., IgM or IgG1) that is encoded by the heavy chain constant region genes.

An immunoglobulin is a tetrameric molecule, normally composed of two identical pairs of polypeptide chains, each pair having one "light" (about 25 kDa) and one "heavy" chain (about 50-70 kDa). The amino-terminal portion of each chain includes a variable region of about 100 to 130 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, or IgE, respectively. Within light and heavy chains, the variable and constant regions are joined by a "J" region of about 12 or more amino acids, with the heavy chain also including a "D" region of about 10 more amino acids. See generally, Berzofsky & Berkower, in *Fundamental Immunology* (Paul, (ed), Lippincott Williams & Wilkins (2012); which chapter and volume is incorporated by reference in its entirety for all purposes). The variable regions of each light/heavy chain pair form the antibody binding site such that an intact immunoglobulin has two primary binding sites.

Naturally occurring immunoglobulin chains exhibit the same general structure of relatively conserved framework regions (FR) joined by three hypervariable regions, also called complementarity determining regions or "CDRs." From N-terminus to C-terminus, both light and heavy chains comprise the domains FR1, CDR1, FR2, CDR2, FR3, CDR3 and FR4. The assignment of amino acids to each domain may be done in accordance with the definitions of Kabat (see, e.g., Kabat et al. in *Sequences of Proteins of Immunological Interest*, 5th Ed., *NIH* Publication 91-3242, Bethesda Md. (1991)) or Chothia (Chothia, used herein, (see, e.g., Chothia & Lesk (1987), *J. Mol. Biol.* 196:901-917; Chothia et al., 1989, *Nature* 342:878-883 or Honegger & Pluckthun (2001), *J Mol Biol* 309:657-670). The Kabat, Chothia and Abm (Oxford Molecular) numbering systems are described more fully herein.

As used herein, the term "in vitro cell" refers to any cell that is cultured ex vivo. An in vitro cell may include a human cell such as a T cell or dendritic cell, or it may include CHO, sP2/0, rabbit and other non-human cells.

As used herein, the term "light chain" when used in reference to an antibody may refer to any distinct type, e.g., kappa (κ) or lambda (λ) based on the amino acid sequence of the constant domains. Light chain amino acid sequences are known in the art. In specific embodiments, the light chain is a human light chain.

The term "neutralizing" refers to an antigen binding molecule, scFv, antibody, or a fragment thereof, that binds to a ligand (e.g., a polypeptide comprising the alpha chain of the constant region of the murine T cell receptor (TCR) or a fragment thereof) and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

As used herein, the terms "peptide," "polypeptide," and "protein" are used interchangeably herein, and mean a compound comprising amino acid residues covalently linked by peptide bonds. A polypeptide, protein or peptide must contain at least two amino acids, but no limitation is placed on the maximum number of amino acids that may comprise a protein's or peptide's amino acid sequence. As used herein, the term refers to both short chains, which also commonly are referred to as peptides, oligopeptides and oligomers, and to longer chains, which generally are referred to as proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The term "polypeptide"

includes natural peptides, recombinant peptides, synthetic peptides, or a combination thereof.

In some aspects, the polypeptides and/or proteins have deletions from, additions to, and/or substitutions of one or more amino acids of antigen binding molecule. Useful polypeptide fragments may include immunologically functional fragments of antigen binding molecules, including not limited to one or more CDR regions, variable domains of a heavy and/or light chain, a portion of other portions of an antibody chain, and the like. Moieties that may be substituted for one or more amino acids of an antigen binding molecule include, e.g., D or L forms of amino acids, an amino acid different from the amino acid normally found in the same position of an antigen binding molecule, deletions, non-naturally occurring amino acids, and chemical analogs of amino acids.

Peptide analogs are commonly used in the pharmaceutical industry as non-peptide drugs with properties analogous to those of the template peptide and form an aspect of the instant disclosure. These types of non-peptide compound are termed "peptide mimetics" or "peptidomimetics." See, e.g., Fauchere, (1986) *Adv. Drug Res.* (Testa, ed.) 15:29-69; Veber & Freidinger, (1985) *TINS*, p. 392; and Evans et al., (1987) *J. Med. Chem*, 30:1229-39, which are incorporated herein by reference for any purpose.

Polypeptides, peptides, proteins and analogous molecules comprising a polypeptide comprising the alpha chain of the constant region of the murine T cell receptor (TCR) or a fragment thereof, molecules comprising these sequences and cells presenting such molecules, are specifically encompassed by the terms.

As used herein, the term "percent identity" means the percent of identical residues between the amino acids or nucleotides in the compared molecules. For these calculations, gaps in alignments (if any) must be addressed by a particular mathematical model or computer program (i.e., an "algorithm"). Methods that may be used to calculate the identity of the aligned nucleic acids or polypeptides include those described in *Computational Molecular Biology*, (Lesk, ed.), (1988) New York: Oxford University Press; *Biocomputing Informatics and Genome Projects*, (Smith, ed.), 1993, New York: Academic Press; *Computer Analysis of Sequence Data, Part I*, (Griffin and Griffin, eds.), 1994, New Jersey: Humana Press; von Heinje, (1987) *Sequence Analysis in Molecular Biology*, New York: Academic Press; *Sequence Analysis Primer*, (Gribskov and Devereux, eds.), 1991, New York: M. Stockton Press; and Carillo et al., (1988) *J. Applied Math.* 48:1073.

In calculating percent identity, the sequences being compared are aligned in a way that gives the largest match between the sequences. The computer program used to determine percent identity may be, e.g., MOE (Chemical Computing Group) or DNASTAR (University of Wisconsin, Madison, Wis.). The computer algorithm GAP may be used to align the two polypeptides or polynucleotides for which the percent sequence identity is to be determined. The sequences are aligned for optimal matching of their respective amino acid or nucleotide (the "matched span," as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, e.g., Dayhoff et al., (1978) *Atlas of Protein Sequence and Structure* 5:345-352 for the PAM 250 comparison matrix; Henikoff et al., (1992) *Proc. Natl. Acad. Sci. U.S.A.* 89: 10915-10919 for the BLOSUM 62 comparison matrix) is also used by the algorithm.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (e.g., the GAP program) may be adjusted if desired to result in an alignment that spans at least 50 contiguous amino acids of the target polypeptide.

As used herein, the terms "single-chain antibody" and "single chain fragment variable (scFv)" are used interchangeably and mean an antigen binding molecule in which a VL and a VH region are joined via a linker to form a continuous protein chain wherein the linker is long enough to allow the protein chain to fold back on itself and form a monovalent antigen binding site (see, e.g., Bird et al., (1988) *Science* 242:423-26 and Huston et al., (1988) *Proc. Natl. Acad. Sci. U.S.A.* 85:5879-83 (1988). FMC63 (Nicholson et al., (1997) *Mol. Immunol.* 34:(16-17) 1157-65) is a specific example of a scFv, and is specific for CD19.

The terms "transduction" and "transduced" refer to the process whereby foreign DNA is introduced into a cell via viral vector (see Hartl and Jones (1997) *Genetics: Principles and Analysis*, $4^{th}$ ed, Jones & Bartlett). In some embodiments, the vector is a retroviral vector, a DNA vector, a RNA vector, an adenoviral vector, a baculoviral vector, an Epstein Barr viral vector, a papoviral vector, a vaccinia viral vector, a herpes simplex viral vector, an adenovirus associated vector, a lentiviral vector, or any combination thereof.

As used herein, the terms "variable region" or "variable domain" are used interchangeably and mean a portion of an antibody, generally, a portion of a light or heavy chain, typically the amino-terminal end of the antibody, and comprising about 100-130 amino acids in the heavy chain and about 90 to 115 amino acids in the light chain, which differ extensively in sequence among antibodies and are used in the binding and specificity of a particular antibody for a particular antigen. The variability in sequence is concentrated in those regions called complementarity determining regions (CDRs) while the more highly conserved regions in the variable domain are called framework regions (FR). The CDRs of the light and heavy chains are primarily responsible for the interaction and specificity of the antibody with antigen.

In certain embodiments, the variable region of an antigen binding molecule is a human variable region. In further embodiments, the variable region comprises rodent, human or murine CDRs and human framework regions (FRs). In further embodiments, the variable region is a primate (e.g., a non-human primate) variable region. In yet further embodiments, the variable region is a rabbit variable region. In other embodiments, the variable region comprises human CDRs and non-human (e.g., rabbit, murine, rat or non-human primate) framework regions (FRs). In other embodiments, the variable region comprises non-human (e.g., rabbit, murine, rat or non-human primate) CDRs and human framework regions (FRs).

The terms "VH," "VH domain" and "VH chain" are used interchangeably and mean the heavy chain variable region of an antigen binding molecule, antibody or an antigen binding fragment thereof.

The terms "VL," "VL domain" and "VL chain" are used interchangeably and mean the light chain variable region of an antigen binding molecule, antibody or an antigen binding fragment thereof.

Various aspects of the invention are described in further detail in the following subsections.

II. Antigen Binding Molecules and Polynucleotides Encoding the Same

The present disclosure is directed to antigen binding molecules, including antibodies, that specifically bind a polypeptide comprising the alpha chain of the constant region of the murine T cell receptor (TCR) or a fragment thereof and cells presenting such molecules, and/or antigen binding molecules which cross compete with one or more antigen binding molecules described herein (i.e., one or more of those described in FIG. 2 and/or disclosed in the appended Sequence Listing). Polynucleotides encoding the antigen binding molecules are also provided, and form an aspect of the instant disclosure.

An antibody or antigen binding molecule encoded of the present invention may be single chained or double chained. In some embodiments, the antibody or antigen binding molecule is single chained. In some embodiments, the antigen binding molecule is selected from the group consisting of an scFv, a Fab, a Fab', a Fv, a F(ab')$_2$, a dAb, and any combination thereof.

In certain embodiments, an antigen binding molecule such as an antibody comprises a single chain, wherein the heavy chain variable region and the light chain variable region are connected by a linker (an scFv). In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids. In some embodiments, the linker comprises between about 8 amino acids and about 18 amino acids (e.g., 10 amino acids).

In some embodiments, the antigen binding molecules of the present disclosure are antibodies and antigen binding fragments thereof. In one embodiment, the antibodies of the present disclosure comprise at least one CDR set forth in FIG. 1A, 1B or 1C. In another aspect, the present disclosure provides hybridomas capable of producing the antibodies disclosed herein and methods of producing antibodies from hybridomas, as described herein and as known in the art.

Humanized antibodies are described herein and may be prepared by known techniques. In one embodiment, a humanized monoclonal antibody comprises the variable domain of a murine or rabbit antibody (or all or part of the antigen binding site thereof) and a constant domain derived from a human antibody. Alternatively, a humanized antibody fragment may comprise an antigen binding site of a murine or rabbit monoclonal antibody and a variable domain fragment (lacking the antigen binding site) derived from a human antibody. Procedures for the production of engineered monoclonal antibodies include those described in Riechmann et al., (1988) *Nature* 332:323, Liu et al., (1987) *Proc. Nat. Acad. Sci. USA* 84:3439, Larrick et al., (1989) *Bio/Technology* 7:934, and Winter et al., (1993) *TIPS* 14:139. In one embodiment, the chimeric antibody is a CDR grafted antibody. Techniques for humanizing antibodies are discussed in, e.g., U.S. Pat. Nos. 5,869,619; 5,225,539; 5,821,337; 5,859,205; 6,881,557; Padlan et al., (1995) *FASEB J.* 9:133-39; Tamura et al., (2000) *J. Immunol.* 164:1432-41; Zhang et al., (2005) *Mol. Immunol.* 42(12): 1445-1451; Hwang et al., *Methods*. (2005) 36(1):35-42; Dall'Acqua et al., (2005) *Methods* 36(1):43-60; and Clark, (2000) *Immunology Today* 21(8):397-402.

An antigen binding molecule of the present invention may also be a fully human monoclonal antibody. Fully human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

Procedures have been developed for generating human monoclonal antibodies in non-human animals. For example, mice in which one or more endogenous immunoglobulin genes have been inactivated by various means have been prepared. Human immunoglobulin genes have been introduced into the mice to replace the inactivated mouse genes. In this technique, elements of the human heavy and light chain locus are introduced into strains of mice derived from embryonic stem cell lines that contain targeted disruptions of the endogenous heavy chain and light chain loci (see also Bruggemann et al., (1997) *Curr. Opin. Biotechnol.* 8:455-58).

Examples of techniques for production and use of transgenic animals for the production of human or partially human antibodies are described in U.S. Pat. Nos. 5,814,318, 5,569,825, and 5,545,806; Davis et al., *Antibody Engineering: Methods and Protocols*, (Lo, ed) Humana Press, NJ, 191-200 (2003); Kellermann et al., (2002) *Curr Opin Biotechnol.* 13:593-97; Russel et al., (2000) *Infect Immun.* 68:1820-26; Gallo et al., (2000) *Eur J. Immun.* 30:534-40; Davis et al., (1999) *Cancer Metastasis Rev.* 18:421-25; Green, (1999) *J Immunol Methods* 231:11-23; Jakobovits, (1998) *Advanced Drug Delivery Reviews* 31:33-42; Green et al., (1998) *J Exp Med.* 188:483-95; Jakobovits, (1998) *Exp. Opin. Invest. Drugs.* 7:607-14; Tsuda et al., (1997) *Genomics,* 42:413-21; Mendez et al., (1997) *Nat. Genet.* 15:146-56; Jakobovits, (1994) *Curr Biol.* 4:761-63; Arbones et al., (1994) *Immunity* 1:247-60; Green et al., (1994) *Nat. Genet.* 7:13-21; Jakobovits et al., (1993) *Nature* 362:255-58; Jakobovits et al., (1993) *Proc Natl Acad Sci USA* 90:2551-55; Chen et al., (1993) *Intl Immunol* 5:647-656; Choi et al., (1993) *Nature Genetics* 4:117-23; Fishwild et al., (1996) *Nature Biotechnology* 14:845-51; Lonberg et al., (1994) *Nature* 368: 856-59; Lonberg, (1994) *Handbook of Experimental Pharmacology* 113: 49-101; Neuberger, (1996) *Nature Biotech* 14:826; Taylor et al., (1992) *Nucleic Acids Research* 20:6287-95; Taylor et al., (1994) *Intl Immunol* 6:579-91; Tomizuka et al., (1997) *Nature Genetics* 16:133-43; Tomizuka et al., (2000) *Proc Nat Acad Sci USA* 97:722-27; Tuaillon et al., (1993) *Proc Nat Acad Sci USA* 90:3720-24; Tuaillon et al., (1994) *J Immunol* 152:2912-20; Lonberg et al., (1994) *Nature* 368:856; Taylor et al., (1994) *Intl Immunol* 6:579; U.S. Pat. No. 5,877,397; Bruggemann et al., (1997) *Curr. Opin. Biotechnol.* 8:455-58; Jakobovits et al., (1995) *Ann. N.Y. Acad. Sci.* 764:525-35.

An additional method for obtaining antigen binding molecules of the invention is by the use of phage display, which is well-established for this purpose. See, e.g., Winter et al., (1994) *Ann. Rev. Immunol.* 12:433-55; Burton et al., (1994) *Adv. Immunol* 57:191-280. Human or murine immunoglobulin variable region gene combinatorial libraries may be created in phage vectors that may be screened to select Ig fragments (Fab, Fv, sFv, or multimers thereof) that bind the scFv FMC63, as well as molecules comprising this sequence and cells presenting such molecules. See, e.g., U.S. Pat. No. 5,223,409; Huse et al., (1989) *Science* 246:1275-81; Sastry et al., (1989) *Proc. Natl. Acad. Sci. USA* 86:5728-32; Alting-Mees et al., (1990) *Strategies in Molecular Biology* 3:1-9; Kang et al., (1991) *Proc. Natl. Acad. Sci. USA* 88:4363-66; Hoogenboom et al., (1992) *J. Mol. Biol.* 227:381-388; Schlebusch et al., (1997) *Hybridoma* 16:47-52 and references cited therein. For example, a library containing a plurality of polynucleotide sequences encoding Ig variable region fragments may be inserted into the genome of a filamentous bacteriophage, such as M13 or lambda phage (λImmunoZap™(H) and λImmunoZap™(L) vectors (Stratagene, La Jolla, Calif.) may also be used in this approach) or a variant thereof, in frame with the sequence encoding a phage coat protein.

Briefly, mRNA is isolated from a B-cell population, and used to create heavy and light chain immunoglobulin cDNA expression libraries in the λImmunoZap™(H) and λImmunoZap™(L) and similar vectors. These vectors may be screened individually or co-expressed to form Fab fragments or antibodies. Positive plaques may subsequently be converted to a non-lytic plasmid that allows high level expression of monoclonal antibody fragments from *E. coli.*

In one embodiment, in a hybridoma the variable regions of a gene expressing a monoclonal antibody of interest are amplified using nucleotide primers. These primers may be synthesized by one of ordinary skill in the art, or may be purchased from commercial sources, which also sell primers for mouse and human variable regions including, among others, primers for $V_H$, $V_L$, $C_H$ and $C_L$ regions). These primers may be used to amplify heavy or light chain variable regions, which may then be inserted into vectors. These vectors may then be introduced into *E. coli*, yeast, or mammalian-based systems for expression. Large amounts of a single-chain protein containing a fusion of the $V_H$ and $V_L$ domains may be produced using these methods.

Once cells producing the antigen binding molecules provided herein have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

It will be understood by those of skill in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in, e.g., Harris, (1995) *J Chromatog* 705:129-34).

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies may be isolated and purified by a variety of well-established techniques. Such isolation techniques include affinity chromatography with Protein-A Sepharose, size-exclusion chromatography, and ion-exchange chromatography (see, e.g., Baines and Thorpe, (1992) in *Methods in Molecular Biology,* 10:79-104 (The Humana Press). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anti-constant region (light chain or heavy chain) antibody, and an anti-idiotype antibody.

Although the disclosed antigen binding molecules were produced in a rabbit system, human, partially human, or humanized antibodies may be suitable for many applications. Such antibodies may be prepared as described herein and form an aspect of the instant disclosure.

In some embodiments, an antigen binding molecule of the instant disclosure is an antibody identified herein as KIP-8 which may refer to Clone 39-4 vh1 or Clone 39-4 vh3 and each comprises the following heavy and light chain amino acid, coding, variable, and CDR sequences (according to Clothia), as provided and labeled. Clone-39-4 VH1 and VH3 have identical CDRs, the single amino acid change is located N-terminal of CDR H1 as shown in FIG. 2.

In some embodiments, the antigen binding molecules of the present invention specifically bind to a polypeptide comprising the alpha chain of the constant region of the murine T cell receptor (TCR) or a fragment thereof and cells presenting such molecules. In some embodiments, the antigen binding molecules of the present invention comprise heavy chain and light chain sequences according to SEQ ID NOs: 33-52. In specific embodiments, an antigen binding molecule of the instant disclosure is an antibody identified herein as Clone 39-vh1 and Clone 39-vh3—sharing a common light chain sequence and heavy chain CDR sequences—and each comprises the following heavy and light chain amino acid, coding, variable, and CDR sequences (according to Clothia), as provided and labeled below:

```
IIa. Clone 39 Light Chain
Clone 39 LC DNA coding sequence
                                  (SEQ ID NO: 18)
ATGGACACGAGGGCCCCCACTCAGCTGCTGGGGCTCCTGCTGCTCTGGCTC

CCAGGTGCCACATTTGCCCAAGTGCTGACCCAGACTCCAGCCTCGGTGTCT

GCAGCTGTGGGAGGCACAGTCACCATCAACTGCCAGGCCAGTCAGAGTGTT

TATAGCAGCAACCTCTTAACCTGGTATCAGAAGAAACCAGGGCAGCCTCCC

AAGCTCCTGATCTACGAAGCATCCAAACTGCCATCTGGGATCCCATCGCGC

TTCAGCGGCAGTGGATCTGGGACACAGTTCACTCTCACCATCAGCGACGTA

CAGTGTGCCGATGCTGCCACTTACTACTGTCTAGGCATTTATGATTGTGTG

CTTGCTGATTGTCAGGCTTTCGGCGGAGGGACCGAAGTGGTGGTCAAAGGT

GATCCAGTTGCACCTACTGTCCTCATCTTCCCACCAGCTGCTGATCAGGTG

GCAACTGGAACAGTCACCATCGTGTGTGTGGCGAATAAATACTTTCCCGAT
```

-continued

```
GTCACCGTCACCTGGGAGGTGGATGGCACCACCCAAACAACTGGCATCGAG

AACAGTAAAACACCGCAGAATTCTGCAGATTGTACCTACAACCTCAGCAGC

ACTCTGACACTGACCAGCACACAGTACAACAGCCACAAAGAGTACACCTGC

AAGGTGACCCAGGGCACGACCTCAGTCGTCCAGAGCTTCAATAGGGGTGAC

TGTTAG
```

LC variable region AA  
(SEQ ID NO: 13)  
MDTRAPTQLLGLLLLWLPGATFAQVLTQTPASVSAAVGGTVTINC<u>QASQSV</u>
<u>YSSNLLT</u>WYQKKPGQPPKLLIY<u>EASKLPS</u>GIPSRFSGSGSGTQFTLTISDV
QCADAATYYC<u>LGIYDCVLADCQA</u>FGGGTEVVVK

LC CDR1  
(SEQ ID NO: 19)  
QASQSVYSSNLLT

LC CDR2  
(SEQ ID NO: 20)  
EASKLPS

LC CDR3  
(SEQ ID NO: 21)  
LGIYDCVLADCQA

HC CDR1  
(SEQ ID NO: 25)  
GFDLGNN

HC CDR2  
(SEQ ID NO: 26)  
SGSSG

HC CDR3  
(SEQ ID NO: 24)  
GWNL

IIb. Clone 39-vh1  
Clone 39-vh1 HC DNA coding sequence  
(SEQ ID NO: 6)  
```
ATGGAGACTGGGCTGCGCTGGCTTCTCCTGGTCGCTGTGCTCAAAGGTGTC

CAGTGTCAGGAACAGCTGGTGGAGTCCGGGGGAGGCCTGGTCCAGCCTGAG

GGATCCCTGACACTCACCTGCACAGCCTCTGGATTCGACCTCGGTAACAAC

TGGATACACTGGGTCCGCCACGCTCCAGGGAAGGGACTGGAATGGATCGCA

TGCGTTAGTGGTAGTAGCGGCAACATTTACTACGCGACTTGGGCGAAAGGC

CGATTCACCATGTCCAAAGCCTCGTCGACCACGGTGACTCTACGAATGACC

AGTCTGACAGCCGCGGACACGGCCACCTATTTCTGTGCGAGAGGATGGAAC

TTGTGGGGCCCAGGCACCCTGGTCACCGTCTCCTCAGGGCAACCTAAGGCT

CCATCAGTCTTCCCACTGGCCCCCTGCTGCGGGGACACACCCAGCTCCACG

GTGACCCTGGGCTGCCTGGTCAAAGGGTACCTCCCGGAGCCAGTGACCGTG

ACCTGGAACTCGGGCACCCTCACCAATGGGGTACGCACCTTCCCGTCCGTC

CGGCAGTCCTCAGGCCTCTACTCGCTGAGCAGCGTGGTGAGCGTGACCTCA

AGCAGCCAGCCCGTCACCTGCAACGTGGCCCACCCAGCCACCAACACCAAA

GTGGACAAGACCGTTGCGCCCTCGACATGCAGCAAGCCCACGTGCCCACCC

CCTGAACTCCTGGGGGGACCGTCTGTCTTCATCTTCCCCCCAAAACCCAAG

GACACCCTCATGATCTCACGCACCCCCGAGGTCACATGCGTGGTGGTGGAC

GTGAGCCAGGATGACCCCGAGGTGCAGTTCACATGGTACATAAACAACGAG

CAGGTGCGCACCGCCCGGCCGCCGCTACGGGAGCAGCAGTTCAACAGCACG
```

```
ATCCGCGTGGTCAGCACCCTCCCCATCGCGCACCAGGACTGGCTGAGGGGC

AAGGAGTTCAAGTGCAAAGTCCACAACAAGGCACTCCCGGCCCCCATCGAG

AAAACCATCTCCAAAGCCAGAGGGCAGCCCCTGGAGCCGAAGGTCTACACC

ATGGGCCCTCCCCGGGAGGAGCTGAGCAGCAGGTCGGTCAGCCTGACCTGC

ATGATCAACGGCTTCTACCCTTCCGACATCTCGGTGGAGTGGGAGAAGAAC

GGGAAGGCAGAGGACAACTACAAGACCACGCCGGCCGTGCTGGACAGCGAC

GGCTCCTACTTCCTCTACAGCAAGCTCTCAGTGCCCACGAGTGAGTGGCAG

CGGGGCGACGTCTTCACCTGCTCCGTGATGCACGAGGCCTTGCACAACCAC

TACACGCAGAAGTCCATCTCCCGCTCTCCGGGTAAATGA
```

39-vh1 HC variable region AA  
(SEQ ID NO: 1)  
METGLRWLLLVAVLKGVQCQEQLVESGGGLVQPEGSLTLTCTAS<u>GFDLGNN</u>
WIHWVRHAPGKGLEWIACV<u>SGSSG</u>NIYYATWAKGRFTMSKASSTTVTLRMT
SLTAADTATYFCAR<u>GWNL</u>WGPGTLVTVSS IIb. Clone 39-vh3  
Clone 39-vh3 HC DNA coding sequence  
(SEQ ID NO: 12)  
```
ATGGAGACTGGGCTGCGCTGGCTTCTCCTGGTCGCTGTGCTCAAAGATGTC

CAGTGTCAGGAACAGCTGGTGGAGTCCGGGGGAGGCCTGGTCCAGCCTGAG

GGATCCCTGACACTCACCTGCACAGCCTCTGGATTCGACCTCGGTAACAAC

TGGATACACTGGGTCCGCCACGCTCCAGGGAAGGGACTGGAATGGATCGCA

TGCGTTAGTGGTAGTAGCGGCAACATTTACTACGCGACTTGGGCGAAAGGC

CGATTCACCATGTCCAAAGCCTCGTCGACCACGGTGACTCTACGAATGACC

AGTCTGACAGCCGCGGACACGGCCACCTATTTCTGTGCGAGAGGATGGAAC

TTGTGGGGCCCAGGCACCCTGGTCACCGTCTCCTCAGGGCAACCTAAGGCT

CCATCAGTCTTCCCACTGGCCCCCTGCTGCGGGGACACACCCAGCTCCACG

GTGACCCTGGGCTGCCTGGTCAAAGGGTACCTCCCGGAGCCAGTGACCGTG

ACCTGGAACTCGGGCACCCTCACCAATGGGGTACGCACCTTCCCGTCCGTC

CGGCAGTCCTCAGGCCTCTACTCGCTGAGCAGCGTGGTGAGCGTGACCTCA

AGCAGCCAGCCCGTCACCTGCAACGTGGCCCACCCAGCCACCAACACCAAA

GTGGACAAGACCGTTGCGCCCTCGACATGCAGCAAGCCCACGTGCCCACCC

CCTGAACTCCTGGGGGGACCGTCTGTCTTCATCTTCCCCCCAAAACCCAAG

GACACCCTCATGATCTCACGCACCCCCGAGGTCACATGCGTGGTGGTGGAC

GTGAGCCAGGATGACCCCGAGGTGCAGTTCACATGGTACATAAACAACGAG

CAGGTGCGCACCGCCCGGCCGCCGCTACGGGAGCAGCAGTTCAACAGCACG

ATCCGCGTGGTCAGCACCCTCCCCATCGCGCACCAGGACTGGCTGAGGGGC

AAGGAGTTCAAGTGCAAAGTCCACAACAAGGCACTCCCGGCCCCCATCGAG

AAAACCATCTCCAAAGCCAGAGGGCAGCCCCTGGAGCCGAAGGTCTACACC

ATGGGCCCTCCCCGGGAGGAGCTGAGCAGCAGGTCGGTCAGCCTGACCTGC

ATGATCAACGGCTTCTACCCTTCCGACATCTCGGTGGAGTGGGAGAAGAAC

GGGAAGGCAGAGGACAACTACAAGACCACGCCGGCCGTGCTGGACAGCGAC

GGCTCCTACTTCCTCTACAGCAAGCTCTCAGTGCCCACGAGTGAGTGGCAG
```

-continued

CGGGGCGACGTCTTCACCTGCTCCGTGATGCACGAGGCCTTGCACAACCAC

TACACGCAGAAGTCCATCTCCCGCTCTCCGGGTAAATGA 39-vh3 HC variable region AA
(SEQ ID NO: 7)
METGLRWLLLVAVLKDVQCQEQLVESGGGLVQPEGSLTLTCTAS<u>GFDLGNN</u>

WIHWVRHAPGKGLEWIACV<u>SGSSG</u>NIYYATWAKGRFTMSKASSTTVTLRMT

SLTAADTATYFCAR<u>GWNL</u>WGPGTLVTVSS

III. Vectors, Cells, and Pharmaceutical Compositions

In certain aspects, provided herein are vectors comprising a polynucleotide of the present invention. In some embodiments, the present invention is directed to a vector or a set of vectors comprising a polynucleotide encoding an antibody or antigen binding molecule that specifically bind a polypeptide comprising the alpha chain of the constant region of the murine T cell receptor (TCR) or a fragment thereof and cells presenting such molecules, as described herein.

Any vector known in the art may be suitable for expressing the antibodies and antigen binding molecules of the present invention. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof.

In other aspects, provided herein are cells comprising a polynucleotide or a vector of the present invention. In some embodiments, the present invention is directed to cells, in vitro cells, comprising a polynucleotide encoding an antigen binding molecule, as described herein. In some embodiments, the present invention is directed to cells, e.g., in vitro cells, comprising a polynucleotide encoding an antibody or an antigen binding molecule thereof that specifically binds to a polypeptide comprising the alpha chain of the constant region of the murine T cell receptor (TCR) or a fragment thereof and cells presenting such molecules, as disclosed herein.

Any cell may be used as a host cell for the polynucleotides and vectors encoding all or a fragment of the antibodies and antigen binding molecules of the present invention. In some embodiments, a host cell may be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobacteriaceae such as *Escherichia*, e.g., *E. coli*; Bacilli such as *B. subtilis* and *B. licheniformis*; *Pseudomonas* such as *P. aeruginosa*; and *Streptomyces*. In some embodiments, a host cell is a mammalian cell, such as a human cell. In some embodiments, a host cell is a CHO cell and in other embodiments, a host cell is a sP2/0 or other murine cell. A host cell of the present invention may be obtained through any source known in the art.

Other aspects of the present invention are directed to compositions comprising a polynucleotide described herein, a vector described herein, an antibody described herein, an antigen binding molecule described herein, and/or an in vitro cell described herein. In some embodiments, the composition comprises a pharmaceutically acceptable carrier, diluent, solubilizer, emulsifier, preservative and/or adjuvant. In some embodiments, the composition comprises an excipient.

In some embodiments, the composition comprises a polynucleotide encoding an antibody or antigen binding molecule that specifically binds a polypeptide comprising the alpha chain of the constant region of the murine T cell receptor (TCR) or a fragment thereof and cells presenting such molecules. In some embodiments, the composition comprises an antigen binding molecule that specifically binds a polypeptide comprising the alpha chain of the constant region of the murine T cell receptor (TCR) or a fragment thereof and cells presenting such molecules. In another embodiment, the composition comprises an in vitro cell comprising a polynucleotide encoding an antibody or an antigen binding molecule thereof encoded by a polynucleotide disclosed herein.

IV. Exemplary Methods

The following section describes various exemplary methods of using the disclosed antigen binding molecules herein. Any of the antigen binding molecules, and fragments thereof, disclosed herein (including those provided by the Figures and the attached Sequence Listing) may be employed in the disclosed methods.

In some of the disclosed methods T cells may be employed. Such T cells may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

In view of the above description of antigen binding molecules that may be employed in the disclosed methods, representative methods will now be discussed in more detail.

Method of Determining a Number of Cells Presenting a Molecule of Interest

The present disclosure provides a method to determine the number of cells present in a sample that are expressing a molecule of interest. For example, it may be desirable to determine the number of immune cells present a sample obtained from a subject that are expressing a molecule of interest. Or it may be desirable to determine the number of cells transfected and expressing a molecule of interest, which may be used as a measure of the level of efficiency of the transfection. The disclosed method may be employed in these and other applications in which it is desirable to determine the number of cells present in a sample that are expressing a molecule of interest.

Thus, a method of determining a number of cells presenting a molecule in a sample wherein the molecule comprises a polypeptide comprising the alpha chain of the constant region of the murine T cell receptor (TCR) or a fragment thereof is provided.

In some embodiments, a sample comprising cells known or suspected to be expressing a molecule of interest comprising a polypeptide comprising the alpha chain of the constant region of the murine T cell receptor (TCR) or a fragment thereof is provided.

The cell may be of any type, and may be human or non-human (e.g., mouse, rate, rabbit, hamster, etc.). In a preferred embodiment, the cell is an immune cell. An immune cell of the method may be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which may be obtained as described herein and by methods known in the art. Any type of immune cell may be employed in this embodiment of the disclosed method. Exemplary cells include, but are not limited to immune cells such as T cells, tumor infiltrating lymphocytes (TILs), NK cells, TCR-expressing cells, dendritic cells, and NK-T cells. The T cells may be autologous, allogeneic, or heterologous. The T cells may be CD4+ T cells or CD8+ T cells. When a T cell is employed in the disclosed methods, the T cell may be an in vivo T cell or an in vitro T cell. Moreover, the cells may be disposed in, or isolated from, any environment capable of maintaining the cells in a viable form, such as blood, tissue or any other sample obtained from a subject, cell culture media, tissue grown ex vivo, a suitable buffer, etc.

The sample is then contacted with an antigen binding molecule that specifically binds the molecule of interest, under conditions that permit the formation of a binding complex comprising a cell present in the sample and the antigen binding molecule. The antigen binding molecule is preferably an antigen binding molecule (or fragment thereof) disclosed herein, e.g., in the Figures, Sequence Listing or the instant section of the disclosure. Any antigen binding molecule that specifically binds a polypeptide comprising the alpha chain of the constant region of the murine T cell receptor (TCR) or a fragment thereof may be employed in the disclosed method. Multiple examples of suitable antigen binding molecules are provided herein, e.g., those having one or more of the CDRs shown in FIGS. 1A-C and described herein.

In some embodiments, the method of detection comprises a label-free assay. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)).

In some embodiments, the antigen binding molecule further comprises a detectable label. Any detectable label may be employed in the method, and suitable labels may be selected using a desired set of criteria. Examples of types of detectable labels include a fluorescent dye, which may be selected from the group consisting of an Atto dye, an Alexafluor dye, quantum dots, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyanl, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. Other types of detectable labels include optical dyes, which are described in Johnson, *Molecular Probes Handbook: A Guide to Fluorescent Probes and Labeling Techniques*, 11$^{th}$ Edition, Life Technologies, (2010), hereby expressly incorporated by reference, radiolabels (e.g., isotope markers such as $^{3}$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I), photochromic compounds, magnetic labels (e.g., DYNABEADS), etc. Strategies for the labeling of proteins are known in the art and may be employed in the disclosed method.

The label may be associated with the antigen binding molecule at any position in the molecule. In some embodiments, the label is associated with the molecule at a position (or positions, if multiple labels are employed) such that the binding properties of the molecule are not modified (unless such modified binding activity is desired). Any antigen binding molecule or fragment thereof that specifically binds the molecule of interest comprising a polypeptide comprising the alpha chain of the constant region of the murine T cell receptor (TCR) or a fragment thereof may be employed in the disclosed method.

The antigen binding molecule may be disposed on any surface, or no surface at all. For example, the antigen binding molecule may be present in a buffer and the buffer-antigen binding molecule may be contacted with the sample. Alternatively, the antigen binding molecule may be associated with a surface. Suitable surfaces include agarose beads, magnetic beads such as DYNABEADS, or a plastic, glass or ceramic plate such as a welled plate, a bag such as a cell culture bag, etc. The surface may itself be disposed in another structure, such as a column.

Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method.

Continuing, the number of cells present in a binding complex in the sample is determined. The specific method employed to determine the number of cells present in a binding complex will be dependent on the nature of the label selected. The output of the detection methods may be in the form of a number of cells or the output may be of a form that allows the calculation of the number of cells based on the output.

Method of Determining the Presence or Absence of a Molecule

In some embodiments, knowing whether a molecule comprising the alpha chain of the constant region of the murine T cell receptor (TCR) or a fragment thereof, is present or absent from a sample is enough information. For example, it may be beneficial to know that such a molecule is being expressed, regardless of the level of expression. In other cases, it may be desirable to know if a purification process or step designed to remove such a molecule has been effectively. Thus, the qualitative determination of the presence or absence of a polypeptide comprising the alpha chain of the constant region of the murine T cell receptor (TCR) or a fragment thereof, may be useful in multiple applications.

In some embodiments, a method of determining the presence or absence in a sample of a polypeptide comprising the alpha chain of the constant region of the murine T cell receptor (TCR) or a fragment thereof, in a sample is provided.

In some embodiments, the method comprises providing a sample known or suspected to comprise a polypeptide comprising the alpha chain of the constant region of the T cell receptor (TCR) or a fragment thereof. In some embodiments, the TCR is a murine TCR. In specific embodiments, the molecule comprising the selected amino acid sequence (a polypeptide comprising the alpha chain of the constant region of the murine T cell receptor (TCR) or a fragment thereof) is a chimeric TCR comprising human and murine sequences.

An antigen binding molecule specifically binds a polypeptide comprising the alpha chain of the constant region of the murine T cell receptor (TCR) or a fragment thereof further comprising a detectable label is provided. Suitable labels may be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cascade Yellow and R-phycoerythrin (PE) (Molecular Probes), FITC, Rhodamine, and Texas Red (Pierce), Cy5, Cy5.5, Cy7 (Amersham Life Science)). Suitable optical dyes, including fluorophores, are described in Johnson, *Molecular Probes Handbook: A Guide to Fluorescent Probes and Labeling Techniques,* 11$^{th}$ Edition, Life Technologies, (2010), hereby expressly incorporated by reference, radiolabels (e.g., isotope markers such as $^3$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I). Photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus,* or *Aequorea* species of GFP (Chalfie et al., (1994) *Science* 263:802-805), EGFP (Clon-tech Labs, Inc., Genbank Accession Number U55762), blue fluorescent protein (BFP, Quantum Biotechnologies, Inc.; Stauber, (1998) *Biotechniques* 24:462-471; Heim et al., (1996) *Curr. Biol.* 6: 178-182), enhanced yellow fluorescent protein (Clontech Labs, Inc.), luciferase (Ichiki et al., (1993) *J. Immunol.* 150:5408-5417), magnetic labels (e.g., DYNABEADS), etc. may also be employed. Strategies for the labeling of proteins are well known in the art and may be employed in the disclosed method. The label may be associated with the antigen binding molecule at any position in the molecule, although it is preferable to associate the label with the molecule at a position (or positions, if multiple labels are employed) at a point such that the binding properties of the molecule are not modified (unless such modified binding activity is desired).

Any antigen binding molecule that specifically binds a polypeptide comprising the alpha chain of the constant region of the murine T cell receptor (TCR) or a fragment thereof may be employed, such as those disclosed herein, e.g., those having one or more of the CDRs shown in FIGS. 1A-C.

Continuing, the sample is contacted with the antigen binding molecule under conditions that permit the formation of a binding complex comprising a cell present in the sample and the antigen binding molecule.

The sample is contacted with the antigen binding molecule, under conditions that permit the formation of a binding complex between a polypeptide comprising the alpha chain of the constant region of the murine T cell receptor (TCR) or a fragment thereof and the antigen binding molecule. Conditions that permit the formation of a binding complex will be dependent on a variety of factors. Since the component parts of a binding complex may be disposed on surfaces as described herein, formed binding complexes may also be disposed on surfaces.

At this stage, no binding complexes may have formed, or a plurality of binding complexes comprising one or more antigen binding molecules bound to a polypeptide comprising the alpha chain of the constant region of the murine T cell receptor (TCR) or a fragment thereof may have formed. Unbound molecules comprising the alpha chain of the constant region of the murine T cell receptor (TCR) or a fragment thereof and/or unbound antigen binding molecules may also be present in the local environment of any formed binding complexes.

Any molecules not part of a binding complex are then separated from any formed binding complexes. The method of the removal will depend on the structure and/or local environment of the binding complexes. For example, if the antigen binding molecule is disposed on a bead, plate or bag the unbound components of the reaction mixture may be washed away using a solution that leaves formed binding complexes intact. In some embodiments, separation of the binding complex is not required for detection.

The solution used to induce the formation of binding complexes may be used, for example, as a wash solution to remove unbound components. Any suitable buffer or solution that does not disrupt formed binding complexes may also be used. Typically, buffers having high salt concentrations, non-physiological pH, containing chaotropes or denaturants, should be avoided when performing this step of the method.

The presence or absence of a binding complex—which will comprise a polypeptide comprising the alpha chain of the constant region of the murine T cell receptor (TCR) or a fragment thereof and an antigen binding molecule—is detected. The specific method employed to detect the presence or absence of a binding complex will be dependent on the nature of the label selected. In some embodiments, the detection method is by colorimetric assay. The result of the method is a qualitative assessment of the presence or absence of the antigen binding molecule comprising the detectable label, and thus, the presence or absence of its binding partner, a polypeptide comprising the alpha chain of the constant region of the murine T cell receptor (TCR) or a fragment thereof.

As is the case with all of the disclosed methods, the polypeptide comprising the alpha chain of the constant region of the murine T cell receptor (TCR) or a fragment thereof may be disposed in any environment. In some embodiments, the polypeptide comprising the alpha chain of the constant region of the murine T cell receptor (TCR) or a fragment thereof is expressed on the surface of a cell. In this embodiment, the cell may be of any type, and may be human or non-human (e.g., mouse, rate, rabbit, hamster, etc.). In some embodiments, the cell is an immune cell. An immune cell of the method may be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which may be obtained as described herein and by methods known in the art. Any type of immune cell may be employed in this embodiment of the disclosed method, and the cell may be a human or non-human cell. Exemplary cells include, but are not limited to immune cells such as T cells, tumor infiltrating lymphocytes (TILs), NK cells, dendritic cells, and NK-T cells. The T cells may be autologous, allogeneic, or heterologous. In additional embodiments, the cells are T cells presenting a TCR. The T cells may be CD4+ T cells or CD8+ T cells. When a T cell is employed in the disclosed methods, the T cell may be an in vivo T cell or an in vitro T cell.

In some embodiments, the cell may be disposed in, or isolated from, any environment capable of maintaining the cell in a viable form, such as blood, tissue or any other sample obtained from a subject, cell culture media, tissue grown ex vivo, a suitable buffer, etc. In some embodiments, the cell is in a formalin-fixed sample. In some embodiments, the sample is a formalin-fixed paraffin embedded tissue (FFPE).

INCORPORATION BY REFERENCE

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

The foregoing written specification is considered to be sufficient to enable one skilled in the art to practice the invention. The foregoing description and Examples that follow detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

EXAMPLES

The present invention is further illustrated by the following examples which should not be construed as further limiting. The contents of all references cited throughout this application are expressly incorporated herein by reference.

Example 1: Generation of Antigen Binding Molecules

Monoclonal antibodies were generated through immunization of rabbits using the peptide, ATYPSSDVPSDATLT (SEQ ID NO: 30) as immunogen based on predicted immunogenicity and distinction from the human counterpart alpha chain TCR counterpart. Standard ELISA assays were performed where KDPRSQDSTLC (SEQ ID NO: 31) and C-EDATYPSSDVPSDATLT (SEQ ID NO: 32) antigens were coated on the plate at 1 µg/ml. The plate was washed and blocked. The multiclone supernatants were added neat. The plate was washed and an anti-rabbit IgG-AP (Alkaline Phosphatase) conjugate was added. After a 1 hour incubation, the plate was washed, and PNPP-substrate was added. The color development was stopped with 3 M NaOH and the plate was read at 405 nm. The results of the ELISA screen are shown in FIGS. 3A-3D.

As shown in FIG. 4, supernatants were tested at two concentrations: undiluted and at a 1:40 dilution. The IgG ELISA was coated with a goat anti-rabbit antibody and the subclone supernatant was added at two dilutions, neat and 1:40 dilution. A standard curve was made with a commercially available Rabbit IgG. The O.D. from the two points from the subclone supernatants were used to calculate the IgG concentration based on the standard curve. The last two columns shown in FIG. 4 are standard ELISAs where KIP-8A (SEQ ID NO: 31) and KIP-8B (SEQ ID NO: 32) antigens were coated on the plate at 1 µg/ml. The plate was washed and blocked. The subclone supernatants were added at two dilutions, neat and 1:40. After the plate was washed, an anti-rabbit IgG-AP was added. After a 1 hour incubation, the plate was washed, and PNPP-substrate was added. The color development is stopped with 3 M NaOH and the plate was read at 405 nm.

Example 2: Immunohistochemistry (IHC)

Figure 6:
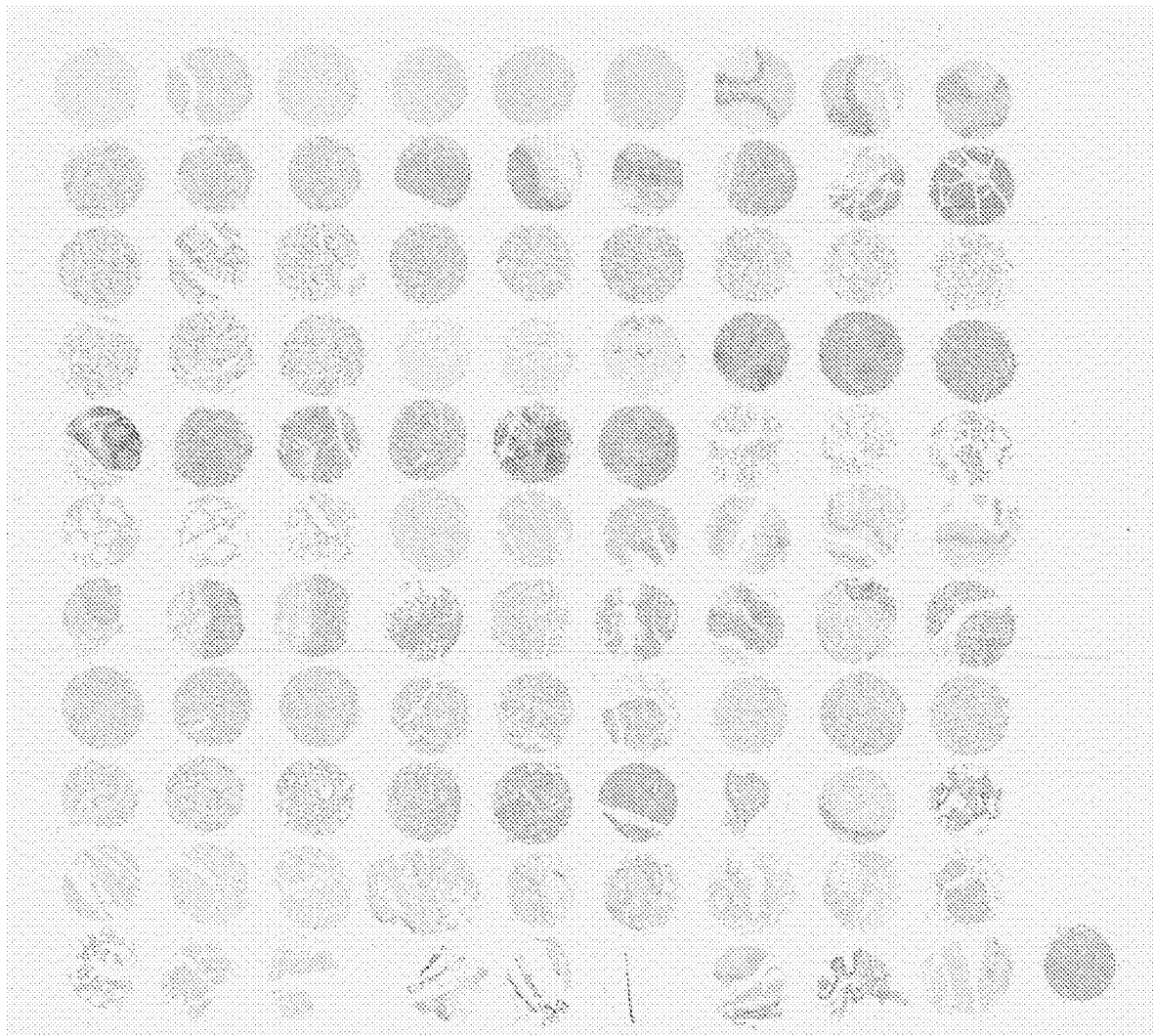
FIG. 6 shows sections of normal human tissues arranged in a tissue microarray (TMA) negative for staining with KIP-8.

The candidate antibodies were screened for their utility in immunohistochemistry. Specimens were sectioned at 4 micron thickness, mounted onto positive-charged glass slides, dried, baked, deparaffinized, and rehydrated. Following rehydration, tissue sections were incubated in Envision Peroxidase (Dako) for 5 minutes to quench endogenous peroxidase. Sections underwent heat-induced epitope retrieval using high-pH buffer for 40 minutes in a water bath set to 95° C. followed by a rinse in neutral buffer. Slides were incubated with antibody or negative reagent control diluted in diluent for 30 minutes. Slides were then rinsed twice in buffer for 5 minutes each followed by detection using the Envision+Rabbit HRP Detection Kit (Dako) for 30 minutes. Slides were rinsed twice with buffer for 5 minutes each followed by incubation with DAB (Dako) for 5 minutes. Slides were rinsed with water, counterstained with hematoxylin, blued in ammonia water, dehydrated through graded alcohols, cleared in xylene, and coverslipped. As shown in FIGS. 5A-E, E7 TCR-transduced, Peripheral blood mononuclear cells (PBMCs) transduced with the MAGE A3/A6 TCR, and FFPE section of mouse spleen stain with the exemplary mAb clone 39 (KIP-8) antibody described herein. Mock-transduced FFPE embedded cell pellets and PBMCs transduced with CD19 CARs do not stain with the KIP-8 antibody. As an additional control shown in FIG. 6, sections of normal human tissues arranged in a tissue microarray (TMA) do not stain with clone 39 (KIP-8) antibody described herein. These data demonstrate the antibody specifically recognizes the peptide immunogen on ELISA. Cell lines or peripheral blood mononuclear cells (PBMCs) transduced with murine/human chimeric TCRs stain with KIP-8; mock-transduced cell lines or cells transduced with chimeric antigen receptors (CARs) that contain no murine sequence do not stain with KIP-8, indicating its specificity for the murine alpha constant sequence. Normal mouse spleen sections stain with KIP-8 further indicating its specificity for the murine alpha constant sequence.

Example 3: Generation of Humanized Sequences from Rabbit Antibodies Clones

The Molecular Operating Environment (MOE) software developed by Chemical Computing Group (CCG) may be used to generate alignments between the rabbit antibody clones and pairs of variable light and heavy chains, VL and VH, respectively from two databases:
(1) The Abysis human database: a database of about 2000 known human VL/VH sequence pairs from IMGT-LigM DB; and
(2) A human germline database: a database of germline sequences.

Humanized models show the best sequence alignments (highest identity to both the VL and VH domains) with fewest gaps. The top 100 antibody pairs from each human database are exported and clustered using kClust (Hauser, Mayer, & Soding, (2013) *BMC Bioinformatics,* 248).

Example 4: Therapeutic TCR Detection in Human Tumor Sample

Figure 7:
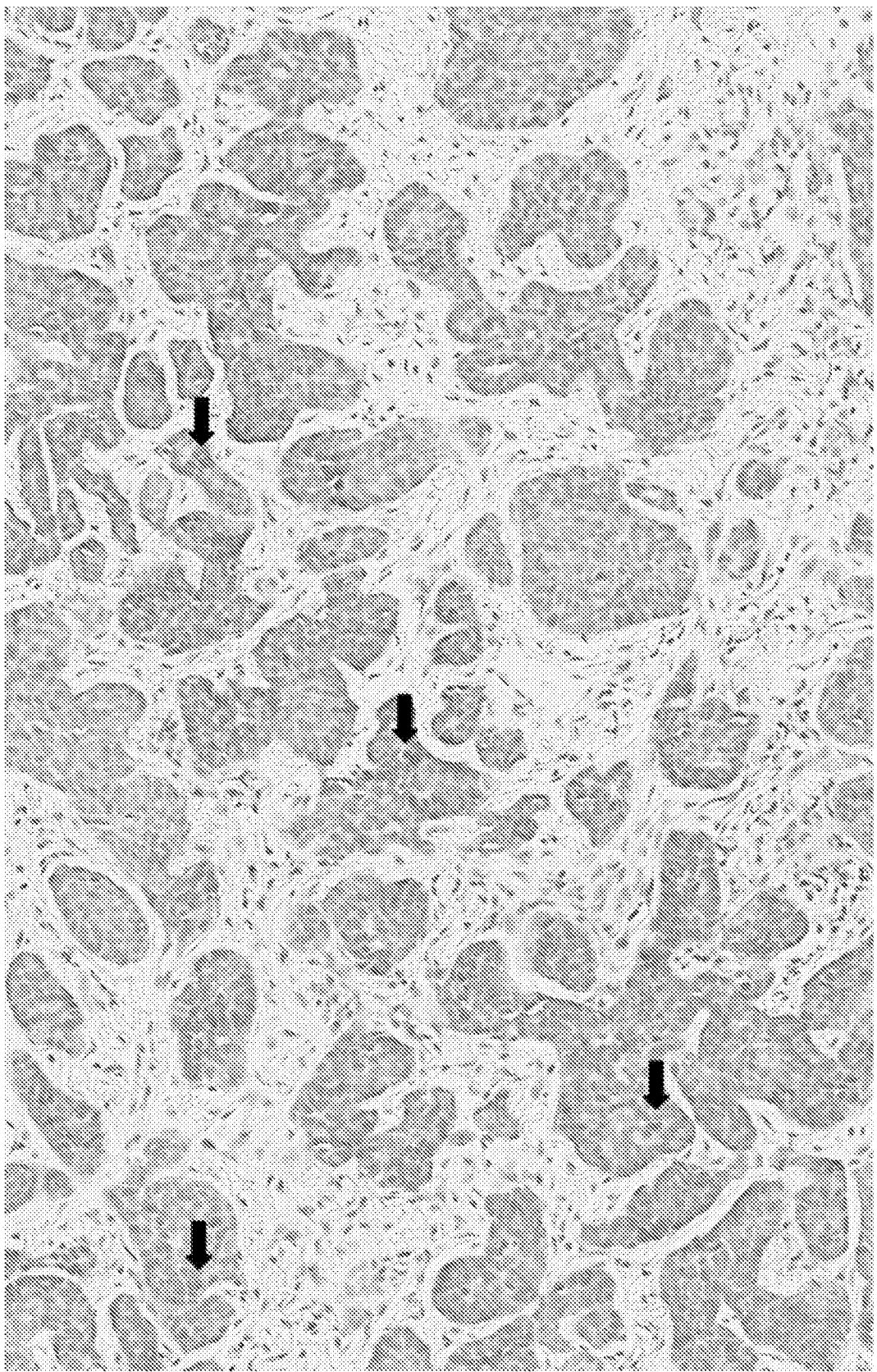
FIG. 7 shows a human tumor from a study subject that was treated with E6 TCR-transduced T cells and then biopsied several months later. Positive staining using KIP-8 is indicated with arrows.

A human tumor was biopsied from a study subject that was treated with E6 TCR-transduced T cells. As shown in FIG. 7, positive KIP-8 staining is indicated with arrows.

SEQUENCES AND SEQ ID NOs

The instant disclosure comprises a number of nucleic acid and polypeptide sequences. For convenience, Table C below correlates each sequence with its appropriate description and SEQ ID NO.

TABLE C

| SEQ ID NO: | Sequence | Description |
|---|---|---|
| SEQ ID NO: 1 | METGLRWLLLVAVLKGVQCQEQLVESGGG LVQPEGSLTLTCTASGFDLGNNWIHWVRHA PGKGLEWIACVSGSSGNIYYATWAKGRFTM SKASSTTVTLRMTSLTAADTATYFCARGWN LWGPGTLVTVSS | KIP-8-39-4vh1 protein |
| SEQ ID NO: 2 | ATGGAGACTGGGCTGCGCTGGCTTCTCCTG GTCGCTGTGCTCAAAGGTGTCCAGTGTCAG GAACAGCTGGTGGAGTCCGGGGGAGGCCT GGTCCAGCCTGAGGGATCCCTGACACTCA CCTGCACAGCCTCTGGATTCGACCTCGGTA ACAACTGGATACACTGGGTCCGCCACGCT CCAGGGAAGGGACTGGAATGGATCGCATG CGTTAGTGGTAGTAGCGGCAACATTTACTA CGCGACTTGGGCGAAAGGCCGATTCACCA TGTCCAAAGCCTCGTCGACCACGGTGACTC TACGAATGACCAGTCTGACAGCCGCGGAC ACGGCCACCTATTTCTGTGCGAGAGGATG GAACTTGTGGGGCCCAGGCACCCTGGTCA CCGTCTCCTCA | KIP-8-39-4vh1 DNA |
| SEQ ID NO: 3 | GQPKAPSVFPLAPCCGDTPSSTVTLGCLVKG YLPEPVTVTWNSGTLTNGVRTFPSVRQSSGL YSLSSVVSVTSSSQPVTCNVAHPATNTKVDK TVAPSTCSKPTCPPPELLGGPSVFIFPPKPKDT LMISRTPEVTCVVVDVSQDDPEVQFTWYINN EQVRTARPPLREQQFNSTIRVVSTLPIAHQD WLRGKEFKCKVHNKALPAPIEKTISKARGQP LEPKVYTMGPPREELSSRSVSLTCMINGFYPS DISVEWEKNGKAEDNYKTTPAVLDSDGSYF LYSKLSVPTSEWQRGDVFTCSVMHEALHNH YTQKSISRSPGK | KIP-8-39-4vh1 CONSTANT protein |
| SEQ ID NO: 4 | GGGCAACCTAAGGCTCCATCAGTCTTCCCA CTGGCCCCCTGCTGCGGGGACACACCCAG CTCCACGGTGACCCTGGGCTGCCTGGTCAA AGGGTACCTCCCGGAGCCAGTGACCGTGA CCTGGAACTCGGGCACCCTCACCAATGGG GTACGCACCTTCCCGTCCGTCCGGCAGTCC TCAGGCCTCTACTCGCTGAGCAGCGTGGTG AGCGTGACCTCAAGCAGCCAGCCCGTCAC CTGCAACGTGGCCCACCCAGCCACCAACA CCAAAGTGGACAAGACCGTTGCGCCCTCG ACATGCAGCAAGCCCACGTGCCCACCCCC TGAACTCCTGGGGGGACCGTCTGTCTTCAT CTTCCCCCCAAAACCCAAGGACACCCTCAT GATCTCACGCACCCCCGAGGTCACATGCGT GGTGGTGGACGTGAGCCAGGATGACCCCG AGGTGCAGTTCACATGGTACATAAACAAC GAGCAGGTGCGCACCGCCCGGCCGCCGCT ACGGGAGCAGCAGTTCAACAGCACGATCC GCGTGGTCAGCACCCTCCCCATCGCGCACC AGGACTGGCTGAGGGGCAAGGAGTTCAAG TGCAAAGTCCACAACAAGGCACTCCCGGC CCCCATCGAGAAAACCATCTCCAAAGCCA | KIP-8-39-4vh1 CONSTANT DNA |

TABLE C-continued

| SEQ ID NO: | Sequence | Description |
|---|---|---|
| | GAGGGCAGCCCCTGGAGCCGAAGGTCTAC ACCATGGGCCCTCCCCGGGAGGAGCTGAG CAGCAGGTCGGTCAGCCTGACCTGCATGA TCAACGGCTTCTACCCTTCCGACATCTCGG TGGAGTGGGAGAAGAACGGGAAGGCAGA GGACAACTACAAGACCACGCCGGCCGTGC TGGACAGCGACGGCTCCTACTTCCTCTACA GCAAGCTCTCAGTGCCCACGAGTGAGTGG CAGCGGGGCGACGTCTTCACCTGCTCCGTG ATGCACGAGGCCTTGCACAACCACTACAC GCAGAAGTCCATCTCCCGCTCTCCGGGTAA ATGA | |
| SEQ ID NO: 5 | METGLRWLLLLAVLKGVQCQEQLVESGGG LVQPEGSLTLTCTASGFDLGNNWIHWVRHA PGKGLEWIACVSGSSGNIYYATWAKGRFTM SKASSTTVTLRMTSLTAADTATYFCARGWN LWGPGTLVTVSS GQPKAPSVFPLAPCCGDTPSSTVTLGCLVKG YLPEPVTVTWNSGTLTNGVRTFPSVRQSSGL YSLSSVVSVTSSSQPVTCNVAHPATNTKVDK TVAPSTCSKPTCPPPELLGGPSVFIFPPKPKDT LMISRTPEVTCVVVDVSQDDPEVQFTWYINN EQVRTARPPLREQQFNSTIRVVSTLPIAHQD WLRGKEFKCKVHNKALPAPIEKTISKARGQP LEPKVYTMGPPREELSSRSVSLTCMINGFYPS DISVEWEKNGKAEDNYKTTPAVLDSDGSYF LYSKLSVPTSEWQRGDVFTCSVMHEALHNH YTQKSISRSPGK | KIP-8-39-4vh1 Full heavy chain Protein |
| SEQ ID NO: 6 | ATGGAGACTGGGCTGCGCTGGCTTCTCCTG GTCGCTGTGCTCAAAGGTGTCCAGTGTCAG GAACAGCTGGTGGAGTCCGGGGGAGGCCT GGTCCAGCCTGAGGGATCCCTGACACTCA CCTGCACAGCCTCTGGATTCGACCTCGGTA ACAACTGGATACACTGGGTCCGCCACGCT CCAGGGAAGGGACTGGAATGGATCGCATG CGTTAGTGGTAGTAGCGGCAACATTTACTA CGCGACTTGGGCGAAAGGCCGATTCACCA TGTCCAAAGCCTCGTCGACCACGGTGACTC TACGAATGACCAGTCTGACAGCCGCGGAC ACGGCCACCTATTTCTGTGCGAGAGGATG GAACTTGTGGGGCCCAGGCACCCTGGTCA CCGTCTCCTCA GGGCAACCTAAGGCTCCATCAGTCTTCCCA CTGGCCCCCTGCTGCGGGGACACACCCAG CTCCACGGTGACCCTGGGCTGCCTGGTCAA AGGGTACCTCCCGGAGCCAGTGACCGTGA CCTGGAACTCGGGCACCCTCACCAATGGG GTACGCACCTTCCCGTCCGTCCGGCAGTCC TCAGGCCTCTACTCGCTGAGCAGCGTGGTG AGCGTGACCTCAAGCAGCCAGCCCGTCAC CTGCAACGTGGCCCACCCAGCCACCAACA CCAAAGTGGACAAGACCGTTGCGCCCTCG ACATGCAGCAAGCCCACGTGCCCACCCCC TGAACTCCTGGGGGGACCGTCTGTCTTCAT CTTCCCCCCAAAAACCCAAGGACACCCTCAT GATCTCACGCACCCCCGAGGTCACATGCGT GGTGGTGGACGTGAGCCAGGATGACCCCG AGGTGCAGTTCACATGGTACATAAACAAC GAGCAGGTGCGCACCGCCCGGCCGCCGCT ACGGGAGCAGCAGTTCAACAGCACGATCC GCGTGGTCAGCACCCTCCCCATCGCGCACC AGGACTGGCTGAGGGGCAAGGAGTTCAAG TGCAAAGTCCACAACAAGGCACTCCCGGC CCCCATCGAGAAAACCATCTCCAAAGCCA GAGGGCAGCCCCTGGAGCCGAAGGTCTAC ACCATGGGCCCTCCCCGGGAGGAGCTGAG CAGCAGGTCGGTCAGCCTGACCTGCATGA TCAACGGCTTCTACCCTTCCGACATCTCGG TGGAGTGGGAGAAGAACGGGAAGGCAGA GGACAACTACAAGACCACGCCGGCCGTGC TGGACAGCGACGGCTCCTACTTCCTCTACA GCAAGCTCTCAGTGCCCACGAGTGAGTGG CAGCGGGGCGACGTCTTCACCTGCTCCGTG ATGCACGAGGCCTTGCACAACCACTACAC GCAGAAGTCCATCTCCCGCTCTCCGGGTAA ATGA | KIP-8-39-4vh1 Full heavy chain DNA |

TABLE C-continued

| SEQ ID NO: | Sequence | Description |
|---|---|---|
| SEQ ID NO: 7 | METGLRWLLLVAVLKDVQCQEQLVESGGG LVQPEGSLTLTCTASGFDLGNNWIHWVRHA PGKGLEWIACVSGSSGNIYYATWAKGRFTM SKASSTTVTLRMTSLTAADTATYFCARGWN LWGPGTLVTVSS | KIP-8-39-4vh3 protein |
| SEQ ID NO: 8 | ATGGAGACTGGGCTGCGCTGGCTTCTCCTG GTCGCTGTGCTCAAAGATGTCCAGTGTCAG GAACAGCTGGTGGAGTCCGGGGGAGGCCT GGTCCAGCCTGAGGGATCCCTGACACTCA CCTGCACAGCCTCTGGATTCGACCTCGGTA ACAACTGGATACACTGGGTCCGCCACGCT CCAGGGAAGGGACTGGAATGGATCGCATG CGTTAGTGGTAGTAGCGGCAACATTTACTA CGCGACTTGGGCGAAAGGCCGATTCACCA TGTCCAAAGCCTCGTCGACCACGGTGACTC TACGAATGACCAGTCTGACAGCCGCGGAC ACGGCCACCTATTTCTGTGCGAGAGGATG GAACTTGTGGGGCCCAGGCACCCTGGTCA CCGTCTCCTCA | KIP-8-39-4vh3 DNA |
| SEQ ID NO: 9 | GQPKAPSVFPLAPCCGDTPSSTVTLGCLVKG YLPEPVTVTWNSGTLTNGVRTFPSVRQSSGL YSLSSVVSVTSSSQPVTCNVAHPATNTKVDK TVAPSTCSKPTCPPPELLGGPSVFIFPPKPKDT LMISRTPEVTCVVVDVSQDDPEVQFTWYINN EQVRTARPPLREQQFNSTIRVVSTLPIAHQD WLRGKEFKCKVHNKALPAPIEKTISKARGQP LEPKVYTMGPPREELSSRSVSLTCMINGFYPS DISVEWEKNGKAEDNYKTTPAVLDSDGSYF LYSKLSVPTSEWQRGDVFTCSVMHEALHNH YTQKSISRSPGK | KIP-8-39-4vh3 constant protein |
| SEQ ID NO: 10 | GGGCAACCTAAGGCTCCATCAGTCTTCCCA CTGGCCCCCTGCTGCGGGGACACACCCAG CTCCACGGTGACCCTGGGCTGCCTGGTCAA AGGGTACCTCCCGGAGCCAGTGACCGTGA CCTGGAACTCGGGCACCCTCACCAATGGG GTACGCACCTTCCCGTCCGTCCGGCAGTCC TCAGGCCTCTACTCGCTGAGCAGCGTGGTG AGCGTGACCTCAAGCAGCCAGCCCGTCAC CTGCAACGTGGCCCACCCAGCCACCAACA CCAAAGTGGACAAGACCGTTGCGCCCTCG ACATGCAGCAAGCCCACGTGCCCACCCCC TGAACTCCTGGGGGGACCGTCTGTCTTCAT CTTCCCCCCAAAACCCAAGGACACCCTCAT GATCTCACGCACCCCCGAGGTCACATGCGT GGTGGTGGACGTGAGCCAGGATGACCCCG AGGTGCAGTTCACATGGTACATAAACAAC GAGCAGGTGCGCACCGCCCGGCCGCCGCT ACGGGAGCAGCAGTTCAACAGCACGATCC GCGTGGTCAGCACCCTCCCCATCGCGCACC AGGACTGGCTGAGGGGCAAGGAGTTCAAG TGCAAAGTCCACAACAAGGCACTCCCGGC CCCCATCGAGAAAACCATCTCCAAAGCCA GAGGGCAGCCCCTGGAGCCGAAGGTCTAC ACCATGGGCCCTCCCCGGGAGGAGCTGAG CAGCAGGTCGGTCAGCCTGACCTGCATGA TCAACGGCTTCTACCCTTCCGACATCTCGG TGGAGTGGGAGAAGAACGGGAAGGCAGA GGACAACTACAAGACCACGCCGGCCGTGC TGGACAGCGACGGCTCCTACTTCCTCTACA GCAAGCTCTCAGTGCCCACGAGTGAGTGG CAGCGGGGCGACGTCTTCACCTGCTCCGTG ATGCACGAGGCCTTGCACAACCACTACAC GCAGAAGTCCATCTCCCGCTCTCCGGGTAA ATGA | KIP-8-39-4vh3 constant DNA |
| SEQ ID NO: 11 | METGLRWLLLVAVLKDVQCQEQLVESGGG LVQPEGSLTLTCTASGFDLGNNWIHWVRHA PGKGLEWIACVSGSSGNIYYATWAKGRFTM SKASSTTVTLRMTSLTAADTATYFCARGWN LWGPGTLVTVSS GQPKAPSVFPLAPCCGDTPSSTVTLGCLVKG YLPEPVTVTWNSGTLTNGVRTFPSVRQSSGL YSLSSVVSVTSSSQPVTCNVAHPATNTKVDK TVAPSTCSKPTCPPPELLGGPSVFIFPPKPKDT | KIP-8-39-4vh3 Full Heavy Chain Protein |

TABLE C-continued

| SEQ ID NO: | Sequence | Description |
|---|---|---|
| | LMISRTPEVTCVVVDVSQDDPEVQFTWYINN EQVRTARPPLREQQFNSTIRVVSTLPIAHQD WLRGKEFKCKVHNKALPAPIEKTISKARGQP LEPKVYTMGPPREELSSRSVSLTCMINGFYPS DISVEWEKNGKAEDNYKTTPAVLDSDGSYF LYSKLSVPTSEWQRGDVFTCSVMHEALHNH YTQKSISRSPGK | |
| SEQ ID NO: 12 | ATGGAGACTGGGCTGCGCTGGCTTCTCCTG GTCGCTGTGCTCAAAGATGTCCAGTGTCAG GAACAGCTGGTGGAGTCCGGGGGAGGCCT GGTCCAGCCTGAGGGATCCCTGACACTCA CCTGCACAGCCTCTGGATTCGACCTCGGTA ACAACTGGATACACTGGGTCCGCCACGCT CCAGGGAAGGGACTGGAATGGATCGCATG CGTTAGTGGTAGTAGCGGCAACATTTACTA CGCGACTTGGGCGAAAGGCCCGATTCACCA TGTCCAAAGCCTCGTCGACCACGGTGACTC TACGAATGACCAGTCTGACAGCCGCGGAC ACGGCCACCTATTTCTGTGCGAGAGGATG GAACTTGTGGGGCCCAGGCACCCTGGTCA CCGTCTCCTCA GGGCAACCTAAGGCTCCATCAGTCTTCCCA CTGGCCCCCTGCTGCGGGGACACACCCAG CTCCACGGTGACCCTGGGCTGCCTGGTCAA AGGGTACCTCCCGGAGCCAGTGACCGTGA CCTGGAACTCGGGCACCCTCACCAATGGG GTACGCACCTTCCCGTCCGTCCGGCAGTCC TCAGGCCTCTACTCGCTGAGCAGCGTGGTG AGCGTGACCTCAAGCAGCCAGCCCGTCAC CTGCAACGTGGCCCACCCAGCCACCAACA CCAAAGTGGACAAGACCGTTGCGCCCTCG ACATGCAGCAAGCCCACGTGCCCACCCCC TGAACTCCTGGGGGGACCGTCTGTCTTCAT CTTCCCCCCAAAACCCAAGGACACCCTCAT GATCTCACGCACCCCCGAGGTCACATGCGT GGTGGTGGACGTGAGCCAGGATGACCCCG AGGTGCAGTTCACATGGTACATAAACAAC GAGCAGGTGCGCACCGCCCGGCCGCCGCT ACGGGAGCAGCAGTTCAACAGCACGATCC GCGTGGTCAGCACCCTCCCCATCGCGCACC AGGACTGGCTGAGGGGCAAGGAGTTCAAG TGCAAAGTCCACAACAAGGCACTCCCGGC CCCCATCGAGAAAACCATCTCCAAAGCCA GAGGGCAGCCCCTGGAGCCGAAGGTCTAC ACCATGGGCCCTCCCCGGGAGGAGCTGAG CAGCAGGTCGGTCAGCCTGACCTGCATGA TCAACGGCTTCTACCCTTCCGACATCTCGG TGGAGTGGGAGAAGAACGGGAAGGCAGA GGACAACTACAAGACCACGCCGGCCGTGC TGGACAGCGACGGCTCCTACTTCCTCTACA GCAAGCTCTCAGTGCCCACGAGTGAGTGG CAGCGGGGCGACGTCTTCACCTGCTCCGTG ATGCACGAGGCCTTGCACAACCACTACAC GCAGAAGTCCATCTCCCGCTCTCCGGGTAA ATGA | KIP-8-39-4vh3 Full Heavy Chain DNA |
| SEQ ID NO: 13 | MDTRAPTQLLGLLLLWLPGATFAQVLTQTP ASVSAAVGGTVTINCQASQSVYSSNLLTWY QKKPGQPPKLLIYEASKLPSGIPSRFSGSGSGT QFTLTISDVQCADAATYYCLGIYDCVLADCQ AFGGGTEVVVK | KIP-8-39-4vk light chain variable Protein |
| SEQ ID NO: 14 | ATGGACACGAGGGCCCCCACTCAGCTGCT GGGGCTCCTGCTGCTCTGGCTCCCAGGTGC CACATTTGCCCAAGTGCTGACCCAGACTCC AGCCTCGGTGTCTGCAGCTGTGGGAGGCA CAGTCACCATCAACTGCCAGGCCAGTCAG AGTGTTTATAGCAGCAACCTCTTAACCTGG TATCAGAAGAAACCAGGGCAGCCTCCCAA GCTCCTGATCTACGAAGCATCCAAACTGCC ATCTGGGATCCCATCGCGCTTCAGCGGCAG TGGATCTGGGACACAGTTCACTCTCACCAT CAGCGACGTACAGTGTGCCGATGCTGCCA CTTACTACTGTCTAGGCATTTATGATTGTG TGCTTGCTGATTGTCAGGCTTTCGGCGGAG GGACCGAAGTGGTGGTCAAA | KIP-8-39-4vk light chain variable DNA |

TABLE C-continued

| SEQ ID NO: | Sequence | Description |
|---|---|---|
| SEQ ID NO: 15 | GDPVAPTVLIFPPAADQVATGTVTIVCVANK YFPDVTVTWEVDGTTQTTGIENSKTPQNSAD CTYNLSSTLTLTSTQYNSHKEYTCKVTQGTT SVVQSFNRGDC | KIP-8-39-4vk light chain constant protein |
| SEQ ID NO: 16 | GGTGATCCAGTTGCACCTACTGTCCTCATC TTCCCACCAGCTGCTGATCAGGTGGCAACT GGAACAGTCACCATCGTGTGTGTGGCGAA TAAATACTTTCCCGATGTCACCGTCACCTG GGAGGTGGATGGCACCACCCAAACAACTG GCATCGAGAACAGTAAAACACCGCAGAAT TCTGCAGATTGTACCTACAACCTCAGCAGC ACTCTGACACTGACCAGCACACAGTACAA CAGCCACAAAGAGTACACCTGCAAGGTGA CCCAGGGCACGACCTCAGTCGTCCAGAGC TTCAATAGGGGTGACTGTTAG | KIP-8-39-4vk light chain constant DNA |
| SEQ ID NO: 17 | MDTRAPTQLLGLLLLWLPGATFAQVLTQTP ASVSAAVGGTVTINCQASQSVYSSNLLTWY QKKPGQPPKLLIYEASKLPSGIPSRFSGSGSGT QFTLTISDVQCADAATYYCLGIYDCVLADCQ AFGGGTEVVVK GDPVAPTVLIFPPAADQVATGTVTIVCVANK YFPDVTVTWEVDGTTQTTGIENSKTPQNSAD CTYNLSSTLTLTSTQYNSHKEYTCKVTQGTT SVVQSFNRGDC | KIP-8-39-4vk Full light chain protein |
| SEQ ID NO: 18 | ATGGACACGAGGGCCCCCACTCAGCTGCT GGGGCTCCTGCTGCTCTGGCTCCCAGGTGC CACATTTGCCCAAGTGCTGACCCAGACTCC AGCCTCGGTGTCTGCAGCTGTGGGAGGCA CAGTCACCATCAACTGCCAGGCCAGTCAG AGTGTTTATAGCAGCAACCTCTTAACCTGG TATCAGAAGAAACCAGGGCAGCCTCCCAA GCTCCTGATCTACGAAGCATCCAAACTGCC ATCTGGGATCCCATCGCGCTTCAGCGGCAG TGGATCTGGGACACAGTTCACTCTCACCAT CAGCGACGTACAGTGTGCCGATGCTGCCA CTTACTACTGTCTAGGCATTTATGATTGTG TGCTTGCTGATTGTCAGGCTTTCGGCGGAG GGACCGAAGTGGTGGTCAAA GGTGATCCAGTTGCACCTACTGTCCTCATC TTCCCACCAGCTGCTGATCAGGTGGCAACT GGAACAGTCACCATCGTGTGTGTGGCGAA TAAATACTTTCCCGATGTCACCGTCACCTG GGAGGTGGATGGCACCACCCAAACAACTG GCATCGAGAACAGTAAAACACCGCAGAAT TCTGCAGATTGTACCTACAACCTCAGCAGC ACTCTGACACTGACCAGCACACAGTACAA CAGCCACAAAGAGTACACCTGCAAGGTGA CCCAGGGCACGACCTCAGTCGTCCAGAGC TTCAATAGGGGTGACTGTTAG | KIP-8-39-4vk Full light chain DNA |
| SEQ ID NO: 19 | QASQSVYSSNLLT | 39-4_VL CDR1 Kabat/Clothia/IMGT |
| SEQ ID NO: 20 | EASKLPS | 39-4_VL CDR2 Kabat/Clothia/IMGT |
| SEQ ID NO: 21 | LGIYDCVLADCQA | 39-4_VL CDR3 Kabat/Clothia/IMGT |
| SEQ ID NO: 22 | NNWIH | 39-4_VH1 CDR1 Kabat 39-4_VH2 CDR1 Kabat/ IMGT |
| SEQ ID NO: 23 | CVSGSSGNIYYATWAK | 39-4_VH1 CDR2 Kabat 39-4_VH2 CDR2 Kabat |
| SEQ ID NO: 24 | GWNL | 39-4_VH1 CDR3 Kabat/Clothia 39-4_VH2 CDR3 Kabat/Clothia |
| SEQ ID NO: 25 | GFDLGNN | 39-4_VH1 CDR1 Clothia 39-4_VH2 CDR1 Clothia |

TABLE C-continued

| SEQ ID NO: | Sequence | Description |
| --- | --- | --- |
| SEQ ID NO: 26 | SGSSG | 39-4_VH1 CDR2 Clothia<br>39-4_VH2 CDR2 Clothia |
| SEQ ID NO: 27 | GFDLGNNW | 39-4_VH1 CDR1 IMGT |
| SEQ ID NO: 28 | VSGSSGN | 39-4_VH1 CDR2 IMGT<br>39-4_VH2 CDR2 IMGT |
| SEQ ID NO: 29 | ARGWNL | 39-4_VH1 CDR3 IMGT<br>39-4_VH2 CDR3 IMGT |
| SEQ ID NO: 30 | ATYPSSDVPSDATLT | AA83-97 - immunogen based on predicted immunogenicity and distinction from human counterpart |
| SEQ ID NO: 31 | KDPRSQDSTLC | KIP-8A |
| SEQ ID NO: 32 | C-EDATYPSSDVPSDATLT | KIP-8B |
| SEQ ID NO: 33 | METGLRWLLLVAVLKGVQCQEQLVESGGG<br>LVQPEGSLTLTCTASGFDLGNNWIHWVRHA<br>PGKGLEWIACVSGSSGNIYYATWAKGRFTM<br>SKASSTTVTLRMTSLTAADTATYFCARGWN<br>LWGPGTLVTVSS<br>GQPKAPSVFPLAPCCGDTPSSTVTLGCLVKG<br>YLPEPVTVTWNSGTLTNGVRTFPSVRQSSGL<br>YSLSSVVSVTSSSQPVTCNVAHPATNTKVDK<br>TVAPSTCSKPTCPPPELLGGPSVFIFPPKPKDT<br>LMISRTPEVTCVVVDVSQDDPEVQFTWYINN<br>EQVRTARPPLREQQFNSTIRVVSTLPIAHQD<br>WLRGKEFKCKVHNKALPAPIEKTISKARGQP<br>LEPKVYTMGPPREELSSRSVSLTCMINGFYPS<br>DISVEWEKNGKAEDNYKTTPAVLDSDGSYF<br>LYSKLSVPTSEWQRGDVFTCSVMHEALHNH<br>YTQKSISRSPGK | KIP-8-33-8vh |
| SEQ ID NO: 34 | ATGGAGACTGGGCTGCGCTGGCTTCTCCTG<br>GTCGCTGTGCTCAAAGGTGTCCAGTGTCAG<br>GAACAGCTGGTGGAGTCCGGGGGAGGCCT<br>GGTCCAGCCTGAGGGATCCCTGACACTCA<br>CCTGCACAGCCTCTGGATTCGACCTCGGTA<br>ACAACTGGATACACTGGGTCCGCCACGCT<br>CCAGGGAAGGGACTGGAATGGATCGCATG<br>CGTTAGTGGTAGTAGCGGCAACATTTACTA<br>CGCGACTTGGGCGAAAGGCCGATTCACCA<br>TGTCCAAAGCCTCGTCGACCACGGTGACTC<br>TACGAATGACCAGTCTGACAGCCGCGGAC<br>ACGGCCACCTATTTCTGTGCGAGAGGATG<br>GAACTTGTGGGGCCCAGGCACCCTGGTCA<br>CCGTCTCCTCA<br>GGGCAACCTAAGGCTCCATCAGTCTTCCCA<br>CTGGCCCCCTGCTGCGGGGACACACCCAG<br>CTCCACGGTGACCCTGGGCTGCCTGGTCAA<br>AGGGTACCTCCCGGAGCCAGTGACCGTGA<br>CCTGGAACTCGGGCACCCTCACCAATGGG<br>GTACGCACCTTCCCGTCCGTCCGGCAGTCC<br>TCAGGCCTCTACTCGCTGAGCAGCGTGGTG<br>AGCGTGACCTCAAGCAGCCAGCCCGTCAC<br>CTGCAACGTGGCCCACCCAGCCACCAACA<br>CCAAAGTGGACAAGACCGTTGCGCCCTCG<br>ACATGCAGCAAGCCCACGTGCCCACCCCC<br>TGAACTCCTGGGGGACCGTCTGTCTTCAT<br>CTTCCCCCCAAAACCCAAGGACACCCTCAT<br>GATCTCACGCACCCCCGAGGTCACATGCGT<br>GGTGGTGGACGTGAGCCAGGATGACCCCG<br>AGGTGCAGTTCACATGGTACATAAACAAC<br>GAGCAGGTGCGCACCGCCCGGCCGCCGCT<br>ACGGGAGCAGCAGTTCAACAGCACGATCC<br>GCGTGGTCAGCACCCTCCCCATCGCGCACC<br>AGGACTGGCTGAGGGGCAAGGAGTTCAAG<br>TGCAAAGTCCACAACAAGGCACTCCCGGC<br>CCCCATCGAGAAAACCATCTCCAAAGCCA<br>GAGGGCAGCCCCTGGAGCCGAAGGTCTAC | KIP-8-33-8vh DNA |

TABLE C-continued

| SEQ ID NO: | Sequence | Description |
|---|---|---|
| | ACCATGGGCCCTCCCCGGGAGGAGCTGAG<br>CAGCAGGTCGGTCAGCCTGACCTGCATGA<br>TCAACGGCTTCTACCCTTCCGACATCTCGG<br>TGGAGTGGGAGAAGAACGGGAAGGCAGA<br>GGACAACTACAAGACCACGCCGGCCGTGC<br>TGGACAGCGACGGCTCCTACTTCCTCTACA<br>GCAAGCTCTCAGTGCCCACGAGTGAGTGG<br>CAGCGGGGCGACGTCTTCACCTGCTCCGTG<br>ATGCACGAGGCCTTGCACAACCACTACAC<br>GCAGAAGTCCATCTCCCGCTCTCCGGGTAA<br>ATGA | |
| SEQ ID NO: 35 | METGLRWLLLVAVLKGVQCQEQLVESGGG<br>LVQPEGSLTLTCTASGFDLGNNWIHWVRHA<br>PGKGLEWIACVSGSSGNIYYATWAKGRFTM<br>SKASSTTVTLRMTSLTAADTATYFCARGWN<br>LWGPGTLVTVSS<br>GQPKAPSVFPLAPCCGDTPSSTVTLGCLVKG<br>YLPEPVTVTWNSGTLTNGVRTFPSVRQSSGL<br>YSLSSVVSVTSSSQPVTCNVAHPATNTKVDK<br>TVAPSTCSKPTCPPPELLGGPSVFIFPPKPKDT<br>LMISRTPEVTCVVVDVSQDDPEVQFTWYINN<br>EQVRTARPPLREQQFNSTIRVVSTLPIAHQD<br>WLRGKEFKCKVHNKALPAPIEKTISKARGQP<br>LEPKVYTMGPPREELSSRSVSLTCMINGFYPS<br>DISVEWEKNGKAEDNYKTTPAVLDSDGSYF<br>LYSKLSVPTSEWQRGDVFTCSVMHEALHNH<br>YTQKSISRSPGK | KIP-8-39-4vh |
| SEQ ID NO: 36 | ATGGAGACTGGGCTGCGCTGGCTTCTCCTG<br>GTCGCTGTGCTCAAAGGTGTCCAGTGTCAG<br>GAACAGCTGGTGGAGTCCGGGGGAGGCCT<br>GGTCCAGCCTGAGGGATCCCTGACACTCA<br>CCTGCACAGCCTCTGGATTCGACCTCGGTA<br>ACAACTGGATACACTGGGTCCGCCACGCT<br>CCAGGGAAGGGACTGGAATGGATCGCATG<br>CGTTAGTGGTAGTAGCGGCAACATTTACTA<br>CGCGACTTGGGCGAAAGGCCGATTCACCA<br>TGTCCAAAGCCTCGTCGACCACGGTGACTC<br>TACGAATGACCAGTCTGACAGCCGCGGAC<br>ACGGCCACCTATTTCTGTGCGAGAGGATG<br>GAACTTGTGGGGCCCAGGCACCCTGGTCA<br>CCGTCTCCTCA<br>GGGCAACCTAAGGCTCCATCAGTCTTCCCA<br>CTGGCCCCCTGCTGCGGGGACACACCCAG<br>CTCCACGGTGACCCTGGGCTGCCTGGTCAA<br>AGGGTACCTCCCGGAGCCAGTGACCGTGA<br>CCTGGAACTCGGGCACCCTCACCAATGGG<br>GTACGCACCTTCCCGTCCGTCCGGCAGTCC<br>TCAGGCCTCTACTCGCTGAGCAGCGTGGTG<br>AGCGTGACCTCAAGCAGCCAGCCCGTCAC<br>CTGCAACGTGGCCCACCCAGCCACCAACA<br>CCAAAGTGGACAAGACCGTTGCGCCCTCG<br>ACATGCAGCAAGCCCACGTGCCCACCCCC<br>TGAACTCCTGGGGGGACCGTCTGTCTTCAT<br>CTTCCCCCCAAAAACCCAAGGACACCCTCAT<br>GATCTCACGCACCCCCGAGGTCACATGCGT<br>GGTGGTGGACGTGAGCCAGGATGACCCCG<br>AGGTGCAGTTCACATGGTACATAAACAAC<br>GAGCAGGTGCGCACCGCCCGGCCGCCGCT<br>ACGGGAGCAGCAGTTCAACAGCACGATCC<br>GCGTGGTCAGCACCCTCCCCATCGCGCACC<br>AGGACTGGCTGAGGGGCAAGGAGTTCAAG<br>TGCAAAGTCCACAACAAGGCACTCCCGGC<br>CCCCATCGAGAAAACCATCTCCAAAGCCA<br>GAGGGCAGCCCCTGGAGCCGAAGGTCTAC<br>ACCATGGGCCCTCCCCGGGAGGAGCTGAG<br>CAGCAGGTCGGTCAGCCTGACCTGCATGA<br>TCAACGGCTTCTACCCTTCCGACATCTCGG<br>TGGAGTGGGAGAAGAACGGGAAGGCAGA<br>GGACAACTACAAGACCACGCCGGCCGTGC<br>TGGACAGCGACGGCTCCTACTTCCTCTACA<br>GCAAGCTCTCAGTGCCCACGAGTGAGTGG<br>CAGCGGGGCGACGTCTTCACCTGCTCCGTG<br>ATGCACGAGGCCTTGCACAACCACTACAC<br>GCAGAAGTCCATCTCCCGCTCTCCGGGTAA<br>ATGA | KIP-8-39-4vh DNA |

TABLE C-continued

| SEQ ID NO: | Sequence | Description |
| --- | --- | --- |
| SEQ ID NO: 37 | METGLRWLLLVAVLKGVQCQEQLVESGGG<br>LVQPEGSLTLTCTASGFDLGNNWIHWVRHA<br>PGKGLEWIACVSGSSGNIYYATWAKGRFTM<br>SKASSTTVTLRMTSLTAADTATYFCARGWN<br>LWGPGTLVTVSS<br>GQPKAPSVFPLAPCCGDTPSSTVTLGCLVKG<br>YLPEPVTVTWNSGTLTNGVRTFPSVRQSSGL<br>YSLSSVVSVTSSSQPVTCNVAHPATNTKVDK<br>TVAPSTCSKPTCPPPELLGGPSVFIFPPKPKDT<br>LMISRTPEVTCVVVDVSQDDPEVQFTWYINN<br>EQVRTARPPLREQQFNSTIRVVSTLPIAHQD<br>WLRGKEFKCKVHNKALPAPIEKTISKARGQP<br>LEPKVYTMGPPREELSSRSVSLTCMINGFYPS<br>DISVEWEKNGKAEDNYKTTPAVLDSDGSYF<br>LYSKLSVPTSEWQRGDVFTCSVMHEALHNH<br>YTQKSISRSPGK | KIP-8-78-4vh |
| SEQ ID NO: 38 | ATGGAGACTGGGCTGCGCTGGCTTCTCCTG<br>GTCGCTGTGCTCAAAGGTGTCCAGTGTCAG<br>GAACAGCTGGTGGAGTCCGGGGGAGGCCT<br>GGTCCAGCCTGAGGGATCCCTGACACTCA<br>CCTGCACAGCCTCTGGATTCGACCTCGGTA<br>ACAACTGGATACACTGGGTCCGCCACGCT<br>CCAGGGAAGGGACTGGAATGGATCGCATG<br>CGTTAGTGGTAGTAGCGGCAACATTTACTA<br>CGCGACTTGGGCGAAAGGCCGATTCACCA<br>TGTCCAAAGCCTCGTCGACCACGGTGACTC<br>TACGAATGACCAGTCTGACAGCCGCGGAC<br>ACGGCCACCTATTTCTGTGCGAGAGGATG<br>GAACTTGTGGGGCCCAGGCACCCTGGTCA<br>CCGTCTCCTCA<br>GGGCAACCTAAGGCTCCATCAGTCTTCCCA<br>CTGGCCCCCTGCTGCGGGGACACACCCAG<br>CTCCACGGTGACCCTGGGCTGCCTGGTCAA<br>AGGGTACCTCCCGGAGCCAGTGACCGTGA<br>CCTGGAACTCGGGCACCCTCACCAATGGG<br>GTACGCACCTTCCCGTCCGTCGGCAGTCC<br>TCAGGCCTCTACTCGCTGAGCAGCGTGGTG<br>AGCGTGACCTCAAGCAGCCAGCCCGTCAC<br>CTGCAACGTGGCCCACCCAGCCACCAACA<br>CCAAAGTGGACAAGACCGTTGCGCCCTCG<br>ACATGCAGCAAGCCCACGTGCCCACCCCC<br>TGAACTCCTGGGGGGACCGTCTGTCTTCAT<br>CTTCCCCCCAAAACCCAAGGACACCCTCAT<br>GATCTCACGCACCCCCGAGGTCACATGCGT<br>GGTGGTGGACGTGAGCCAGGATGACCCCG<br>AGGTGCAGTTCACATGGTACATAAACAAC<br>GAGCAGGTGCGCACCGCCCGGCCGCCGCT<br>ACGGGAGCAGCAGTTCAACAGCACGATCC<br>GCGTGGTCAGCACCCTCCCCATCGCGCACC<br>AGGACTGGCTGAGGGGCAAGGAGTTCAAG<br>TGCAAAGTCCACAACAAGGCACTCCCGGC<br>CCCCATCGAGAAAACCATCTCCAAAGCCA<br>GAGGGCAGCCCCTGGAGCCGAAGGTCTAC<br>ACCATGGGCCCTCCCCGGGAGGAGCTGAG<br>CAGCAGGTCGGTCAGCCTGACCTGCATGA<br>TCAACGGCTTCTACCCTTCCGACATCTCGG<br>TGGAGTGGGAGAAGAACGGGAAGGCAGA<br>GGACAACTACAAGACCACGCCGGCCGTGC<br>TGGACAGCGACGGCTCCTACTTCCTCTACA<br>GCAAGCTCTCAGTGCCCACGAGTGAGTGG<br>CAGCGGGGCGACGTCTTCACCTGCTCCGTG<br>ATGCACGAGGCCTTGCACAACCACTACAC<br>GCAGAAGTCCATCTCCCGCTCTCCGGGTAA<br>ATGA | KIP-8-78-4vh DNA |
| SEQ ID NO: 39 | METGLRWLLLVAVLKGVQCQSLEESGGDLV<br>KPEGSLTLTCTASGFSFSSSYWLCWVRQAPG<br>KGLEWIGCIDNSSGRTYRANWAKGRFTISRT<br>SSTTVTLQMTRLTAADTATYFCARGIDSYLW<br>GPGTLVTVSS<br>GQPKAPSVFPLAPCCGDTPSSTVTLGCLVKG<br>YLPEPVTVTWNSGTLTNGVRTFPSVRQSSGL<br>YSLSSVVSVTSSSQPVTCNVAHPATNTKVDK<br>TVAPSTCSKPTCPPPELLGGPSVFIFPPKPKDT<br>LMISRTPEVTCVVVDVSQDDPEVQFTWYINN<br>EQVRTARPPLREQQFNSTIRVVSTLPIAHQD<br>WLRGKEFKCKVHNKALPAPIEKTISKARGQP | KIP-8-124-4vh |

TABLE C-continued

| SEQ ID NO: | Sequence | Description |
|---|---|---|
| | LEPKVYTMGPPREELSSRSVSLTCMINGFYPS DISVEWEKNGKAEDNYKTTPAVLDSDGSYF LYSKLSVPTSEWQRGDVFTCSVMHEALHNH YTQKSISRSPGK | |
| SEQ ID NO: 40 | METGLRWLLLVAVLKGVQCQSLEESGGDLV KPGASLTLTCTASGFTLSSNYWICWVRQAPG KGLKWIACIDNSDGGTYYANWAKGRFTISK TSSTTVTLRMPSLTAADTAAYFCARGIDTYV WGPGTLVTVSS GQPKAPSVFPLAPCCGDTPSSTVTLGCLVKG YLPEPVTVTWNSGTLTNGVRTFPSVRQSSGL YSLSSVVSVTSSQPVTCNVAHPATNTKVDK TVAPSTCSKPTCPPPELLGGPSVFIFPPKPKDT LMISRTPEVTCVVVDVSQDDPEVQFTWYINN EQVRTARPPLREQQFNSTIRVVSTLPIAHQD WLRGKEFKCKVHNKALPAPIEKTISKARGQP LEPKVYTMGPPREELSSRSVSLTCMINGFYPS DISVEWEKNGKAEDNYKTTPAVLDSDGSYF LYSKLSVPTSEWQRGDVFTCSVMHEALHNH YTQKSISRSPGK | KIP-8-147-2vh |
| SEQ ID NO: 41 | MDTRAPTQLLGLLLLWLPGATFAQVLTQTP ASVSAAVGGTVTINCQASQSVYSSNLLTWY QKKPGQPPKLLIYEASKLPSGIPSRFSGSGSGT QFTLTISDVQCADAATYYCLGIYDCVLADCQ AFGGGTEVVVK GDPVAPTVLIFPPAADQVATGTVTIVCVANK YPPDVTVTWEVDGTTQTTGIENSKTPQNSAD CTYNLSSTLTLTSTQYNSHKEYTCKVTQGTT SVVQSFNRGDC | KIP-8-33-8vk |
| SEQ ID NO: 42 | ATGGACACGAGGGCCCCCACTCAGCTGCT GGGGCTCCTGCTGCTCTGGCTCCCAGGTGC CACATTTGCCCAAGTGCTGACCCAGACTCC AGCCTCGGTGTCTGCAGCTGTGGGAGGCA CAGTCACCATCAACTGCCAGGCCAGTCAG AGTGTTTATAGCAGCAACCTCTTAACCTGG TATCAGAAGAAACCAGGGCAGCCTCCCAA GCTCCTGATCTACGAAGCATCCAAACTGCC ATCTGGGATCCCATCGCGCTTCAGCGGCAG TGGATCTGGGACACAGTTCACTCTCACCAT CAGCGACGTACAGTGTGCCGATGCTGCCA CTTACTACTGTCTAGGCATTTATGATTGTG TGCTTGCTGATTGTCAGGCTTTCGGCGGAG GGACCGAAGTGGTGGTCAAA GGTGATCCAGTTGCACCTACTGTCCTCATC TTCCCACCAGCTGCTGATCAGGTGGCAACT GGAACAGTCACCATCGTGTGTGTGGCGAA TAAATACTTTCCCGATGTCACCGTCACCTG GGAGGTGGATGGCACCACCCAAACAACTG GCATCGAGAACAGTAAAACACCGCAGAAT TCTGCAGATTGTACCTACAACCTCAGCAGC ACTCTGACACTGACCAGCACACAGTACAA CAGCCACAAAGAGTACACCTGCAAGGTGA CCCAGGGCACGACCTCAGTCGTCCAGAGC TTCAATAGGGGTGACTGTTAG | KIP-8-33-8vk DNA |
| SEQ ID NO: 43 | MDTRAPTQLLGLLLLWLPGATFAQVLTQTP ASVSAAVGGTVTINCQASQSVYSSNLLTWY QKKPGQPPKLLIYEASKLPSGIPSRFSGSGSGT QFTLTISDVQCADAATYYCLGIYDCVLADCQ AFGGGTEVVVK GDPVAPTVLIFPPAADQVATGTVTIVCVANK YPPDVTVTWEVDGTTQTTGIENSKTPQNSAD CTYNLSSTLTLTSTQYNSHKEYTCKVTQGTT SVVQSFNRGDC | KIP-8-39-4vk |
| SEQ ID NO: 44 | ATGGACACGAGGGCCCCCACTCAGCTGCT GGGGCTCCTGCTGCTCTGGCTCCCAGGTGC CACATTTGCCCAAGTGCTGACCCAGACTCC AGCCTCGGTGTCTGCAGCTGTGGGAGGCA CAGTCACCATCAACTGCCAGGCCAGTCAG AGTGTTTATAGCAGCAACCTCTTAACCTGG TATCAGAAGAAACCAGGGCAGCCTCCCAA GCTCCTGATCTACGAAGCATCCAAACTGCC ATCTGGGATCCCATCGCGCTTCAGCGGCAG TGGATCTGGGACACAGTTCACTCTCACCAT | KIP-8-39-4vk DNA |

TABLE C-continued

| SEQ ID NO: | Sequence | Description |
|---|---|---|
| | CAGCGACGTACAGTGTGCCGATGCTGCCA<br>CTTACTACTGTCTAGGCATTTATGATTGTG<br>TGCTTGCTGATTGTCAGGCTTTCGGCGGAG<br>GGACCGAAGTGGTGGTCAAA<br>GGTGATCCAGTTGCACCTACTGTCCTCATC<br>TTCCCACCAGCTGCTGATCAGGTGGCAACT<br>GGAACAGTCACCATCGTGTGTGTGGCGAA<br>TAAATACTTTCCCGATGTCACCGTCACCTG<br>GGAGGTGGATGGCACCACCCAAACAACTG<br>GCATCGAGAACAGTAAAACACCGCAGAAT<br>TCTGCAGATTGTACCTACAACCTCAGCAGC<br>ACTCTGACACTGACCAGCACACAGTACAA<br>CAGCCACAAAGAGTACACCTGCAAGGTGA<br>CCCAGGGCACGACCTCAGTCGTCCAGAGC<br>TTCAATAGGGGTGACTGTTAG | |
| SEQ ID NO: 45 | MDTRAPTQLLGLLLLWLPGATFAQVLTQTP<br>ASVSAAVGGTVTINCQASQSVYSSNLLTWY<br>QKKPGQPPKLLIYEASKLPSGIPSRFSGSGSGT<br>QFTLTISDVQCADAATYYCLGIYDCVLADCQ<br>AFGGGTEVVVK<br>GDPVAPTVLIFPPAADQVATGTVTIVCVANK<br>YFPDVTVTWEVDGTTQTTGIENSKTPQNSAD<br>CTYNLSSTLTLTSTQYNSHKEYTCKVTQGTT<br>SVVQSFNRGDC | KIP-8-78-4vk |
| SEQ ID NO: 46 | ATGGACACGAGGGCCCCCACTCAGCTGCT<br>GGGGCTCCTGCTGCTCTGGCTCCCAGGTGC<br>CACATTTGCCCAAGTGCTGACCCAGACTCC<br>AGCCTCGGTGTCTGCAGCTGTGGGAGGCA<br>CAGTCACCATCAACTGCCAGGCCAGTCAG<br>AGTGTTTATAGCAGCAACCTCTTAACCTGG<br>TATCAGAAGAAACCAGGGCAGCCTCCCAA<br>GCTCCTGATCTACGAAGCATCCAAACTGCC<br>ATCTGGGATCCCATCGCGCTTCAGCGGCAG<br>TGGATCTGGGACACAGTTCACTCTCACCAT<br>CAGCGACGTACAGTGTGCCGATGCTGCCA<br>CTTACTACTGTCTAGGCATTTATGATTGTG<br>TGCTTGCTGATTGTCAGGCTTTCGGCGGAG<br>GGACCGAAGTGGTGGTCAAA<br>GGTGATCCAGTTGCACCTACTGTCCTCATC<br>TTCCCACCAGCTGCTGATCAGGTGGCAACT<br>GGAACAGTCACCATCGTGTGTGTGGCGAA<br>TAAATACTTTCCCGATGTCACCGTCACCTG<br>GGAGGTGGATGGCACCACCCAAACAACTG<br>GCATCGAGAACAGTAAAACACCGCAGAAT<br>TCTGCAGATTGTACCTACAACCTCAGCAGC<br>ACTCTGACACTGACCAGCACACAGTACAA<br>CAGCCACAAAGAGTACACCTGCAAGGTGA<br>CCCAGGGCACGACCTCAGTCGTCCAGAGC<br>TTCAATAGGGGTGACTGTTAG | KIP-8-78-4vk DNA |
| SEQ ID NO: 47 | MDTRAPTQLLGLLLLWLPGATFAQVLTQTPS<br>SVSAAVGGTVTINCQSSQSVVNTNYLGWYQ<br>QKPGQPPKLLIYQASKLVSGVPSRFSGSGSGT<br>QFTLTISDLECDDAATYYCVGTYDCNRSDCG<br>AFGGGTEVVVK<br>GDPVAPTVLIFPPAADQVATGTVTIVCVANK<br>YFPDVTVTWEVDGTTQTTGIENSKTPQNSAD<br>CTYNLSSTLTLTSTQYNSHKEYTCKVTQGTT<br>SVVQSFNRGDC | KIP-8-124-4vk |
| SEQ ID NO: 48 | ATGGACACGAGGGCCCCCACTCAGCTGCT<br>GGGGCTCCTGCTGCTCTGGCTCCCAGGTGC<br>CACATTTGCTCAAGTGCTGACCCAGACTCC<br>ATCCTCCGTGTCTGCAGCTGTGGGAGGCAC<br>AGTCACCATCAATTGCCAGTCCAGTCAGA<br>GTGTTGTTAATACTAACTATTTAGGCTGGT<br>ATCAGCAGAAACCAGGGCAGCCTCCCAAG<br>CTCCTGATCTACCAGGCATCCAAACTAGTA<br>TCTGGGGTCCCATCGCGGTTCAGTGGCAGT<br>GGATCTGGGACACAGTTCACTCTCACCATC<br>AGCGACCTGGAGTGTGACGATGCTGCCAC<br>TTACTACTGTGTAGGCACTTATGATTGTAA<br>TAGAAGCGATTGTGGGCTTTCGGCGGAG<br>GGACCGAGGTGGTGGTCAAA<br>GGTGATCCAGTTGCACCTACTGTCCTCATC<br>TTCCCACCAGCTGCTGATCAGGTGGCAACT | KIP-8-124-4vk DNA |

TABLE C-continued

| SEQ ID NO: | Sequence | Description |
| --- | --- | --- |
| | GGAACAGTCACCATCGTGTGTGTGGCGAA<br>TAAATACTTTCCCGATGTCACCGTCACCTG<br>GGAGGTGGATGGCACCACCCAAACAACTG<br>GCATCGAGAACAGTAAAACACCGCAGAAT<br>TCTGCAGATTGTACCTACAACCTCAGCAGC<br>ACTCTGACACTGACCAGCACACAGTACAA<br>CAGCCACAAAGAGTACACCTGCAAGGTGA<br>CCCAGGGCACGACCTCAGTCGTCCAGAGC<br>TTCAATAGGGGTGACTGTTAG | |
| SEQ ID NO: 49 | MDTRAPTQLLGLLLLWLPGATFAQVLTQTPS<br>SVSAAVGGTVTINCQSSQSVVTNKYLGWYQ<br>QKPGQPPKLLIYQASRLPSGVSSRFSGSGFGT<br>QFTLTISDVQCDDAATYYCVGTYDCKRADC<br>GAFGGGTEVVVK<br>GDPVAPTVLIFPPAADQVATGTVTIVCVANK<br>YFPDVTVTWEVDGTTQTTGIENSKTPQNSAD<br>CTYNLSSTLTLTSTQYNSHKEYTCKVTQGTT<br>SVVQSFNRGDC | KIP-8-147-2vk |
| SEQ ID NO: 50 | ATGGACACGAGGGCCCCCACTCAGCTGCT<br>GGGGCTCCTGCTGCTCTGGCTCCCAGGTGC<br>CACATTTGCTCAAGTGCTGACCCAGACTCC<br>ATCCTCCGTGTCTGCAGCTGTGGGAGGCAC<br>AGTCACCATCAATTGCCAGTCCAGTCAGA<br>GTGTTGTTACTAATAAGTACTTAGGCTGGT<br>ATCAGCAGAAACCAGGGCAGCCTCCCAAG<br>CTCCTGATCTACCAGGCATCCAGACTGCCA<br>TCTGGGGTCTCATCGCGCTTCAGCGGCAGT<br>GGATTTGGGACACAGTTCACTCTCACCATC<br>AGCGACGTGCAGTGTGACGATGCTGCCAC<br>TTACTACTGTGTAGGCACTTATGATTGTAA<br>ACGTGCTGACTGTGGGGCTTTCGGCGGAG<br>GGACCGAGGTGGTGGTCAAA<br>GGTGATCCAGTTGCACCTACTGTCCTCATC<br>TTCCCACCAGCTGCTGATCAGGTGGCAACT<br>GGAACAGTCACCATCGTGTGTGTGGCGAA<br>TAAATACTTTCCCGATGTCACCGTCACCTG<br>GGAGGTGGATGGCACCACCCAAACAACTG<br>GCATCGAGAACAGTAAAACACCGCAGAAT<br>TCTGCAGATTGTACCTACAACCTCAGCAGC<br>ACTCTGACACTGACCAGCACACAGTACAA<br>CAGCCACAAAGAGTACACCTGCAAGGTGA<br>CCCAGGGCACGACCTCAGTCGTCCAGAGC<br>TTCAATAGGGGTGACTGTTAG | KIP-8-147-2vk DNA |
| SEQ ID NO: 51 | ATGGAGACTGGGCTGCGCTGGCTTCTCCTG<br>GTCGCTGTGCTCAAAGGTGTCCAGTGTCAG<br>TCGTTGGAGGAGTCCGGGGGAGACCTGGT<br>CAAGCCTGAGGGATCCCTGACACTCACCT<br>GCACAGCCTCTGGATTCTCCTTCAGTAGCA<br>GCTACTGGCTATGTTGGGTCCGCCAGGCTC<br>CAGGGAAGGGGCTGGAGTGGATCGGATGC<br>ATTGATAATAGTAGTGGTAGGACTTACCGC<br>GCGAACTGGGCGAAAGGCCGATTCACCAT<br>CTCCAGAACCTCGTCGACCACGGTGACTCT<br>GCAAATGACCCGTCTGACAGCCGCGGACA<br>CGGCCACCTATTTCTGTGCGAGAGGAATTG<br>ATAGTTATTTGTGGGGCCCGGGCACCCTGG<br>TCACCGTCTCCTCA<br>GGGCAACCTAAGGCTCCATCAGTCTTCCCA<br>CTGGCCCCCTGCTGCGGGGACACACCCAG<br>CTCCACGGTGACCCTGGGCTGCCTGGTCAA<br>AGGGTACCTCCCGGAGCCAGTGACCGTGA<br>CCTGGAACTCGGGCACCCTCACCAATGGG<br>GTACGCACCTTCCCGTCCGTCGGCAGTCC<br>TCAGGCCTCTACTCGCTGAGCAGCGTGGTG<br>AGCGTGACCTCAAGCAGCCAGCCCGTCAC<br>CTGCAACGTGGCCCACCCAGCCACCAACA<br>CCAAAGTGGACAAGACCGTTGCGCCCTCG<br>ACATGCAGCAAGCCCACGTGCCCACCCCC<br>TGAACTCCTGGGGGGACCGTCTGTCTTCAT<br>CTTCCCCCCAAAACCCAAGGACACCCTCAT<br>GATCTCACGCACCCCCGAGGTCACATGCGT<br>GGTGGTGGACGTGAGCCAGGATGACCCCG<br>AGGTGCAGTTCACATGGTACATAAACAAC<br>GAGCAGGTGCGCACCCGCCCGGCCGCCGCT<br>ACGGGAGCAGCAGTTCAACAGCACGATCC | KIP-8-124-4vh DNA |

TABLE C-continued

| SEQ ID NO: | Sequence | Description |
|---|---|---|
| | GCGTGGTCAGCACCCTCCCCATCGCGCACC<br>AGGACTGGCTGAGGGGCAAGGAGTTCAAG<br>TGCAAAGTCCACAACAAGGCACTCCCGGC<br>CCCCATCGAGAAAACCATCTCCAAAGCCA<br>GAGGGCAGCCCCTGGAGCCGAAGGTCTAC<br>ACCATGGGCCCTCCCCGGGAGGAGCTGAG<br>CAGCAGGTCGGTCAGCCTGACCTGCATGA<br>TCAACGGCTTCTACCCTTCCGACATCTCGG<br>TGGAGTGGGAGAAGAACGGGAAGGCAGA<br>GGACAACTACAAGACCACGCCGGCCGTGC<br>TGGACAGCGACGGCTCCTACTTCCTCTACA<br>GCAAGCTCTCAGTGCCCACGAGTGAGTGG<br>CAGCGGGGCGACGTCTTCACCTGCTCCGTG<br>ATGCACGAGGCCTTGCACAACCACTACAC<br>GCAGAAGTCCATCTCCCGCTCTCCGGGTAA<br>ATGA | |
| SEQ ID NO: 52 | ATGGAGACTGGGCTGCGCTGGCTTCTCCTG<br>GTCGCTGTGCTCAAAGGTGTCCAGTGTCAG<br>TCGTTGGAGGAGTCCGGGGGAGACCTGGT<br>CAAGCCTGGGGCATCCCTGACACTCACCTG<br>CACAGCCTCTGGATTCACCCTCAGTAGCAA<br>CTACTGGATATGCTGGGTCCGCCAGGCTCC<br>AGGGAAGGGCCTGAAGTGGATCGCATGTA<br>TTGATAATAGTGATGGCGGCACTTACTACG<br>CGAACTGGGCGAAAGGCCGATTCACCATC<br>TCCAAAACCTCGTCGACCACGGTGACTCTG<br>CGAATGCCCAGTCTGACAGCCGCGGACAC<br>GGCCGCCTATTTCTGTGCGCGAGGAATTGA<br>TACGTACGTGTGGGGCCCAGGCACCCTGG<br>TCACCGTCTCCTCA<br>GGGCAACCTAAGGCTCCATCAGTCTTCCCA<br>CTGGCCCCCTGCTGCGGGACACACCCAG<br>CTCCACGGTGACCCTGGGCTGCCTGGTCAA<br>AGGGTACCTCCCGGAGCCAGTGACCGTGA<br>CCTGGAACTCGGGCACCCTCACCAATGGG<br>GTACGCACCTTCCCGTCCGTCGGCAGTCC<br>TCAGGCCTCTACTCGCTGAGCAGCGTGGTG<br>AGCGTGACCTCAAGCAGCCAGCCCGTCAC<br>CTGCAACGTGGCCCACCCAGCCACCAACA<br>CCAAAGTGGACAAGACCGTTGCGCCCTCG<br>ACATGCAGCAAGCCCACGTGCCCACCCCC<br>TGAACTCCTGGGGGGACCGTCTGTCTTCAT<br>CTTCCCCCCAAAACCCAAGGACACCCTCAT<br>GATCTCACGCACCCCCGAGGTCACATGCGT<br>GGTGGTGGACGTGAGCCAGGATGACCCCG<br>AGGTGCAGTTCACATGGTACATAAACAAC<br>GAGCAGGTGCGCACCGCCCGGCCGCCGCT<br>ACGGGAGCAGCAGTTCAACAGCACGATCC<br>GCGTGGTCAGCACCCTCCCCATCGCGCACC<br>AGGACTGGCTGAGGGGCAAGGAGTTCAAG<br>TGCAAAGTCCACAACAAGGCACTCCCGGC<br>CCCCATCGAGAAAACCATCTCCAAAGCCA<br>GAGGGCAGCCCCTGGAGCCGAAGGTCTAC<br>ACCATGGGCCCTCCCCGGGAGGAGCTGAG<br>CAGCAGGTCGGTCAGCCTGACCTGCATGA<br>TCAACGGCTTCTACCCTTCCGACATCTCGG<br>TGGAGTGGGAGAAGAACGGGAAGGCAGA<br>GGACAACTACAAGACCACGCCGGCCGTGC<br>TGGACAGCGACGGCTCCTACTTCCTCTACA<br>GCAAGCTCTCAGTGCCCACGAGTGAGTGG<br>CAGCGGGGCGACGTCTTCACCTGCTCCGTG<br>ATGCACGAGGCCTTGCACAACCACTACAC<br>GCAGAAGTCCATCTCCCGCTCTCCGGGTAA<br>ATGA | KIP-8-147-2vh DNA |
| SEQ ID NO: 53 | TLTADSPVDSSPYTADE | KIP-8B reversed |

What is claimed is:

1. An isolated antigen binding molecule that specifically binds to a polypeptide comprising the alpha chain of the constant region of a T cell receptor (TCR), said isolated antigen binding molecule comprising:
   (a) a VH CDR1 region comprising the amino acid sequence of SEQ ID NO: 25;
   (b) a VH CDR2 region comprising the amino acid sequence of SEQ ID NO: 26;
   (c) a VH CDR3 region comprising the amino acid sequence of SEQ ID NO: 24;
   (d) a VL CDR1 region comprising the amino acid sequence of SEQ ID NO: 19;
   (e) a VL CDR2 region comprising the amino acid sequence of SEQ ID NO: 20; and
   (f) a VL CDR3 region comprising the amino acid sequence of SEQ ID NO: 21.

2. The antigen binding molecule of claim 1, wherein the TCR is a murine TCR.

3. The isolated antigen binding molecule of claim 1, wherein the polypeptide comprising the alpha chain of the constant region of the T cell receptor is an engineered T cell receptor.

4. The isolated antigen binding molecule of claim 1, wherein the antigen binding molecule is selected from the group consisting of an antibody, an scFv, a Fab, a Fab', a Fv, a F(ab')2, and a dAb.

5. The isolated antigen binding molecule of claim 1, comprising a heavy chain variable region (VH) sequence of SEQ ID NO: 1 or SEQ ID NO: 7.

6. An isolated antigen binding molecule, comprising a VH amino acid sequence that is at least about 90%, at least about 95%, at least about 96%, at least about 97%, at least about 98%, at least about 99%, or about 100% identical to a VH of an antigen binding molecule of claim 5.

7. The isolated antigen binding molecule of claim 1, comprising a light chain variable region (VL) sequence comprising SEQ ID NO: 13.

8. An isolated antigen binding molecule, comprising a VL amino acid sequence that is at least about 90%, at least about 95%, at least about 96%, at least about 97%, at least about 98%, at least about 99%, or about 100% identical to a VL of an antigen binding molecule of claim 7.

9. The isolated antigen binding molecule of claim 1, comprising:
 (a) a VH comprising the amino acid sequence of SEQ ID NO: 1; and
 (b) a VL comprising the amino acid sequence of SEQ ID NO: 13.

10. The isolated antigen binding molecule of claim 9 comprising:
 (a) a heavy chain comprising the amino acid sequence of SEQ ID NO: 5; and
 (b) a light chain comprising the amino acid sequence of SEQ ID NO: 17.

11. The isolated antigen binding molecule of claim 1, comprising:
 (a) a VH comprising the amino acid sequence of SEQ ID NO: 7; and
 (b) a VL comprising the amino acid sequence of SEQ ID NO: 13.

12. The isolated antigen binding molecule of claim 11, comprising:
 (a) a heavy chain comprising the amino acid sequence of SEQ ID NO: 11; and
 (b) a light chain comprising the amino acid sequence of SEQ ID NO: 17.

13. The isolated antigen binding molecule of claim 1, further comprising a detectable label.

14. A composition comprising the isolated antigen binding molecule of claim 1.

15. A method of determining a number of cells presenting a polypeptide comprising the alpha chain of the constant region of a T cell receptor, wherein the method comprises:
 (a) providing a sample comprising cells known or suspected to be presenting a polypeptide comprising the alpha chain of the constant region of the T cell receptor;
 (b) contacting the sample with the isolated antigen binding molecule of claim 1 under conditions that permit binding of the polypeptide and the antigen binding molecule; and
 (c) determining the number of cells presenting the polypeptide in the sample.

16. A method of determining the presence or absence of a polypeptide comprising the alpha chain of the constant region of a T cell receptor, wherein the method comprises:
 (a) providing a sample known or suspected to comprise a polypeptide comprising the alpha chain of the constant region of the T cell receptor;
 (b) contacting the sample with the isolated antigen binding molecule of claim 1 under conditions that permit binding of the polypeptide and the antigen binding molecule; and
 (c) detecting the presence or absence of a polypeptide: antigen binding molecule complex.

17. The method of claim 15, wherein the sample is a formalin-fixed sample.

18. The method of claim 15, further comprising contacting the sample with an antibody to a cell surface marker selected from the group consisting of CD4, CD8 and PD-L1.

* * * * *

SEQUENCE LISTING

<160> NUMBER OF SEQ ID NOS: 53

<210> SEQ ID NO 1

```
<211> LENGTH: 131
<212> TYPE: PRT
<213> ORGANISM: Artificial Sequence
<220> FEATURE:
<223> OTHER INFORMATION: antigen binding molecule

<400> SEQUENCE: 1

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Thr Ala Ser Gly Phe Asp Leu
        35                  40                  45

Gly Asn Asn Trp Ile His Trp Val Arg His Ala Pro Gly Lys Gly Leu
    50                  55                  60

Glu Trp Ile Ala Cys Val Ser Gly Ser Ser Gly Asn Ile Tyr Tyr Ala
65                  70                  75                  80

Thr Trp Ala Lys Gly Arg Phe Thr Met Ser Lys Ala Ser Ser Thr Thr
                85                  90                  95

Val Thr Leu Arg Met Thr Ser Leu Thr Ala Ala Asp Thr Ala Thr Tyr
            100                 105                 110

Phe Cys Ala Arg Gly Trp Asn Leu Trp Gly Pro Gly Thr Leu Val Thr
        115                 120                 125

Val Ser Ser
    130

<210> SEQ ID NO 2
<211> LENGTH: 393
<212> TYPE: DNA
<213> ORGANISM: Artificial Sequence
<220> FEATURE:
<223> OTHER INFORMATION: antigen binding molecule

<400> SEQUENCE: 2
atggagactg ggctgcgctg gcttctcctg gtcgctgtgc tcaaaggtgt ccagtgtcag      60
gaacagctgg tggagtccgg gggaggcctg gtccagcctg agggatccct gacactcacc     120
tgcacagcct ctggattcga cctcggtaac aactggatac actgggtccg ccacgctcca     180
gggaagggac tggaatggat cgcatgcgtt agtggtagta gcggcaacat ttactacgcg     240
acttgggcga aaggccgatt caccatgtcc aaagcctcgt cgaccacggt gactctacga     300
atgaccagtc tgacagccgc ggacacggcc acctatttct gtgcgagagg atggaacttg     360
tggggcccag gcaccctggt caccgtctcc tca                                  393

<210> SEQ ID NO 3
<211> LENGTH: 323
<212> TYPE: PRT
<213> ORGANISM: Artificial Sequence
<220> FEATURE:
<223> OTHER INFORMATION: antigen binding molecule

<400> SEQUENCE: 3

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
```

```
                50              55              60
Leu Ser Ser Val Val Ser Val Thr Ser Ser Gln Pro Val Thr Cys
65              70              75              80

Asn Val Ala His Pro Ala Thr Asn Thr Lys Val Asp Lys Thr Val Ala
                85              90              95

Pro Ser Thr Cys Ser Lys Pro Thr Cys Pro Pro Glu Leu Leu Gly
            100             105             110

Gly Pro Ser Val Phe Ile Phe Pro Pro Lys Pro Lys Asp Thr Leu Met
        115             120             125

Ile Ser Arg Thr Pro Glu Val Thr Cys Val Val Val Asp Val Ser Gln
130             135             140

Asp Asp Pro Glu Val Gln Phe Thr Trp Tyr Ile Asn Asn Glu Gln Val
145             150             155             160

Arg Thr Ala Arg Pro Pro Leu Arg Glu Gln Gln Phe Asn Ser Thr Ile
            165             170             175

Arg Val Val Ser Thr Leu Pro Ile Ala His Gln Asp Trp Leu Arg Gly
            180             185             190

Lys Glu Phe Lys Cys Lys Val His Asn Lys Ala Leu Pro Ala Pro Ile
        195             200             205

Glu Lys Thr Ile Ser Lys Ala Arg Gly Gln Pro Leu Glu Pro Lys Val
210             215             220

Tyr Thr Met Gly Pro Pro Arg Glu Glu Leu Ser Ser Arg Ser Val Ser
225             230             235             240

Leu Thr Cys Met Ile Asn Gly Phe Tyr Pro Ser Asp Ile Ser Val Glu
            245             250             255

Trp Glu Lys Asn Gly Lys Ala Glu Asp Asn Tyr Lys Thr Thr Pro Ala
        260             265             270

Val Leu Asp Ser Asp Gly Ser Tyr Phe Leu Tyr Ser Lys Leu Ser Val
        275             280             285

Pro Thr Ser Glu Trp Gln Arg Gly Asp Val Phe Thr Cys Ser Val Met
290             295             300

His Glu Ala Leu His Asn His Tyr Thr Gln Lys Ser Ile Ser Arg Ser
305             310             315             320

Pro Gly Lys

<210> SEQ ID NO 4
<211> LENGTH: 972
<212> TYPE: DNA
<213> ORGANISM: Artificial Sequence
<220> FEATURE:
<223> OTHER INFORMATION: antigen binding molecule

<400> SEQUENCE: 4
gggcaaccta aggctccatc agtcttccca ctggcccct gctgcgggga cacacccagc    60
tccacggtga ccctgggctg cctggtcaaa gggtacctcc ggagccagt gaccgtgacc   120 tggaactcgg gcaccctcac caatgggta cgcaccttcc cgtccgtccg gcagtcctca   180
ggcctctact cgctgagcag cgtggtgagc gtgacctcaa gcagccagcc cgtcacctgc   240
aacgtggccc accagccac caacaccaaa gtggacaaga ccgttgcgcc ctcgacatgc   300
agcaagccca cgtgcccacc ccctgaactc ctgggggac cgtctgtctt catcttcccc   360
ccaaaaccca aggacaccct catgatctca cgcacccccg aggtcacatg cgtggtggtg   420
gacgtgagcc aggatgaccc cgaggtgcag ttcacatggt acataaacaa cgagcaggtg   480
cgcaccgccc ggccgccgct acgggagcag cagttcaaca gcacgatccg cgtggtcagc   540
```

```
acccteccca tcgcgcacca ggactggctg aggggcaagg agttcaagtg caaagtccac    600
aacaaggcac tcccggcccc catcgagaaa accatctcca agccagagg  gcagccctg     660 gagccgaagg tctacaccat gggccctccc cgggaggagc tgagcagcag gtcggtcagc    720
ctgacctgca tgatcaacgg cttctaccct tccgacatct cggtggagtg ggagaagaac    780
gggaaggcag aggacaacta caagaccacg ccggccgtgc tggacagcga cggctcctac    840
ttcctctaca gcaagctctc agtgcccacg agtgagtggc agcggggcga cgtcttcacc    900
tgctccgtga tgcacgaggc cttgcacaac cactacacgc agaagtccat ctcccgctct    960
ccgggtaaat ga                                                        972
```

```
<210> SEQ ID NO 5
<211> LENGTH: 454
<212> TYPE: PRT
<213> ORGANISM: Artificial Sequence
<220> FEATURE:
<223> OTHER INFORMATION: antigen binding molecule

<400> SEQUENCE: 5
```

| | | | | | | | | | | | | | | | |
|---|---|---|---|---|---|---|---|---|---|---|---|---|---|---|---|
|Met|Glu|Thr|Gly|Leu|Arg|Trp|Leu|Leu|Leu|Val|Ala|Val|Leu|Lys|Gly|
|1| | | |5| | | | |10| | | | |15| |
|Val|Gln|Cys|Gln|Glu|Gln|Leu|Val|Glu|Ser|Gly|Gly|Gly|Leu|Val|Gln|
| | | |20| | | | |25| | | | |30| | |
|Pro|Glu|Gly|Ser|Leu|Thr|Leu|Thr|Cys|Thr|Ala|Ser|Gly|Phe|Asp|Leu|
| | | |35| | | | |40| | | | |45| | |
|Gly|Asn|Asn|Trp|Ile|His|Trp|Val|Arg|His|Ala|Pro|Gly|Lys|Gly|Leu|
| | |50| | | | |55| | | | |60| | | |
|Glu|Trp|Ile|Ala|Cys|Val|Ser|Gly|Ser|Ser|Gly|Asn|Ile|Tyr|Tyr|Ala|
|65| | | | |70| | | | |75| | | | |80|
|Thr|Trp|Ala|Lys|Gly|Arg|Phe|Thr|Met|Ser|Lys|Ala|Ser|Ser|Thr|Thr|
| | | | |85| | | | |90| | | | |95| | |
|Val|Thr|Leu|Arg|Met|Thr|Ser|Leu|Thr|Ala|Ala|Asp|Thr|Ala|Thr|Tyr|
| | | | |100| | | | |105| | | | |110| | |
|Phe|Cys|Ala|Arg|Gly|Trp|Asn|Leu|Trp|Gly|Pro|Gly|Thr|Leu|Val|Thr|
| | | |115| | | | |120| | | | |125| | | |
|Val|Ser|Ser|Gly|Gln|Pro|Lys|Ala|Pro|Ser|Val|Phe|Pro|Leu|Ala|Pro|
| | |130| | | | |135| | | | |140| | | | |
|Cys|Cys|Gly|Asp|Thr|Pro|Ser|Ser|Thr|Val|Thr|Leu|Gly|Cys|Leu|Val|
|145| | | | |150| | | | |155| | | | |160|
|Lys|Gly|Tyr|Leu|Pro|Glu|Pro|Val|Thr|Val|Thr|Trp|Asn|Ser|Gly|Thr|
| | | | |165| | | | |170| | | | |175| | |
|Leu|Thr|Asn|Gly|Val|Arg|Thr|Phe|Pro|Ser|Val|Arg|Gln|Ser|Ser|Gly|
| | | |180| | | | |185| | | | |190| | | |
|Leu|Tyr|Ser|Leu|Ser|Ser|Val|Val|Ser|Val|Thr|Ser|Ser|Ser|Gln|Pro|
| | |195| | | | |200| | | | |205| | | | |
|Val|Thr|Cys|Asn|Val|Ala|His|Pro|Ala|Thr|Asn|Thr|Lys|Val|Asp|Lys|
| | |210| | | | |215| | | | |220| | | | |
|Thr|Val|Ala|Pro|Ser|Thr|Cys|Ser|Lys|Pro|Thr|Cys|Pro|Pro|Pro|Glu|
|225| | | | |230| | | | |235| | | | |240| |
|Leu|Leu|Gly|Gly|Pro|Ser|Val|Phe|Ile|Phe|Pro|Pro|Lys|Pro|Lys|Asp|
| | | | |245| | | | |250| | | | |255| | |
|Thr|Leu|Met|Ile|Ser|Arg|Thr|Pro|Glu|Val|Thr|Cys|Val|Val|Val|Asp|
| | | |260| | | | |265| | | | |270| | | |
|Val|Ser|Gln|Asp|Asp|Pro|Glu|Val|Gln|Phe|Thr|Trp|Tyr|Ile|Asn|Asn|

```
                    275                 280                 285
Glu Gln Val Arg Thr Ala Arg Pro Pro Leu Arg Glu Gln Gln Phe Asn
    290                 295                 300
Ser Thr Ile Arg Val Val Ser Thr Leu Pro Ile Ala His Gln Asp Trp
305                 310                 315                 320
Leu Arg Gly Lys Glu Phe Lys Cys Lys Val His Asn Lys Ala Leu Pro
                325                 330                 335
Ala Pro Ile Glu Lys Thr Ile Ser Lys Ala Arg Gly Gln Pro Leu Glu
            340                 345                 350
Pro Lys Val Tyr Thr Met Gly Pro Pro Arg Glu Glu Leu Ser Ser Arg
        355                 360                 365
Ser Val Ser Leu Thr Cys Met Ile Asn Gly Phe Tyr Pro Ser Asp Ile
    370                 375                 380
Ser Val Glu Trp Glu Lys Asn Gly Lys Ala Glu Asp Asn Tyr Lys Thr
385                 390                 395                 400
Thr Pro Ala Val Leu Asp Ser Asp Gly Ser Tyr Phe Leu Tyr Ser Lys
                405                 410                 415
Leu Ser Val Pro Thr Ser Glu Trp Gln Arg Gly Asp Val Phe Thr Cys
            420                 425                 430
Ser Val Met His Glu Ala Leu His Asn His Tyr Thr Gln Lys Ser Ile
        435                 440                 445
Ser Arg Ser Pro Gly Lys
    450

<210> SEQ ID NO 6
<211> LENGTH: 1365
<212> TYPE: DNA
<213> ORGANISM: Artificial Sequence
<220> FEATURE:
<223> OTHER INFORMATION: antigen binding molecule

<400> SEQUENCE: 6
atggagactg ggctgcgctg gcttctcctg gtcgctgtgc tcaaaggtgt ccagtgtcag    60
gaacagctgg tggagtccgg gggaggcctg gtccagcctg agggatccct gacactcacc   120
tgcacagcct ctggattcga cctcggtaac aactggatac actgggtccg ccacgctcca   180
gggaagggac tggaatggat cgcatgcgtt agtggtagta gcggcaacat ttactacgcg   240
acttgggcga aaggccgatt caccatgtcc aaagcctcgt cgaccacggt gactctacga   300
atgaccagtc tgacagccgc ggacacggcc acctatttct gtgcgagagg atggaacttg   360
tggggcccag gcaccctggt caccgtctcc tcagggcaac taaggctcc atcagtcttc   420 ccactggccc cctgctgcgg ggacacaccc agctccacgg tgaccctggg ctgcctggtc   480
aaagggtacc tcccggagcc agtgaccgtg acctggaact cgggcaccct caccaatggg   540
gtacgcacct tcccgtccgt ccggcagtcc tcaggcctct actcgctgag cagcgtggtg   600
agcgtgacct caagcagcca gcccgtcacc tgcaacgtgg cccacccagc caccaacacc   660
aaagtggaca gaccgttgc gccctcgaca tgcagcaagc ccacgtgccc acccctgaa    720 ctcctggggg gaccgtctgt cttcatcttc cccccaaaac ccaaggacac cctcatgatc   780
tcacgcaccc ccgaggtcac atgcgtggtg gtggacgtga gccaggatga ccccgaggtg   840
cagttcacat ggtacataaa caacgagcag gtgcgcaccg cccggccgcc gctacgggag   900
cagcagttca acagcacgat ccgcgtggtc agcaccctcc ccatcgcgca ccaggactgg   960
ctgaggggca aggagttcaa gtgcaaagtc cacaacaagg cactcccggc ccccatcgag  1020
```

```
aaaaccatct ccaaagccag agggcagccc ctggagccga aggtctacac catgggccct      1080 cccccgggagg agctgagcag caggtcggtc agcctgacct gcatgatcaa cggcttctac      1140
ccttccgaca tctcggtgga gtgggagaag aacgggaagg cagaggacaa ctacaagacc      1200
acgccggccg tgctggacag cgacggctcc tacttcctct acagcaagct ctcagtgccc      1260
acgagtgagt ggcagcgggg cgacgtcttc acctgctccg tgatgcacga ggccttgcac      1320
aaccactaca cgcagaagtc catctcccgc tctccgggta aatga                      1365
```

```
<210> SEQ ID NO 7
<211> LENGTH: 131
<212> TYPE: PRT
<213> ORGANISM: Artificial Sequence
<220> FEATURE:
<223> OTHER INFORMATION: antigen binding molecule

<400> SEQUENCE: 7

Met Glu Thr Gly Leu Arg Trp Leu Leu Leu Val Ala Val Leu Lys Asp
1               5                   10                  15

Val Gln Cys Gln Glu Gln Leu Val Glu Ser Gly Gly Gly Leu Val Gln
                20                  25                  30

Pro Glu Gly Ser Leu Thr Leu Thr Cys Thr Ala Ser Gly Phe Asp Leu
            35                  40                  45

Gly Asn Asn Trp Ile His Trp Val Arg His Ala Pro Gly Lys Gly Leu
        50                  55                  60

Glu Trp Ile Ala Cys Val Ser Gly Ser Gly Asn Ile Tyr Tyr Ala
65                  70                  75                  80

Thr Trp Ala Lys Gly Arg Phe Thr Met Ser Lys Ala Ser Ser Thr Thr
                85                  90                  95

Val Thr Leu Arg Met Thr Ser Leu Thr Ala Ala Asp Thr Ala Thr Tyr
            100                 105                 110

Phe Cys Ala Arg Gly Trp Asn Leu Trp Gly Pro Gly Thr Leu Val Thr
        115                 120                 125

Val Ser Ser
    130
```

```
<210> SEQ ID NO 8
<211> LENGTH: 393
<212> TYPE: DNA
<213> ORGANISM: Artificial Sequence
<220> FEATURE:
<223> OTHER INFORMATION: antigen binding molecule

<400> SEQUENCE: 8
atggagactg gcctgcgctg gcttctcctg gtcgctgtgc tcaaagatgt ccagtgtcag       60
gaacagctgg tggagtccgg gggaggcctg gtccagcctg agggatccct gacactcacc      120
tgcacagcct ctggattcga cctcggtaac aactggatac actgggtccg ccacgctcca      180
gggaagggac tggaatggat cgcatgcgtt agtggtagta gcggcaacat ttactacgcg      240
acttgggcga aaggccgatt caccatgtcc aaagcctcgt cgaccacggt gactctacga      300
atgaccagtc tgacagccgc ggacacggcc acctatttct gtgcgagagg atggaacttg      360
tggggcccag gcaccctggt caccgtctcc tca                                    393
```

```
<210> SEQ ID NO 9
<211> LENGTH: 323
<212> TYPE: PRT
<213> ORGANISM: Artificial Sequence
<220> FEATURE:
```

<223> OTHER INFORMATION: antigen binding molecule

<400> SEQUENCE: 9

```
Gly Gln Pro Lys Ala Pro Ser Val Phe Pro Leu Ala Pro Cys Cys Gly
1               5                   10                  15
Asp Thr Pro Ser Ser Thr Val Thr Leu Gly Cys Leu Val Lys Gly Tyr
            20                  25                  30
Leu Pro Glu Pro Val Thr Val Thr Trp Asn Ser Gly Thr Leu Thr Asn
        35                  40                  45
Gly Val Arg Thr Phe Pro Ser Val Arg Gln Ser Ser Gly Leu Tyr Ser
    50                  55                  60
Leu Ser Ser Val Val Ser Val Thr Ser Ser Ser Gln Pro Val Thr Cys
65                  70                  75                  80
Asn Val Ala His Pro Ala Thr Asn Thr Lys Val Asp Lys Thr Val Ala
                85                  90                  95
Pro Ser Thr Cys Ser Lys Pro Thr Cys Pro Pro Pro Glu Leu Leu Gly
            100                 105                 110
Gly Pro Ser Val Phe Ile Phe Pro Pro Lys Pro Lys Asp Thr Leu Met
        115                 120                 125
Ile Ser Arg Thr Pro Glu Val Thr Cys Val Val Val Asp Val Ser Gln
    130                 135                 140
Asp Asp Pro Glu Val Gln Phe Thr Trp Tyr Ile Asn Asn Glu Gln Val
145                 150                 155                 160
Arg Thr Ala Arg Pro Pro Leu Arg Glu Gln Gln Phe Asn Ser Thr Ile
                165                 170                 175
Arg Val Val Ser Thr Leu Pro Ile Ala His Gln Asp Trp Leu Arg Gly
            180                 185                 190
Lys Glu Phe Lys Cys Lys Val His Asn Lys Ala Leu Pro Ala Pro Ile
        195                 200                 205
Glu Lys Thr Ile Ser Lys Ala Arg Gly Gln Pro Leu Glu Pro Lys Val
    210                 215                 220
Tyr Thr Met Gly Pro Pro Arg Glu Glu Leu Ser Ser Arg Ser Val Ser
225                 230                 235                 240
Leu Thr Cys Met Ile Asn Gly Phe Tyr Pro Ser Asp Ile Ser Val Glu
                245                 250                 255
Trp Glu Lys Asn Gly Lys Ala Glu Asp Asn Tyr Lys Thr Thr Pro Ala
            260                 265                 270
Val Leu Asp Ser Asp Gly Ser Tyr Phe Leu Tyr Ser Lys Leu Ser Val
        275                 280                 285
Pro Thr Ser Glu Trp Gln Arg Gly Asp Val Phe Thr Cys Ser Val Met
    290                 295                 300
His Glu Ala Leu His Asn His Tyr Thr Gln Lys Ser Ile Ser Arg Ser
305                 310                 315                 320
Pro Gly Lys
```

<210> SEQ ID NO 10
<211> LENGTH: 972
<212> TYPE: DNA
<213> ORGANISM: Artificial Sequence
<220> FEATURE:
<223> OTHER INFORMATION: antigen binding molecule

<400> SEQUENCE: 10

```
gggcaaccta aggctccatc agtcttccca ctggccccct gctgcgggga cacacccagc    60
tccacggtga ccctgggctg cctggtcaaa gggtacctcc cggagccagt gaccgtgacc   120
```

```
tggaactcgg gcaccctcac caatggggta cgcaccttcc cgtccgtccg gcagtcctca    180
ggcctctact cgctgagcag cgtggtgagc gtgacctcaa gcagccagcc cgtcacctgc    240
aacgtggccc acccagccac caacaccaaa gtggacaaga ccgttgcgcc ctcgacatgc    300
agcaagccca cgtgcccacc ccctgaactc ctgggggggac cgtctgtctt catcttcccc    360
ccaaaaccca aggacaccct catgatctca cgcacccccg aggtcacatg cgtggtggtg    420
gacgtgagcc aggatgaccc cgaggtgcag ttcacatggt acataaacaa cgagcaggtg    480
cgcaccgccc ggccgccgct acgggagcag cagttcaaca gcacgatccg cgtggtcagc    540
accctcccca tcgcgcacca ggactggctg aggggcaagg agttcaagtg caaagtccac    600
aacaaggcac tcccggcccc catcgagaaa accatctcca agccagagg cagcccctg    660 gagccgaagg tctacaccat gggccctccc cgggaggagc tgagcagcag gtcggtcagc    720
ctgacctgca tgatcaacgg cttctaccct tccgacatct cggtggagtg ggagaagaac    780
gggaaggcag aggacaacta caagaccacg ccggccgtgc tggacagcga cggctcctac    840
ttcctctaca gcaagctctc agtgcccacg agtgagtggc agcggggcga cgtcttcacc    900
tgctccgtga tgcacgaggc cttgcacaac cactacacgc agaagtccat ctcccgctct    960
ccgggtaaat ga                                                        972

<210> SEQ ID NO 11
<211> LENGTH: 454
<212> TYPE: PRT
<213> ORGANISM: Artificial Sequence
<220> FEATURE:
<223> OTHER INFORMATION: antigen binding molecule

<400> SEQUENCE: 11

Met Glu Thr Gly Leu Arg Trp Leu Leu Leu Val Ala Val Leu Lys Asp
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Thr Ala Ser Gly Phe Asp Leu
        35                  40                  45

Gly Asn Asn Trp Ile His Trp Val Arg His Ala Pro Gly Lys Gly Leu
    50                  55                  60

Glu Trp Ile Ala Cys Val Ser Gly Ser Ser Gly Asn Ile Tyr Tyr Ala
65                  70                  75                  80

Thr Trp Ala Lys Gly Arg Phe Thr Met Ser Lys Ala Ser Ser Thr Thr
                85                  90                  95

Val Thr Leu Arg Met Thr Ser Leu Thr Ala Ala Asp Thr Ala Thr Tyr
            100                 105                 110

Phe Cys Ala Arg Gly Trp Asn Leu Trp Gly Pro Gly Thr Leu Val Thr
        115                 120                 125

Val Ser Ser Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205
```

Val Thr Cys Asn Val Ala His Pro Ala Thr Asn Thr Lys Val Asp Lys
        210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Ser Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450

<210> SEQ ID NO 12
<211> LENGTH: 1365
<212> TYPE: DNA
<213> ORGANISM: Artificial Sequence
<220> FEATURE:
<223> OTHER INFORMATION: antigen binding molecule

<400> SEQUENCE: 12

```
atggagactg ggctgcgctg gcttctcctg gtcgctgtgc tcaaagatgt ccagtgtcag      60
gaacagctgg tggagtccgg gggaggcctg gtccagcctg agggatccct gacactcacc     120
tgcacagcct ctggattcga cctcggtaac aactggatac actgggtccg ccacgctcca     180
gggaagggac tggaatggat cgcatgcgtt agtggtagta gcggcaacat ttactacgcg     240
acttgggcga aaggccgatt caccatgtcc aaagcctcgt cgaccacggt gactctacga     300
atgaccagtc tgacagccgc ggacacggcc acctatttct gtgcgagagg atggaacttg     360
tggggcccag gcaccctggt caccgtctcc tcagggcaac taaggctcc  atcagtcttc     420 ccactggccc cctgctgcgg ggacacaccc agctccacgg tgaccctggg ctgcctggtc     480
aaagggtacc tcccggagcc agtgaccgtg acctggaact cgggcaccct caccaatggg     540
gtacgcacct tcccgtccgt ccggcagtcc tcaggcctct actcgctgag cagcgtggtg     600
```

-continued

| | |
|---|---|
| agcgtgacct caagcagcca gcccgtcacc tgcaacgtgg cccacccagc caccaacacc | 660 |
| aaagtggaca agaccgttgc gccctcgaca tgcagcaagc ccacgtgccc acccctgaa | 720 |
| ctcctggggg gaccgtctgt cttcatcttc cccccaaaac ccaaggacac cctcatgatc | 780 |
| tcacgcaccc ccgaggtcac atgcgtggtg gtggacgtga gccaggatga ccccgaggtg | 840 |
| cagttcacat ggtacataaa caacgagcag gtgcgcaccg cccggccgcc gctacgggag | 900 |
| cagcagttca acagcacgat ccgcgtggtc agcaccctcc ccatcgcgca ccaggactgg | 960 |
| ctgaggggca aggagttcaa gtgcaaagtc acaacaagg cactcccggc ccccatcgag | 1020 |
| aaaaccatct ccaaagccag agggcagccc ctggagccga aggtctacac catgggccct | 1080 |
| ccccgggagg agctgagcag caggtcggtc agcctgacct gcatgatcaa cggcttctac | 1140 |
| ccttccgaca tctcggtgga gtgggagaag aacgggaagg cagaggacaa ctacaagacc | 1200 |
| acgccggccg tgctggacag cgacggctcc tacttcctct acagcaagct ctcagtgccc | 1260 |
| acgagtgagt ggcagcgggg cgacgtcttc acctgctccg tgatgcacga ggccttgcac | 1320 |
| aaccactaca cgcagaagtc catctcccgc tctccgggta aatga | 1365 |

<210> SEQ ID NO 13
<211> LENGTH: 135
<212> TYPE: PRT
<213> ORGANISM: Artificial Sequence
<220> FEATURE:
<223> OTHER INFORMATION: antigen binding molecule

<400> SEQUENCE: 13

Met Asp Thr Arg Ala Pro Thr Gln Leu Leu Gly Leu Leu Leu Leu Trp
1               5                   10                  15
Leu Pro Gly Ala Thr Phe Ala Gln Val Leu Thr Gln Thr Pro Ala Ser
            20                  25                  30
Val Ser Ala Ala Val Gly Gly Thr Val Thr Ile Asn Cys Gln Ala Ser
        35                  40                  45
Gln Ser Val Tyr Ser Ser Asn Leu Leu Thr Trp Tyr Gln Lys Lys Pro
    50                  55                  60
Gly Gln Pro Pro Lys Leu Leu Ile Tyr Glu Ala Ser Lys Leu Pro Ser
65                  70                  75                  80
Gly Ile Pro Ser Arg Phe Ser Gly Ser Gly Ser Gly Thr Gln Phe Thr
                85                  90                  95
Leu Thr Ile Ser Asp Val Gln Cys Ala Asp Ala Ala Thr Tyr Tyr Cys
            100                 105                 110
Leu Gly Ile Tyr Asp Cys Val Leu Ala Asp Cys Gln Ala Phe Gly Gly
        115                 120                 125
Gly Thr Glu Val Val Val Lys
    130                 135

<210> SEQ ID NO 14
<211> LENGTH: 405
<212> TYPE: DNA
<213> ORGANISM: Artificial Sequence
<220> FEATURE:
<223> OTHER INFORMATION: antigen binding molecule

<400> SEQUENCE: 14

| | |
|---|---|
| atggacacga gggcccccac tcagctgctg gggctcctgc tgctctggct cccaggtgcc | 60 |
| acatttgccc aagtgctgac ccagactcca gcctcggtgt ctgcagctgt ggaggcaca | 120 |
| gtcaccatca actgccaggc cagtcagagt gtttatagca gcaacctctt aacctggtat | 180 |

```
cagaagaaac cagggcagcc tcccaagctc ctgatctacg aagcatccaa actgccatct    240
gggatcccat cgcgcttcag cggcagtgga tctgggacac agttcactct caccatcagc    300
gacgtacagt gtgccgatgc tgccacttac tactgtctag catttatga ttgtgtgctt    360 gctgattgtc aggctttcgg cggagggacc gaagtggtgg tcaaa                   405
```

```
<210> SEQ ID NO 15
<211> LENGTH: 104
<212> TYPE: PRT
<213> ORGANISM: Artificial Sequence
<220> FEATURE:
<223> OTHER INFORMATION: antigen binding molecule

<400> SEQUENCE: 15
```

```
Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100
```

```
<210> SEQ ID NO 16
<211> LENGTH: 315
<212> TYPE: DNA
<213> ORGANISM: Artificial Sequence
<220> FEATURE:
<223> OTHER INFORMATION: antigen binding molecule

<400> SEQUENCE: 16
```

```
ggtgatccag ttgcacctac tgtcctcatc ttcccaccag ctgctgatca ggtggcaact     60
ggaacagtca ccatcgtgtg tgtggcgaat aaatactttc ccgatgtcac cgtcacctgg    120
gaggtggatg gcaccaccca aacaactggc atcgagaaca gtaaaacacc gcagaattct    180
gcagattgta cctacaacct cagcagcact ctgacactga ccagcacaca gtacaacagc    240
cacaaagagt acacctgcaa ggtgacccag ggcacgacct cagtcgtcca gagcttcaat    300
aggggtgact gttag                                                    315
```

```
<210> SEQ ID NO 17
<211> LENGTH: 239
<212> TYPE: PRT
<213> ORGANISM: Artificial Sequence
<220> FEATURE:
<223> OTHER INFORMATION: antigen binding molecule

<400> SEQUENCE: 17
```

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ala Ser
            20                  25                  30

Val Ser Ala Ala Val Gly Gly Thr Val Thr Ile Asn Cys Gln Ala Ser
        35                  40                  45
```

```
Gln Ser Val Tyr Ser Ser Asn Leu Leu Thr Trp Tyr Gln Lys Lys Pro
         50                  55                  60
Gly Gln Pro Pro Lys Leu Leu Ile Tyr Glu Ala Ser Lys Leu Pro Ser
 65                  70                  75                  80
Gly Ile Pro Ser Arg Phe Ser Gly Ser Gly Ser Gly Thr Gln Phe Thr
                 85                  90                  95
Leu Thr Ile Ser Asp Val Gln Cys Ala Asp Ala Ala Thr Tyr Tyr Cys
                100                 105                 110
Leu Gly Ile Tyr Asp Cys Val Leu Ala Asp Cys Gln Ala Phe Gly Gly
                115                 120                 125
Gly Thr Glu Val Val Lys Gly Asp Pro Val Ala Pro Thr Val Leu
130                 135                 140
Ile Phe Pro Pro Ala Ala Asp Gln Val Ala Thr Gly Thr Val Thr Ile
145                 150                 155                 160
Val Cys Val Ala Asn Lys Tyr Phe Pro Asp Val Thr Val Thr Trp Glu
                165                 170                 175
Val Asp Gly Thr Thr Gln Thr Thr Gly Ile Glu Asn Ser Lys Thr Pro
                180                 185                 190
Gln Asn Ser Ala Asp Cys Thr Tyr Asn Leu Ser Ser Thr Leu Thr Leu
                195                 200                 205
Thr Ser Thr Gln Tyr Asn Ser His Lys Glu Tyr Thr Cys Lys Val Thr
210                 215                 220
Gln Gly Thr Thr Ser Val Val Gln Ser Phe Asn Arg Gly Asp Cys
225                 230                 235
```

```
<210> SEQ ID NO 18
<211> LENGTH: 720
<212> TYPE: DNA
<213> ORGANISM: Artificial Sequence
<220> FEATURE:
<223> OTHER INFORMATION: antigen binding molecule

<400> SEQUENCE: 18
atggacacga gggcccccac tcagctgctg gggctcctgc tgctctggct cccaggtgcc    60
acatttgccc aagtgctgac ccagactcca gcctcggtgt ctgcagctgt gggaggcaca   120
gtcaccatca actgccaggc cagtcagagt gtttatagca gcaacctctt aacctggtat   180
cagaagaaac cagggcagcc tcccaagctc ctgatctacg aagcatccaa actgccatct   240
gggatcccat cgcgcttcag cggcagtgga tctgggacac agttcactct caccatcagc   300
gacgtacagt gtgccgatgc tgccacttac tactgtctag catttatga ttgtgtgctt   360 gctgattgtc aggctttcgg cggagggacc gaagtggtgg tcaaaggtga tccagttgca   420
cctactgtcc tcatcttccc accagctgct gatcaggtgg caactggaac agtcaccatc   480
gtgtgtgtgg cgaataaata ctttcccgat gtcaccgtca cctgggaggt ggatggcacc   540
acccaaacaa ctggcatcga gaacagtaaa acaccgcaga attctgcaga ttgtacctac   600
aacctcagca gcactctgac actgaccagc acacagtaca acagccacaa agagtacacc   660
tgcaaggtga cccagggcac gacctcagtc gtccagagct tcaataggg tgactgttag   720
```

```
<210> SEQ ID NO 19
<211> LENGTH: 13
<212> TYPE: PRT
<213> ORGANISM: Artificial Sequence
<220> FEATURE:
<223> OTHER INFORMATION: antigen binding molecule
```

<400> SEQUENCE: 19

Gln Ala Ser Gln Ser Val Tyr Ser Ser Asn Leu Leu Thr
1               5                   10

<210> SEQ ID NO 20
<211> LENGTH: 7
<212> TYPE: PRT
<213> ORGANISM: Artificial Sequence
<220> FEATURE:
<223> OTHER INFORMATION: antigen binding molecule

<400> SEQUENCE: 20

Glu Ala Ser Lys Leu Pro Ser
1               5

<210> SEQ ID NO 21
<211> LENGTH: 13
<212> TYPE: PRT
<213> ORGANISM: Artificial Sequence
<220> FEATURE:
<223> OTHER INFORMATION: antigen binding molecule

<400> SEQUENCE: 21

Leu Gly Ile Tyr Asp Cys Val Leu Ala Asp Cys Gln Ala
1               5                   10

<210> SEQ ID NO 22
<211> LENGTH: 5
<212> TYPE: PRT
<213> ORGANISM: Artificial Sequence
<220> FEATURE:
<223> OTHER INFORMATION: antigen binding molecule

<400> SEQUENCE: 22

Asn Asn Trp Ile His
1               5

<210> SEQ ID NO 23
<211> LENGTH: 16
<212> TYPE: PRT
<213> ORGANISM: Artificial Sequence
<220> FEATURE:
<223> OTHER INFORMATION: antigen binding molecule

<400> SEQUENCE: 23

Cys Val Ser Gly Ser Ser Gly Asn Ile Tyr Tyr Ala Thr Trp Ala Lys
1               5                   10                  15

<210> SEQ ID NO 24
<211> LENGTH: 4
<212> TYPE: PRT
<213> ORGANISM: Artificial Sequence
<220> FEATURE:
<223> OTHER INFORMATION: antigen binding molecule

<400> SEQUENCE: 24

Gly Trp Asn Leu
1

<210> SEQ ID NO 25
<211> LENGTH: 7
<212> TYPE: PRT
<213> ORGANISM: Artificial Sequence
<220> FEATURE:
<223> OTHER INFORMATION: antigen binding molecule

<400> SEQUENCE: 25

```
Gly Phe Asp Leu Gly Asn Asn
1               5

<210> SEQ ID NO 26
<211> LENGTH: 5
<212> TYPE: PRT
<213> ORGANISM: Artificial Sequence
<220> FEATURE:
<223> OTHER INFORMATION: antigen binding molecule

<400> SEQUENCE: 26

Ser Gly Ser Ser Gly
1               5

<210> SEQ ID NO 27
<211> LENGTH: 8
<212> TYPE: PRT
<213> ORGANISM: Artificial Sequence
<220> FEATURE:
<223> OTHER INFORMATION: antigen binding molecule

<400> SEQUENCE: 27

Gly Phe Asp Leu Gly Asn Asn Trp
1               5

<210> SEQ ID NO 28
<211> LENGTH: 7
<212> TYPE: PRT
<213> ORGANISM: Artificial Sequence
<220> FEATURE:
<223> OTHER INFORMATION: antigen binding molecule

<400> SEQUENCE: 28

Val Ser Gly Ser Ser Gly Asn
1               5

<210> SEQ ID NO 29
<211> LENGTH: 6
<212> TYPE: PRT
<213> ORGANISM: Artificial Sequence
<220> FEATURE:
<223> OTHER INFORMATION: antigen binding molecule

<400> SEQUENCE: 29

Ala Arg Gly Trp Asn Leu
1               5

<210> SEQ ID NO 30
<211> LENGTH: 15
<212> TYPE: PRT
<213> ORGANISM: Artificial Sequence
<220> FEATURE:
<223> OTHER INFORMATION: antigen binding molecule

<400> SEQUENCE: 30

Ala Thr Tyr Pro Ser Ser Asp Val Pro Ser Asp Ala Thr Leu Thr
1               5                   10                  15

<210> SEQ ID NO 31
<211> LENGTH: 11
<212> TYPE: PRT
<213> ORGANISM: Artificial Sequence
<220> FEATURE:
<223> OTHER INFORMATION: antigen binding molecule

<400> SEQUENCE: 31
```

```
Lys Asp Pro Arg Ser Gln Asp Ser Thr Leu Cys
1               5                  10
```

<210> SEQ ID NO 32
<211> LENGTH: 17
<212> TYPE: PRT
<213> ORGANISM: Artificial Sequence
<220> FEATURE:
<223> OTHER INFORMATION: antigen binding molecule

<400> SEQUENCE: 32

```
Glu Asp Ala Thr Tyr Pro Ser Ser Asp Val Pro Ser Asp Ala Thr Leu
1               5                   10                  15

Thr
```

<210> SEQ ID NO 33
<211> LENGTH: 454
<212> TYPE: PRT
<213> ORGANISM: Artificial Sequence
<220> FEATURE:
<223> OTHER INFORMATION: antigen binding molecule

<400> SEQUENCE: 33

```
Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
                20                  25                  30

Pro Glu Gly Ser Leu Thr Leu Thr Cys Thr Ala Ser Gly Phe Asp Leu
            35                  40                  45

Gly Asn Asn Trp Ile His Trp Val Arg His Ala Pro Gly Lys Gly Leu
    50                  55                  60

Glu Trp Ile Ala Cys Val Ser Gly Ser Gly Asn Ile Tyr Tyr Ala
65                  70                  75                  80

Thr Trp Ala Lys Gly Arg Phe Thr Met Ser Lys Ala Ser Ser Thr Thr
                85                  90                  95

Val Thr Leu Arg Met Thr Ser Leu Thr Ala Ala Asp Thr Ala Thr Tyr
                100                 105                 110

Phe Cys Ala Arg Gly Trp Asn Leu Trp Gly Pro Gly Thr Leu Val Thr
            115                 120                 125

Val Ser Ser Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
                180                 185                 190

Leu Tyr Ser Leu Ser Ser Val Val Ser Val Thr Ser Ser Ser Gln Pro
            195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
                260                 265                 270
```

Val Ser Gln Asp Asp Pro Glu Val Gln Phe Thr Trp Tyr Ile Asn Asn
                275                 280                 285

Glu Gln Val Arg Thr Ala Arg Pro Pro Leu Arg Glu Gln Gln Phe Asn
            290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Ser Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450

<210> SEQ ID NO 34
<211> LENGTH: 1365
<212> TYPE: DNA
<213> ORGANISM: Artificial Sequence
<220> FEATURE:
<223> OTHER INFORMATION: antigen binding molecule

<400> SEQUENCE: 34
atggagactg gctgcgctg cttctcctg gtcgctgtgc tcaaaggtgt ccagtgtcag      60
gaacagctgg tggagtccgg gggaggcctg gtccagcctg agggatccct gacactcacc     120
tgcacagcct ctggattcga cctcggtaac aactggatac actgggtccg ccacgctcca    180
gggaagggac tggaatggat cgcatgcgtt agtggtagta gcggcaacat ttactacgcg    240
acttgggcga aaggccgatt caccatgtcc aaagcctcgt cgaccacggt gactctacga    300
atgaccagtc tgacagccgc ggacacggcc acctatttct gtgcgagagg atggaacttg    360
tggggcccag cacccctggt caccgtctcc tcagggcaac taaggctccc atcagtcttc    420
ccactggccc cctgctgcgg ggacacaccc agctccacgg tgaccctggg ctgcctggtc    480
aaagggtacc tcccggagcc agtgaccgtg acctggaact cgggcaccct caccaatggg    540
gtacgcacct tcccgtccgt ccggcagtcc tcaggcctct actcgctgag cagcgtggtg    600
agcgtgacct caagcagcca gcccgtcacc tgcaacgtgg cccacccagc caccaacacc    660
aaagtggaca gaccgttgc gcctcgaca tgcagcaagc ccacgtgccc acccctgaa      720 ctcctggggg gaccgtctgt cttcatcttc ccccaaaac ccaaggacac cctcatgatc    780
tcacgcaccc ccgaggtcac atgcgtggtg gtggacgtga gccaggatga ccccgaggtg    840
cagttcacat ggtacataaa caacgagcag gtgcgcaccg cccggccgcc gctacgggag    900
cagcagttca acagcacgat ccgcgtggtc agcaccctcc ccatcgcgca ccaggactgg    960
ctgaggggca aggagttcaa gtgcaaagtc cacaacaagg cactcccggc ccccatcgag    1020

```
aaaaccatct ccaaagccag agggcagccc ctggagccga aggtctacac catgggccct      1080 ccccggggagg agctgagcag caggtcggtc agcctgacct gcatgatcaa cggcttctac      1140
ccttccgaca tctcggtgga gtgggagaag aacgggaagg cagaggacaa ctacaagacc      1200
acgccggccg tgctggacag cgacggctcc tacttcctct acagcaagct ctcagtgccc      1260
acgagtgagt ggcagcgggg cgacgtcttc acctgctccg tgatgcacga ggccttgcac      1320
aaccactaca cgcagaagtc catctcccgc tctccgggta aatga                     1365
```

<210> SEQ ID NO 35
<211> LENGTH: 454
<212> TYPE: PRT
<213> ORGANISM: Artificial Sequence
<220> FEATURE:
<223> OTHER INFORMATION: antigen binding molecule

<400> SEQUENCE: 35

```
Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Thr Ala Ser Gly Phe Asp Leu
        35                  40                  45

Gly Asn Asn Trp Ile His Trp Val Arg His Ala Pro Gly Lys Gly Leu
    50                  55                  60

Glu Trp Ile Ala Cys Val Ser Gly Ser Ser Gly Asn Ile Tyr Tyr Ala
65                  70                  75                  80

Thr Trp Ala Lys Gly Arg Phe Thr Met Ser Lys Ala Ser Ser Thr Thr
                85                  90                  95

Val Thr Leu Arg Met Thr Ser Leu Thr Ala Ala Asp Thr Ala Thr Tyr
            100                 105                 110

Phe Cys Ala Arg Gly Trp Asn Leu Trp Gly Pro Gly Thr Leu Val Thr
        115                 120                 125

Val Ser Ser Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300
```

```
Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
            325                 330                 335

Ala Pro Ile Glu Lys Thr Ile Ser Lys Ala Arg Gly Gln Pro Leu Glu
        340                 345                 350

Pro Lys Val Tyr Thr Met Gly Pro Pro Arg Glu Glu Leu Ser Ser Arg
            355                 360                 365

Ser Val Ser Leu Thr Cys Met Ile Asn Gly Phe Tyr Pro Ser Asp Ile
370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Ser Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450

<210> SEQ ID NO 36
<211> LENGTH: 1365
<212> TYPE: DNA
<213> ORGANISM: Artificial Sequence
<220> FEATURE:
<223> OTHER INFORMATION: antigen binding molecule

<400> SEQUENCE: 36
atggagactg ggctgcgctg gcttctcctg gtcgctgtgc tcaaaggtgt ccagtgtcag      60
gaacagctgg tggagtccgg gggaggcctg gtccagcctg agggatccct gacactcacc     120
tgcacagcct ctggattcga cctcggtaac aactggatac tgggtccgc cacgctcca     180 gggaagggac tggaatggat cgcatgcgtt agtggtagta gcggcaacat ttactacgcg     240
acttgggcga aaggccgatt caccatgtcc aaagcctcgt cgaccacggt gactctacga     300
atgaccagtc tgacagccgc ggacacggcc acctatttct gtgcgagagg atggaacttg     360
tggggcccag gcaccctggt caccgtctcc tcagggcaac taaggctcc atcagtcttc     420 ccactggccc cctgctgcgg ggacacaccc agctccacgg tgaccctggg ctgcctggtc     480
aaagggtacc tcccggagcc agtgaccgtg acctggaact cgggcaccct caccaatggg     540
gtacgcacct tcccgtccgt ccggcagtcc tcaggcctct actcgctgag cagcgtggtg     600
agcgtgacct caagcagcca gcccgtcacc tgcaacgtgg cccacccagc caccaacacc     660
aaagtggaca gaccgttgc gccctcgaca tgcagcaagc ccacgtgccc acccctgaa     720 ctcctggggg gaccgtctgt cttcatcttc cccccaaaac ccaaggacac cctcatgatc     780
tcacgcaccc ccgaggtcac atgcgtggtg gtggacgtga gccaggatga ccccgaggtg     840
cagttcacat ggtacataaa caacgagcag gtgcgcaccg cccggccgcc gctacgggag     900
cagcagttca cagcacgat ccgcgtggtc agcaccctcc ccatcgcgca ccaggactgg     960
ctgaggggca aggagttcaa gtgcaaagtc acaacaagg cactcccggc cccatcgag    1020 aaaaccatct ccaaagccag agggcagccc ctggagccga aggtctacac catgggccct    1080
ccccgggagg agctgagcag caggtcggtc agcctgacct gcatgatcaa cggcttctac    1140
```

```
ccttccgaca tctcggtgga gtgggagaag aacgggaagg cagaggacaa ctacaagacc   1200
acgccggccg tgctggacag cgacggctcc tacttcctct acagcaagct ctcagtgccc   1260
acgagtgagt ggcagcgggg cgacgtcttc acctgctccg tgatgcacga ggccttgcac   1320
aaccactaca cgcagaagtc catctcccgc tctccgggta aatga                  1365
```

<210> SEQ ID NO 37
<211> LENGTH: 454
<212> TYPE: PRT
<213> ORGANISM: Artificial Sequence
<220> FEATURE:
<223> OTHER INFORMATION: antigen binding molecule

<400> SEQUENCE: 37

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
                20                  25                  30

Pro Glu Gly Ser Leu Thr Leu Thr Cys Thr Ala Ser Gly Phe Asp Leu
            35                  40                  45

Gly Asn Asn Trp Ile His Trp Val Arg His Ala Pro Gly Lys Gly Leu
        50                  55                  60

Glu Trp Ile Ala Cys Val Ser Gly Ser Ser Gly Asn Ile Tyr Tyr Ala
65                  70                  75                  80

Thr Trp Ala Lys Gly Arg Phe Thr Met Ser Lys Ala Ser Ser Thr Thr
                85                  90                  95

Val Thr Leu Arg Met Thr Ser Leu Thr Ala Ala Asp Thr Ala Thr Tyr
            100                 105                 110

Phe Cys Ala Arg Gly Trp Asn Leu Trp Gly Pro Gly Thr Leu Val Thr
        115                 120                 125

Val Ser Ser Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro

|  |  | 325 |  |  | 330 |  |  | 335 |  |  |  |
|---|---|---|---|---|---|---|---|---|---|---|---|

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Ser Lys
            405                 410                 415

Leu Ser Val Pro Thr Ser Glu Trp Gln Arg Gly Asp Val Phe Thr Cys
        420                 425                 430

Ser Val Met His Glu Ala Leu His Asn His Tyr Thr Gln Lys Ser Ile
            435                 440                 445

Ser Arg Ser Pro Gly Lys
    450

<210> SEQ ID NO 38
<211> LENGTH: 1365
<212> TYPE: DNA
<213> ORGANISM: Artificial Sequence
<220> FEATURE:
<223> OTHER INFORMATION: antigen binding molecule

<400> SEQUENCE: 38

| atggagactg | ggctgcgctg | gcttctcctg | gtcgctgtgc | tcaaaggtgt | ccagtgtcag | 60 |
|---|---|---|---|---|---|---|
| gaacagctgg | tggagtccgg | gggaggcctg | gtccagcctg | agggatccct | gacactcacc | 120 |
| tgcacagcct | ctggattcga | cctcggtaac | aactggatac | actgggtccg | ccacgctcca | 180 |
| gggaagggac | tggaatggat | cgcatgcgtt | agtggtagta | gcggcaacat | ttactacgcg | 240 |
| acttgggcga | aaggccgatt | caccatgtcc | aaagcctcgt | cgaccacggt | gactctacga | 300 |
| atgaccagtc | tgacagccgc | ggacacggcc | acctatttct | gtgcgagagg | atggaacttg | 360 |
| tggggcccag | gcaccctggt | caccgtctcc | tcagggcaac | ctaaggctcc | atcagtcttc | 420 |
| ccactggccc | cctgctgcgg | ggacacaccc | agctccacgg | tgaccctggg | ctgcctggtc | 480 |
| aaagggtacc | tcccggagcc | agtgaccgtg | acctggaact | cgggcaccct | accaatggg | 540 |
| gtacgcacct | tcccgtccgt | ccggcagtcc | tcaggcctct | actcgctgag | cagcgtggtg | 600 |
| agcgtgacct | caagcagcca | gcccgtcacc | tgcaacgtgg | cccacccagc | caccaacacc | 660 |
| aaagtggaca | gaccgttgc | ccctcgaca | tgcagcaagc | ccacgtgccc | acccctgaa | 720 |
| ctcctggggg | gaccgtctgt | cttcatcttc | cccccaaaac | ccaaggacac | cctcatgatc | 780 |
| tcacgcaccc | ccgaggtcac | atgcgtggtg | gtggacgtga | gccaggatga | ccccgaggtg | 840 |
| cagttcacat | ggtacataaa | caacgagcag | gtgcgcaccg | cccggccgcc | gctacgggag | 900 |
| cagcagttca | acagcacgat | ccgcgtggtc | agcaccctcc | ccatcgcgca | ccaggactgg | 960 |
| ctgaggggca | aggagttcaa | gtgcaaagtc | cacaacaagg | cactcccggc | ccccatcgag | 1020 |
| aaaaccatct | ccaaagccag | agggcagccc | ctggagccga | aggtctacac | catgggccct | 1080 |
| ccccgggagg | agctgagcag | caggtcggtc | agcctgacct | gcatgatcaa | cggcttctac | 1140 |
| ccttccgaca | tctcggtgga | gtgggagaag | aacgggaagg | cagaggacaa | ctacaagacc | 1200 |
| acgccggccg | tgctggacag | cgacggctcc | tacttcctct | acagcaagct | ctcagtgccc | 1260 |
| acgagtgagt | ggcagcgggg | cgacgtcttc | acctgctccg | tgatgcacga | ggccttgcac | 1320 | aaccactaca cgcagaagtc catctcccgc tctccgggta aatga    1365

<210> SEQ ID NO 39
<211> LENGTH: 456
<212> TYPE: PRT
<213> ORGANISM: Artificial Sequence
<220> FEATURE:
<223> OTHER INFORMATION: antigen binding molecule

<400> SEQUENCE: 39

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Glu Gly Ser Leu Thr Leu Thr Cys Thr Ala Ser Gly Phe Ser Phe Ser
        35                  40                  45

Ser Ser Tyr Trp Leu Cys Trp Val Arg Gln Ala Pro Gly Lys Gly Leu
    50                  55                  60

Glu Trp Ile Gly Cys Ile Asp Asn Ser Ser Gly Arg Thr Tyr Arg Ala
65                  70                  75                  80

Asn Trp Ala Lys Gly Arg Phe Thr Ile Ser Arg Thr Ser Ser Thr Thr
                85                  90                  95

Val Thr Leu Gln Met Thr Arg Leu Thr Ala Ala Asp Thr Ala Thr Tyr
            100                 105                 110

Phe Cys Ala Arg Gly Ile Asp Ser Tyr Leu Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350
```

```
Leu Glu Pro Lys Val Tyr Thr Met Gly Pro Pro Arg Glu Glu Leu Ser
            355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
                420                 425                 430

Thr Cys Ser Val Met His Glu Ala Leu His Asn His Tyr Thr Gln Lys
                435                 440                 445

Ser Ile Ser Arg Ser Pro Gly Lys
    450                 455

<210> SEQ ID NO 40
<211> LENGTH: 456
<212> TYPE: PRT
<213> ORGANISM: Artificial Sequence
<220> FEATURE:
<223> OTHER INFORMATION: antigen binding molecule

<400> SEQUENCE: 40

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Phe Thr Leu Ser
        35                  40                  45

Ser Asn Tyr Trp Ile Cys Trp Val Arg Gln Ala Pro Gly Lys Gly Leu
    50                  55                  60

Lys Trp Ile Ala Cys Ile Asp Asn Ser Asp Gly Gly Thr Tyr Tyr Ala
65                  70                  75                  80

Asn Trp Ala Lys Gly Arg Phe Thr Ile Ser Lys Thr Ser Ser Thr Thr
                85                  90                  95

Val Thr Leu Arg Met Pro Ser Leu Thr Ala Ala Asp Thr Ala Ala Tyr
            100                 105                 110

Phe Cys Ala Arg Gly Ile Asp Thr Tyr Val Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255
```

```
Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455

<210> SEQ ID NO 41
<211> LENGTH: 239
<212> TYPE: PRT
<213> ORGANISM: Artificial Sequence
<220> FEATURE:
<223> OTHER INFORMATION: antigen binding molecule

<400> SEQUENCE: 41

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ala Ser
            20                  25                  30

Val Ser Ala Ala Val Gly Gly Thr Val Thr Ile Asn Cys Gln Ala Ser
        35                  40                  45

Gln Ser Val Tyr Ser Ser Asn Leu Leu Thr Trp Tyr Gln Lys Lys Pro
    50                  55                  60

Gly Gln Pro Pro Lys Leu Leu Ile Tyr Glu Ala Ser Lys Leu Pro Ser
65                  70                  75                  80

Gly Ile Pro Ser Arg Phe Ser Gly Ser Gly Ser Gly Thr Gln Phe Thr
                85                  90                  95

Leu Thr Ile Ser Asp Val Gln Cys Ala Asp Ala Ala Thr Tyr Tyr Cys
            100                 105                 110

Leu Gly Ile Tyr Asp Cys Val Leu Ala Asp Cys Gln Ala Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160
```

Val Cys Val Ala Asn Lys Tyr Phe Pro Asp Val Thr Val Thr Trp Glu
            165                 170                 175

Val Asp Gly Thr Thr Gln Thr Thr Gly Ile Glu Asn Ser Lys Thr Pro
        180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 42
<211> LENGTH: 720
<212> TYPE: DNA
<213> ORGANISM: Artificial Sequence
<220> FEATURE:
<223> OTHER INFORMATION: antigen binding molecule

<400> SEQUENCE: 42

```
atggacacga gggcccccac tcagctgctg gggctcctgc tgctctggct cccaggtgcc     60
acatttgccc aagtgctgac ccagactcca gcctcggtgt ctgcagctgt gggaggcaca    120
gtcaccatca actgccaggc cagtcagagt gtttatagca gcaacctctt aacctggtat    180
cagaagaaac cagggcagcc tcccaagctc ctgatctacg aagcatccaa actgccatct    240
gggatcccat cgcgcttcag cggcagtgga tctgggacac agttcactct caccatcagc    300
gacgtacagt gtgccgatgc tgccacttac tactgtctag cattatga ttgtgtgctt      360
gctgattgtc aggctttcgg cggagggacc gaagtggtgg tcaaaggtga tccagttgca    420
cctactgtcc tcatcttccc accagctgct gatcaggtgg caactggaac agtcaccatc    480
gtgtgtgtgg cgaataaata ctttcccgat gtcaccgtca cctgggaggt ggatggcacc    540
acccaaacaa ctggcatcga aacagtaaa acaccgcaga attctgcaga ttgtacctac    600
aacctcagca gcactctgac actgaccagc acacagtaca cagcacaa agagtacacc     660
tgcaaggtga cccagggcac gacctcagtc gtccagagct caataggg tgactgttag      720
```

<210> SEQ ID NO 43
<211> LENGTH: 239
<212> TYPE: PRT
<213> ORGANISM: Artificial Sequence
<220> FEATURE:
<223> OTHER INFORMATION: antigen binding molecule

<400> SEQUENCE: 43

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ala Ser
            20                  25                  30

Val Ser Ala Ala Val Gly Gly Thr Val Thr Ile Asn Cys Gln Ala Ser
        35                  40                  45

Gln Ser Val Tyr Ser Ser Asn Leu Leu Thr Trp Tyr Gln Lys Lys Pro
    50                  55                  60

Gly Gln Pro Pro Lys Leu Leu Ile Tyr Glu Ala Ser Lys Leu Pro Ser
65                  70                  75                  80

Gly Ile Pro Ser Arg Phe Ser Gly Ser Gly Ser Gly Thr Gln Phe Thr
                85                  90                  95

Leu Thr Ile Ser Asp Val Gln Cys Ala Asp Ala Ala Thr Tyr Tyr Cys
            100                 105                 110

```
Leu Gly Ile Tyr Asp Cys Val Leu Ala Asp Cys Gln Ala Phe Gly Gly
        115                 120                 125

Gly Thr Glu Val Val Lys Gly Asp Pro Val Ala Pro Thr Val Leu
130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235
```

<210> SEQ ID NO 44
<211> LENGTH: 720
<212> TYPE: DNA
<213> ORGANISM: Artificial Sequence
<220> FEATURE:
<223> OTHER INFORMATION: antigen binding molecule

<400> SEQUENCE: 44

```
atggacacga gggcccccac tcagctgctg gggctcctgc tgctctggct cccaggtgcc    60
acatttgccc aagtgctgac ccagactcca gcctcggtgt ctgcagctgt gggaggcaca   120
gtcaccatca actgccaggc cagtcagagt gtttatagca gcaacctctt aacctggtat   180
cagaagaaac agggcagcc tcccaagctc ctgatctacg aagcatccaa actgccatct   240
gggatcccat cgcgcttcag cggcagtgga tctgggacac agttcactct caccatcagc   300
gacgtacagt gtgccgatgc tgccacttac tactgtctag catttatga ttgtgtgctt   360
gctgattgtc aggctttcgg cggagggacc gaagtggtgg tcaaaggtga tccagttgca   420
cctactgtcc tcatcttccc accagctgct gatcaggtgg caactggaac agtcaccatc   480
gtgtgtgtgg cgaataaata ctttcccgat gtcaccgtca cctgggaggt ggatggcacc   540
acccaaacaa ctggcatcga aacagtaaa acaccgcaga attctgcaga ttgtacctac   600
aacctcagca gcactctgac actgaccagc acacagtaca acagccacaa agagtacacc   660
tgcaaggtga cccagggcac gacctcagtc gtccagagct tcaataggg tgactgttag   720
```

<210> SEQ ID NO 45
<211> LENGTH: 239
<212> TYPE: PRT
<213> ORGANISM: Artificial Sequence
<220> FEATURE:
<223> OTHER INFORMATION: antigen binding molecule

<400> SEQUENCE: 45

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ala Ser
            20                  25                  30

Val Ser Ala Ala Val Gly Gly Thr Val Thr Ile Asn Cys Gln Ala Ser
        35                  40                  45

Gln Ser Val Tyr Ser Ser Asn Leu Leu Thr Trp Tyr Gln Lys Lys Pro
```

Gly Gln Pro Pro Lys Leu Leu Ile Tyr Glu Ala Ser Lys Leu Pro Ser
65                  70                  75                  80

Gly Ile Pro Ser Arg Phe Ser Gly Ser Gly Thr Gln Phe Thr
            85                  90                  95

Leu Thr Ile Ser Asp Val Gln Cys Ala Asp Ala Ala Thr Tyr Tyr Cys
            100                 105                 110

Leu Gly Ile Tyr Asp Cys Val Leu Ala Asp Cys Gln Ala Phe Gly Gly
            115                 120                 125

Gly Thr Glu Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 46
<211> LENGTH: 720
<212> TYPE: DNA
<213> ORGANISM: Artificial Sequence
<220> FEATURE:
<223> OTHER INFORMATION: antigen binding molecule

<400> SEQUENCE: 46

```
atggacacga gggcccccac tcagctgctg gggctcctgc tgctctggct cccaggtgcc    60
acatttgccc aagtgctgac ccagactcca gcctcggtgt ctgcagctgt gggaggcaca   120
gtcaccatca actgccaggc cagtcagagt gtttatagca acaacctctt aacctggtat   180
cagaagaaac cagggcagcc tcccaagctc ctgatctacg aagcatccaa actgccatct   240
gggatcccat cgcgcttcag cggcagtgga tctgggacac agttcactct caccatcagc   300
gacgtacagt gtgccgatgc tgccacttac tactgtctag cattatga ttgtgtgctt   360
gctgattgtc aggcttttcgg cggagggacc gaagtggtgg tcaaaggtga tccagttgca   420
cctactgtcc tcatcttccc accagctgct gatcaggtgg caactggaac agtcaccatc   480
gtgtgtgtgg cgaataaata ctttcccgat gtcaccgtca cctgggaggt ggatggcacc   540
acccaaacaa ctggcatcga aacagtaaa acaccgcaga attctgcaga ttgtacctac   600
aacctcagca gcactctgac actgaccagc acacagtaca acagccacaa agagtacacc   660
tgcaaggtga cccagggcac gacctcagtc gtccagagct caatagggg tgactgttag   720
```

<210> SEQ ID NO 47
<211> LENGTH: 239
<212> TYPE: PRT
<213> ORGANISM: Artificial Sequence
<220> FEATURE:
<223> OTHER INFORMATION: antigen binding molecule

<400> SEQUENCE: 47

Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Thr Pro Ser Ser
                20                  25                  30

Val Ser Ala Ala Val Gly Gly Thr Val Thr Ile Asn Cys Gln Ser Ser
            35                  40                  45

Gln Ser Val Val Asn Thr Asn Tyr Leu Gly Trp Tyr Gln Gln Lys Pro
        50                  55                  60

Gly Gln Pro Pro Lys Leu Leu Ile Tyr Gln Ala Ser Lys Leu Val Ser
65                  70                  75                  80

Gly Val Pro Ser Arg Phe Ser Gly Ser Gly Ser Gly Thr Gln Phe Thr
                85                  90                  95

Leu Thr Ile Ser Asp Leu Glu Cys Asp Asp Ala Ala Thr Tyr Tyr Cys
                100                 105                 110

Val Gly Thr Tyr Asp Cys Asn Arg Ser Asp Cys Gly Ala Phe Gly Gly
            115                 120                 125

Gly Thr Glu Val Val Lys Gly Asp Pro Val Ala Pro Thr Val Leu
        130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
                180                 185                 190

Gln Asn Ser Ala Asp Cys Thr Tyr Asn Leu Ser Ser Thr Leu Thr Leu
            195                 200                 205

Thr Ser Thr Gln Tyr Asn Ser His Lys Glu Tyr Thr Cys Lys Val Thr
        210                 215                 220

Gln Gly Thr Thr Ser Val Val Gln Ser Phe Asn Arg Gly Asp Cys
225                 230                 235

<210> SEQ ID NO 48
<211> LENGTH: 720
<212> TYPE: DNA
<213> ORGANISM: Artificial Sequence
<220> FEATURE:
<223> OTHER INFORMATION: antigen binding molecule

<400> SEQUENCE: 48
atggacacga gggcccccac tcagctgctg gggctcctgc tgctctggct cccaggtgcc    60
acatttgctc aagtgctgac ccagactcca tcctccgtgt ctgcagctgt gggaggcaca   120
gtcaccatca attgccagtc cagtcagagt gttgttaata ctaactattt aggctggtat   180
cagcagaaac agggcagcc tcccaagctc ctgatctacc aggcatccaa actagtatct   240
ggggtcccat cgcggttcag tggcagtgga tctgggacac agttcactct caccatcagc   300
gacctggagt gtgacgatgc tgccacttac tactgtgtag gcacttatga ttgtaataga   360
agcgattgtg gggctttcgg cggagggacc gaggtggtgg tcaaaggtga tccagttgca   420
cctactgtcc tcatcttccc accagctgct gatcaggtgg caactggaac agtcaccatc   480
gtgtgtgtgg cgaataaata ctttcccgat gtcaccgtca cctgggaggt ggatggcacc   540
acccaaacaa ctggcatcga gaacagtaaa acaccgcaga attctgcaga ttgtacctac   600
aacctcagca gcactctgac actgaccagc acacagtaca acagccacaa agagtacacc   660
tgcaaggtga cccagggcac gacctcagtc gtccagagct caataggggg tgactgttag   720

<210> SEQ ID NO 49
<211> LENGTH: 239
<212> TYPE: PRT
<213> ORGANISM: Artificial Sequence
<220> FEATURE:
<223> OTHER INFORMATION: antigen binding molecule

<400> SEQUENCE: 49

```
Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Thr Pro Ser Ser
                20                  25                  30

Val Ser Ala Ala Val Gly Gly Thr Val Thr Ile Asn Cys Gln Ser Ser
                35                  40                  45

Gln Ser Val Val Thr Asn Lys Tyr Leu Gly Trp Tyr Gln Gln Lys Pro
    50                  55                  60

Gly Gln Pro Pro Lys Leu Leu Ile Tyr Gln Ala Ser Arg Leu Pro Ser
65                  70                  75                  80

Gly Val Ser Ser Arg Phe Ser Gly Ser Gly Phe Gly Thr Gln Phe Thr
                85                  90                  95

Leu Thr Ile Ser Asp Val Gln Cys Asp Asp Ala Ala Thr Tyr Tyr Cys
                100                 105                 110

Val Gly Thr Tyr Asp Cys Lys Arg Ala Asp Cys Gly Ala Phe Gly Gly
                115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
                180                 185                 190

Gln Asn Ser Ala Asp Cys Thr Tyr Asn Leu Ser Ser Thr Leu Thr Leu
            195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235
```

<210> SEQ ID NO 50
<211> LENGTH: 720
<212> TYPE: DNA
<213> ORGANISM: Artificial Sequence
<220> FEATURE:
<223> OTHER INFORMATION: antigen binding molecule

<400> SEQUENCE: 50

```
atggacacga gggcccccac tcagctgctg ggctcctgc tgctctggct cccaggtgcc      60
acatttgctc aagtgctgac ccagactcca tcctccgtgt ctgcagctgt gggaggcaca    120
gtcaccatca attgccagtc cagtcagagt gttgttacta ataagtactt aggctggtat    180
cagcagaaac cagggcagcc tcccaagctc ctgatctacc aggcatccag actgccatct    240
ggggtctcat cgcgcttcag cggcagtgga tttgggacac agttcactct caccatcagc    300
gacgtgcagt gtgacgatgc tgccacttac tactgtgtag gcacttatga ttgtaaacgt    360
gctgactgtg gggctttcgg cggagggacc gaggtggtgg tcaaaggtga tccagttgca    420
```

| | |
|---|---|
| cctactgtcc tcatcttccc accagctgct gatcaggtgg caactggaac agtcaccatc | 480 |
| gtgtgtgtgg cgaataaata ctttcccgat gtcaccgtca cctgggaggt ggatggcacc | 540 |
| acccaaacaa ctggcatcga aacagtaaa acaccgcaga attctgcaga ttgtacctac | 600 |
| aacctcagca gcactctgac actgaccagc acacagtaca acagccacaa agagtacacc | 660 |
| tgcaaggtga cccagggcac gacctcagtc gtccagagct caatagggg tgactgttag | 720 |

<210> SEQ ID NO 51
<211> LENGTH: 1371
<212> TYPE: DNA
<213> ORGANISM: Artificial Sequence
<220> FEATURE:
<223> OTHER INFORMATION: antigen binding molecule

<400> SEQUENCE: 51

| | |
|---|---|
| atggagactg ggctgcgctg gcttctcctg gtcgctgtgc tcaaaggtgt ccagtgtcag | 60 |
| tcgttggagg agtccggggg agacctggtc aagcctgagg gatccctgac actcacctgc | 120 |
| acagcctctg gattctcctt cagtagcagc tactggctat gttgggtccg ccaggctcca | 180 |
| gggaaggggc tggagtggat cggatgcatt gataatagta gtggtaggac ttaccgcgcg | 240 |
| aactgggcga aaggccgatt caccatctcc agaacctcgt cgaccacggt gactctgcaa | 300 |
| atgacccgtc tgacagccgc ggacacggcc acctatttct gtgcgagagg aattgatagt | 360 |
| tatttgtggg gcccgggcac cctggtcacc gtctcctcag gcaacctaa ggctccatca | 420 |
| gtcttcccac tggcccctg ctgcgggac acccagct ccacggtgac cctgggctgc | 480 |
| ctggtcaaag gtacctccc ggagccagtg accgtgacct ggaactcggg caccctcacc | 540 |
| aatggggtac gcaccttccc gtccgtcgg cagtcctcag gcctctactc gctgagcagc | 600 |
| gtggtgagcg tgacctcaag cagccagccc gtcacctgca acgtggccca cccagccacc | 660 |
| aacaccaaag tggacaagac cgttgcgccc tcgacatgca gcaagcccac gtgcccaccc | 720 |
| cctgaactcc tgggggggacc gtctgtcttc atcttccccc caaaacccaa ggacaccctc | 780 |
| atgatctcac gcaccccga ggtcacatgc gtggtggtgg acgtgagcca ggatgacccc | 840 |
| gaggtgcagt tcatggta cataaacaac gagcaggtgc gcaccgcccg gccgccgcta | 900 |
| cgggagcagc agttcaacag cacgatccgc gtggtcagca ccctccccat cgcgcaccag | 960 |
| gactggctga gggcaagga gttcaagtgc aaagtccaca caaggcact cccgccccc | 1020 |
| atcgagaaaa ccatctccaa agccagaggg cagcccctgg agccgaaggt ctacaccatg | 1080 |
| ggccctcccc gggaggagct gagcagcagg tcggtcagcc tgacctgcat gatcaacggc | 1140 |
| ttctaccctt ccgacatctc ggtggagtgg gagaagaacg ggaaggcaga ggacaactac | 1200 |
| aagaccacgc cggccgtgct ggacagcgac ggctcctact cctctacag caagctctca | 1260 |
| gtgcccacga gtgagtggca gcggggcgac gtcttcacct gctccgtgat gcacgaggcc | 1320 |
| ttgcacaacc actacacgca gaagtccatc tcccgctctc cgggtaaatg a | 1371 |

<210> SEQ ID NO 52
<211> LENGTH: 1371
<212> TYPE: DNA
<213> ORGANISM: Artificial Sequence
<220> FEATURE:
<223> OTHER INFORMATION: antigen binding molecule

<400> SEQUENCE: 52

| | |
|---|---|
| atggagactg ggctgcgctg gcttctcctg gtcgctgtgc tcaaaggtgt ccagtgtcag | 60 |
| tcgttggagg agtccggggg agacctggtc aagcctgggg catccctgac actcacctgc | 120 |

```
acagcctctg gattcaccct cagtagcaac tactggatat gctgggtccg ccaggctcca        180
gggaagggcc tgaagtggat cgcatgtatt gataatagtg atggcggcac ttactacgcg        240
aactgggcga aggccgatt caccatctcc aaaacctcgt cgaccacggt gactctgcga         300
atgcccagtc tgacagccgc ggacacggcc gcctatttct gtgcgcgagg aattgatacg        360
tacgtgtggg gcccaggcac cctggtcacc gtctcctcag gcaacctaa ggctccatca         420 gtcttcccac tggcccctg ctgcgggac acccagct ccacggtgac cctgggctgc            480
ctggtcaaag ggtacctccc ggagccagtg accgtgacct ggaactcggg caccctcacc        540
aatggggtac gcaccttccc gtccgtccgg cagtcctcag gcctctactc gctgagcagc        600
gtggtgagcg tgacctcaag cagccagccc gtcacctgca acgtggccca cccagccacc        660
aacaccaaag tggacaagac cgttgcgccc tcgacatgca gcaagcccac gtgcccaccc        720
cctgaactcc tgggggacc gtctgtcttc atcttccccc caaaacccaa ggacaccctc         780
atgatctcac gcaccccga ggtcacatgc gtggtggtgg acgtgagcca ggatgacccc        840
gaggtgcagt tcacatggta cataaacaac gagcaggtgc gcaccgcccg gccgccgcta       900
cgggagcagc agttcaacag cacgatccgc gtggtcagca ccctccccat cgcgcaccag       960
gactggctga ggggcaagga gttcaagtgc aaagtccaca caaggcact cccggccccc       1020 atcgagaaaa ccatctccaa agccagaggg cagcccctgg agccgaaggt ctacaccatg       1080
ggccctcccc gggaggagct gagcagcagg tcggtcagcc tgacctgcat gatcaacggc       1140 ttctacccctt ccgacatctc ggtggagtgg gagaagaacg ggaaggcaga ggacaactac     1200
aagaccacgc cggccgtgct ggacagcgac ggctcctact tcctctacag caagctctca      1260
gtgcccacga gtgagtggca gcggggcgac gtcttcacct gctccgtgat gcacgaggcc      1320
ttgcacaacc actacacgca gaagtccatc tcccgctctc cgggtaaatg a               1371
```

```
<210> SEQ ID NO 53
<211> LENGTH: 17
<212> TYPE: PRT
<213> ORGANISM: Artificial Sequence
<220> FEATURE:
<223> OTHER INFORMATION: antigen binding molecule

<400> SEQUENCE: 53

Thr Leu Thr Ala Asp Ser Pro Val Asp Ser Ser Pro Tyr Thr Ala Asp
1               5                   10                  15

Glu
```